United States Patent
Hwang et al.

(10) Patent No.: US 9,252,370 B2
(45) Date of Patent: *Feb. 2, 2016

(54) HETEROCYCLIC COMPOUNDS AND ORGANIC LIGHT EMITTING DEVICES INCLUDING THE SAME

(71) Applicant: SAMSUNG DISPLAY CO., LTD., Yongin, Gyeonggi-do (KR)

(72) Inventors: Seok-Hwan Hwang, Yongin (KR); Young-Kook Kim, Yongin (KR); Hye-Jin Jung, Yongin (KR); Jun-Ha Park, Yongin (KR); Eun-Young Lee, Yongin (KR); Jin-O Lim, Yongin (KR); Sang-Hyun Han, Yongin (KR); Eun-Jae Jeong, Yongin (KR); Soo-Yon Kim, Yongin (KR); Jong-Hyuk Lee, Yongin (KR)

(73) Assignee: Samsung Display Co., Ltd., Samsung-ro, Giheung-Gu, Yongin-si, Gyeonggi-Do (KR)

(*) Notice: Subject to any disclaimer, the term of this patent is extended or adjusted under 35 U.S.C. 154(b) by 257 days.

This patent is subject to a terminal disclaimer.

(21) Appl. No.: 13/826,319

(22) Filed: Mar. 14, 2013

(65) Prior Publication Data

US 2014/0124747 A1 May 8, 2014

(30) Foreign Application Priority Data

Nov. 5, 2012 (KR) .................. 10-2012-0124467

(51) Int. Cl.
H01L 51/50 (2006.01)
H01L 51/00 (2006.01)
C07D 209/56 (2006.01)

(52) U.S. Cl.
CPC .......... *H01L 51/0072* (2013.01); *C07D 209/56* (2013.01); *H01L 51/0061* (2013.01); *H01L 51/0059* (2013.01); *H01L 51/0081* (2013.01); *H01L 2251/308* (2013.01)

(58) Field of Classification Search
None
See application file for complete search history.

(56) References Cited

U.S. PATENT DOCUMENTS 3,968,051 A 7/1976 Stamm et al.
4,521,605 A 6/1985 Okazaki et al.
(Continued)

FOREIGN PATENT DOCUMENTS

JP 199612600 A 1/1996
JP 11-144873 A 5/1999
(Continued)

OTHER PUBLICATIONS

USPTO Office Action issued on Mar. 13, 2015 in connection with Applicant's cross-referenced copending U.S. Appl. No. 13/827,371.
(Continued)

*Primary Examiner* — Gregory Clark
(74) *Attorney, Agent, or Firm* — Robert E. Bushnell, Esq.

(57) ABSTRACT

Provided are heterocyclic compounds represented by general Formula 1 below and organic light-emitting devices including the same:

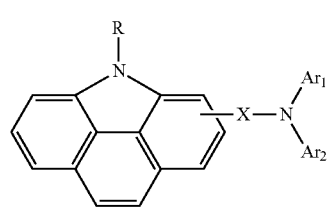

<Formula 1>

Such N-substituted diarylamino derivatives of 4,5-iminophenanthrene, when included in color fluorescent or phosphorescent organic light emitting devices in a hole transporting or hole injecting charge transport role, impart high efficiency, low driving voltages, high luminances and long lifetimes to these devices.

22 Claims, 1 Drawing Sheet

(56) References Cited

U.S. PATENT DOCUMENTS

| | | | |
|---|---|---|---|
| 4,720,432 | A | 1/1988 | VanSlyke et al. |
| 5,061,569 | A | 10/1991 | VanSlyke et al. |
| 5,635,308 | A | 6/1997 | Inoue et al. |
| 5,972,247 | A | 10/1999 | Shi et al. |
| 6,242,115 | B1 | 6/2001 | Thomson et al. |
| 6,451,461 | B2 | 9/2002 | Lee et al. |
| 6,465,115 | B2 | 10/2002 | Shi et al. |
| 6,596,415 | B2 | 7/2003 | Shi et al. |
| 6,660,410 | B2 | 12/2003 | Hosokawa |
| 6,670,054 | B1 | 12/2003 | Hu et al. |
| 6,979,414 | B2 | 12/2005 | Hosokawa |
| 7,431,997 | B2 | 10/2008 | Hwang et al. |
| 2003/0186077 | A1* | 10/2003 | Chen .................. C07D 209/80 428/690 |
| 2005/0221124 | A1 | 10/2005 | Hwang et al. |
| 2008/0258615 | A1 | 10/2008 | Begley et al. |
| 2012/0292603 | A1* | 11/2012 | Kwak et al. ................. 257/40 |
| 2013/0168646 | A1* | 7/2013 | Kim ............................ 257/40 |
| 2013/0207082 | A1* | 8/2013 | Cho et al. .................... 257/40 |

FOREIGN PATENT DOCUMENTS

| | | |
|---|---|---|
| JP | 2000003782 A | 1/2000 |
| JP | 2000-302756 A | 10/2000 |
| JP | 2003-133075 A | 5/2003 |
| JP | 2004-079265 A | 3/2004 |
| JP | 2006-151979 A | 6/2006 |
| KR | 100346984 B1 | 7/2002 |
| KR | 10-0573137 B1 | 4/2006 |

OTHER PUBLICATIONS

U.S. Appl. No. 13/827,371, filed Mar. 14, 2013.

Sigma-Aldrich, 4H-benzo[def]carbazole, printed on Sep. 2, 2015 from www.sigmaaldrich.com.

Sigma-Aldrich, 4H-benzo[def]carbazole, printed on Sep. 2 2015 from www.sigmaaldrich.com. "A novel conjugated polymer based on 4H-benzo[def]carbazole backbone for OLED", 2009 Fall Assembly and Symposium (Oct. 8, 2009-Oct. 9, 2009, Gwangju Institute of Science and Technology, Oryong Hall), vol. 34, No. 2, 2009.

* cited by examiner

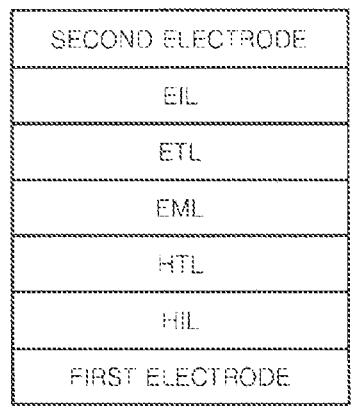

HETEROCYCLIC COMPOUNDS AND ORGANIC LIGHT EMITTING DEVICES INCLUDING THE SAME

CLAIM OF PRIORITY

This application makes reference to, incorporates the same herein, and claims all benefits accruing under 35 U.S.C. §119 from an application for HETEROCYCLIC COMPOUNDS AND ORGANIC LIGHT EMITTING DEVICES INCLUDING THE SAME, earlier filed in the Korean Intellectual Property Office on 5 Nov. 2012 and there duly assigned Serial No. 10-2012-0124467.

BACKGROUND OF THE INVENTION

1. Field of the Invention

The present invention relates to heterocyclic compounds and organic light-emitting devices including the same.

2. Description of the Related Art

Organic light-emitting devices (OLEDs), which are self-emitting devices, have advantages such as wide viewing angles, excellent contrast, quick response, high brightness and excellent driving voltage characteristics and can provide multicolored images.

A typical OLED has a structure including a substrate, and an anode, a hole transport layer (HTL), an emission layer (EML), an electron transport layer (ETL), and a cathode which are sequentially stacked on the substrate. The HTL, the EML, and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons (carriers) recombine in the organic EML to generate excitons. When the excitons drop from an excited state to a ground state, light is emitted.

There is an ongoing demand for a material having improved electrical stability, high charge-transfer or light emission capability, a high glass transition temperature, and no tendency to crystallize, relative to existing unimolecular materials that have been used in OLED applications.

SUMMARY OF THE INVENTION

The present invention provides novel compounds with improved characteristics promoting better OLED performance and high-efficiency, low-voltage, high-luminance and long-lifetime organic light-emitting devices including the novel compounds. The novel compounds have improved electrical characteristics, good charge transporting capabilities, improved light emission capability and a glass transition temperature (Tg) high enough to prevent crystallization. The novel compounds are suitable as hole transporting or injecting materials for fluorescent or phosphorescent devices of any color, or as a red green, blue, or white light-emitting materials.

According to an embodiment of the present invention, there is provided a group of compounds represented by Formula 1 below:

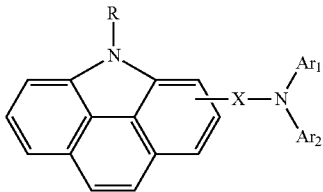

<Formula 1>

In Formula 1,

R may be one of a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C3-C60 cycloalkenyl group, a substituted or unsubstituted C5-C60 aryl group; and a substituted or unsubstituted C6-C60 condensed polycyclic group;

X may be one of a single bond, a substituted or unsubstituted C6-C60 arylene group, a substituted or unsubstituted C6-C60 condensed polycyclic group, and a divalent linking group formed by linking at least two groups selected from the arylene groups and the condensed polycyclic groups; and $Ar_1$ to $Ar_2$ may be each independently one of a substituted or unsubstituted C6-C60 aryl group and a substituted or unsubstituted C6-C60 condensed polycyclic group.

According to another embodiment of the present invention, there is provided an organic light-emitting device including a first electrode, a second electrode, and an organic layer disposed between the first electrode and the second electrode, the organic layer including the compound of Formula 1 described above.

According to another embodiment of the present invention, there is provided a flat panel display device including the above-described organic light-emitting device, the first electrode of the organic light-emitting device being electrically connected to a source electrode or a drain electrode of a thin-film transistor.

BRIEF DESCRIPTION OF THE DRAWINGS

The above and other features and advantages of the present invention will be made more apparent by describing in detail exemplary embodiments thereof with reference to the attached drawings in which:

FIG. 1 is a schematic view of a structure of an organic light-emitting device according to an embodiment of the present invention.

DETAILED DESCRIPTION OF THE INVENTION

As used herein, the term "and/or" includes any and all combinations of one or more of the associated listed items. Expressions such as "at least one of," when preceding a list of elements, modify the entire list of elements and do not modify the individual elements of the list.

According to an embodiment of the present invention, there is provided a compound represented by Formula 1 below:

<Formula 1>

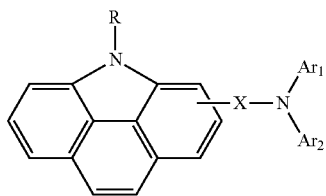

In Formula 1,

R may be one of a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C3-C60 cycloalkenyl group, a substituted or unsubstituted C5-C60 aryl group; and C6-C60 a substituted or unsubstituted condensed polycyclic group;

X may be one of a single bond, a substituted or unsubstituted C6-C60 arylene group, a substituted or unsubstituted C6-C60 condensed polycyclic group, and a divalent linking group formed by linking at least two groups selected from the arylene groups and the condensed polycyclic groups; and $Ar_1$ to $Ar_2$ may be each independently one of a substituted or unsubstituted C6-C60 aryl group and a substituted or unsubstituted C6-C60 condensed polycyclic group.

The compound of Formula 1 may serve as one of a hole injecting material and a hole transporting material for organic light-emitting devices. The compound of Formula 1 has a high glass transition temperature (Tg) or a high melting point due to the inclusion of the heterocyclic ring. Thus, the heterocyclic compound has high heat resistance against Joule's heat generated in an organic layer, between organic layers, or between an organic layer and a metal electrode when light emission occurs, and has high durability in high-temperature environments. An organic light-emitting device manufactured using a heterocyclic compound of Formula 1 may have improved durability when stored or operated.

Substituents in the compound of Formula 1 will now be described in detail.

In some embodiments, in Formula 1, R may be one of the groups represented by Formulae 2a to 2b below:

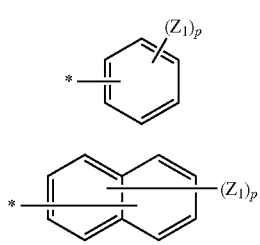

2a

2b

In Formulae 2a to 2b, $Z_1$ may be one of a hydrogen atom, a deuterium atom, a substituted or unsubstituted C1-C20 alkyl group, a substituted or unsubstituted C5-C20 aryl group, a substituted or unsubstituted C6-C20 condensed polycyclic group;

p is an integer from 1 to 7; and * indicates a binding site.

In some other embodiments, in Formula 1, X may be one of the groups represented by Formulae 3a to 3e below:

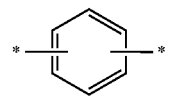

3a

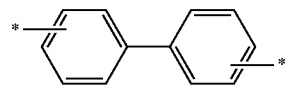

3b

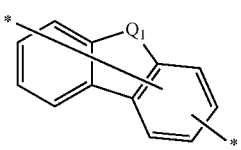

3c

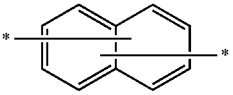

3d

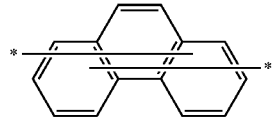

3e

In Formulae 3a to 3e, $Q_1$ may be a linking group represented by one of —$C(R_{30})(R_{31})$—, —S— and —O—;

$R_{30}$ and $R_{31}$ may be each, independently, one of a hydrogen atom, a deuterium atom, a substituted or unsubstituted C1-C20 alkyl group, a substituted or unsubstituted C5-C20 aryl group, and a substituted or unsubstituted C6-C20 condensed polycyclic group; and

* indicates a binding site.

In some other embodiments, in Formula 1, $Ar_1$ and $Ar_2$ may be each independently one of the groups represented by Formulae 4a to 4c below:

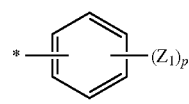

4a

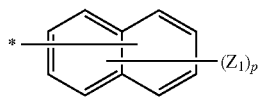

4b

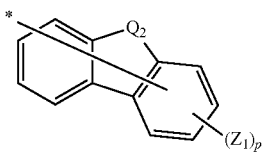

4c

In Formulae 4a to 4c, $Q_2$ may be a linking group represented by one of —$C(R_{30})(R_{31})$— and —$N(R_{32})$—;

$Z_1$, $R_{30}$, $R_{31}$, and $R_{32}$ may be each, independently, one of a hydrogen atom, a deuterium atom, a substituted or unsubstituted C1-C20 alkyl group, a substituted or unsubstituted C5-C20 aryl group, an amino group substituted with a substituted or unsubstituted C5-C20 aryl group and a substituted or unsubstituted C6-C20 condensed polycyclic group;

p is an integer from 1 to 7; and * indicates a binding site.

Hereinafter, substituents described with reference to the formulae will be described in detail. In this regard, the numbers of carbons in substituents are presented only for illustrative purposes and do not limit the characteristics of the substituents.

The unsubstituted C1-C60 alkyl group may be linear or branched. Non-limiting examples of the unsubstituted C1-C60 alkyl group are methyl, ethyl, propyl, isobutyl, sec-butyl, pentyl, iso-amyl, hexyl, heptyl, octyl, nonanyl, and dodecyl. At least one hydrogen atom of the unsubstituted C1-C60 alkyl group may be substituted with a deuterium atom, a halogen group, a C1 to C10 alkyl group, a C1 to C10 alkoxy group, a C2 to C10 alkenyl group, a C2 to C10 alkynyl group, a C6 to C16 aryl group, or an amine group that is substituted with a C6 to C16 aryl group and/or a C6 to C16 heteroaryl group.

The unsubstituted C2-C60 alkenyl group indicates an unsaturated alkyl group having at least one carbon-carbon double bond in the center or at a terminal of the alkyl group. Examples of the alkenyl group are an ethenyl group, a propenyl group, a butenyl group, and the like. At least one hydrogen atom in the unsubstituted alkenyl group may be substituted with a substituent described above in conjunction with the alkyl group.

The unsubstituted C2-C60 alkynyl group indicates an alkyl group having at least one carbon-carbon triple bond in the center or at a terminal of the alkyl group. Non-limiting examples of the unsubstituted C2-C20 alkynyl group are acetylene, propylene, phenylacetylene, naphthylacetylene, isopropylacetylene, t-butylacetylene, and diphenylacetylene. At least one hydrogen atom of the alkoxy group may be substituted with a substituent such as those described above in conjunction with the alkyl group.

The unsubstituted C3-C60 cycloalkyl group indicates a C3-C60 cyclic alkyl group in which at least one hydrogen atom in the cycloalkyl group may be substituted with a substituent described above in conduction with the C1-C60 alkyl group.

The unsubstituted C1-C60 alkoxy group indicates a group having a structure of —OA in which A is an unsubstituted C1-C60 alkyl group as described above. Non-limiting examples of the unsubstituted C1-C60 alkoxy group are a methoxy group, an ethoxy group, a propoxy group, an isopropyloxy group, a butoxy group, and a pentoxy group. At least one hydrogen atom of the alkoxy group may be substituted with a substituent such as those described above in conjunction with the alkyl group.

The unsubstituted C5-C60 aryl group indicates a carbocyclic aromatic system containing at least one ring. At least two rings may be fused to each other or linked to each other by a single bond. The term 'aryl' refers to an aromatic system, such as phenyl, naphthyl, anthracenyl, or dibenzofuryl. At least one hydrogen atom in the aryl group may be substituted with a substituent described above in conjunction with the unsubstituted C1-C60 alkyl group.

Non-limiting examples of the a substituted or unsubstituted C5-C60 aryl group are a phenyl group, a C1-C10 alkylphenyl group (for example, ethylphenyl group), a biphenyl group, a C1-C10 alkyl biphenyl group, a C1-C10 alkoxybiphenyl group, a o-, m-, and p-toryl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a C1-C10 alkylnaphthyl group (for example, methylnaphthyl group), a C1-C10 alkoxynaphthyl group (for example, methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted C3-C60 heteroaryl group used herein includes one, two or three hetero atoms selected from N, O, P and S. At least two rings may be fused to each other or linked to each other by a single bond. Non-limiting examples of the unsubstituted C4-C60 heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolyl group, an isoquinolyl group, and a dibenzothiophene group. In addition, at least one hydrogen atom in the heteroaryl group may be substituted with a substituent described above in conjunction with the unsubstituted C1-C60 alkyl group.

The unsubstituted C5-C60 aryloxy group is a group represented by —OA$_1$ in which A$_1$ may be a C5-C60 aryl group. An example of the aryloxy group is a phenoxy group. At least one hydrogen atom in the aryloxy group may be substituted with a substituent described above in conjunction with the unsubstituted C1-C60 alkyl group.

The unsubstituted C5-C60 arylthio group is a group represented by —SA$_1$ in which A$_1$ may be a C6-C60 aryl group. Non-limiting examples of the arylthio group are a benzenethio group and a naphthylthio group. At least one hydrogen atom in the arylthio group may be substituted with a substituent described above in conjunction with the unsubstituted C1-C60 alkyl group.

The unsubstituted C6-C60 condensed polycyclic group used herein refers to a substituent including at least two rings, at least one aromatic ring and/or at least one non-aromatic ring being fused to each other, or refers to a substituent having an unsaturated group in a ring that may not form a conjugated structure. The unsubstituted C6-C60 condensed polycyclic group is distinct from an aryl group or a heteroaryl group in that it is non-aromatic.

Non-limiting examples of the compound represented by Formula 1 are compounds represented by the following formulae.

1
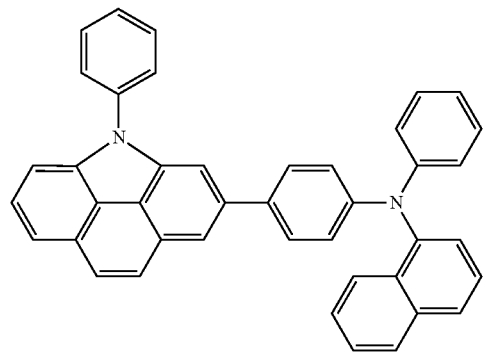
2
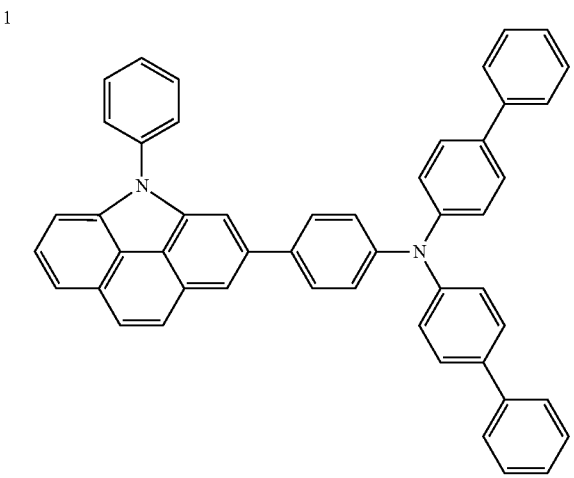
3
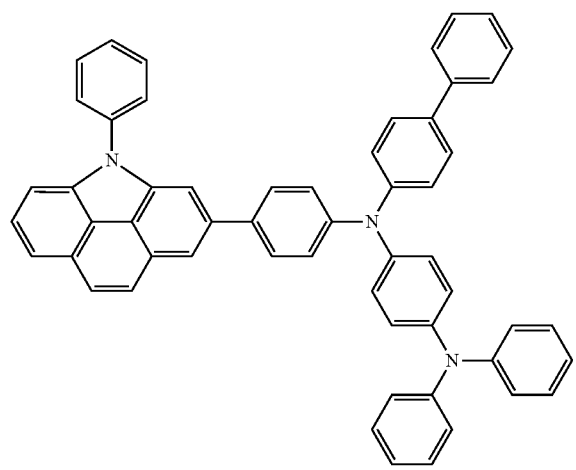
4
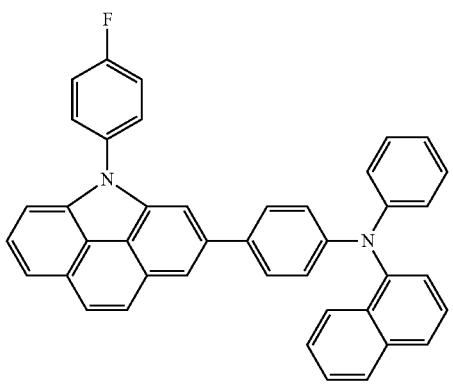
5
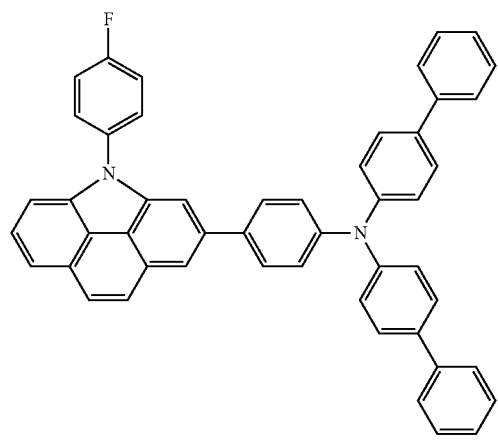
6
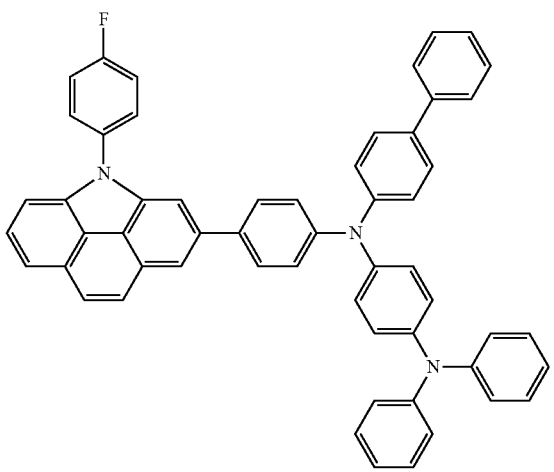

-continued
7
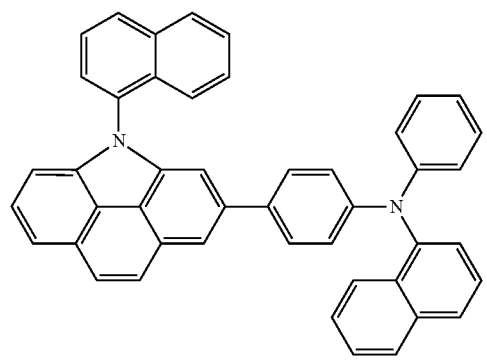
8
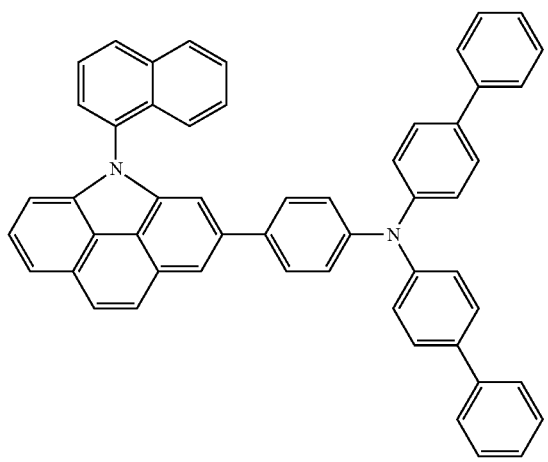
9
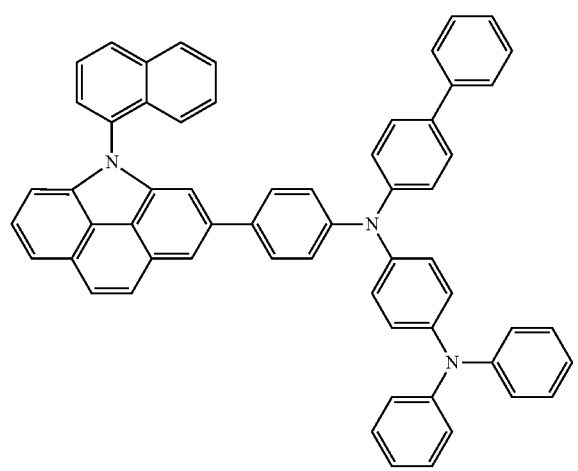
10
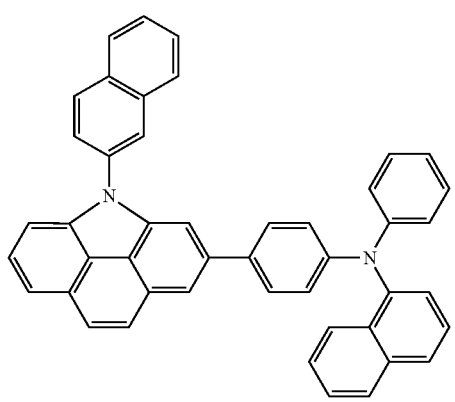
11
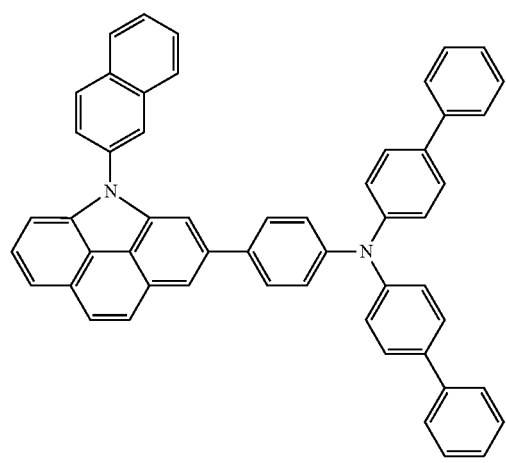
12
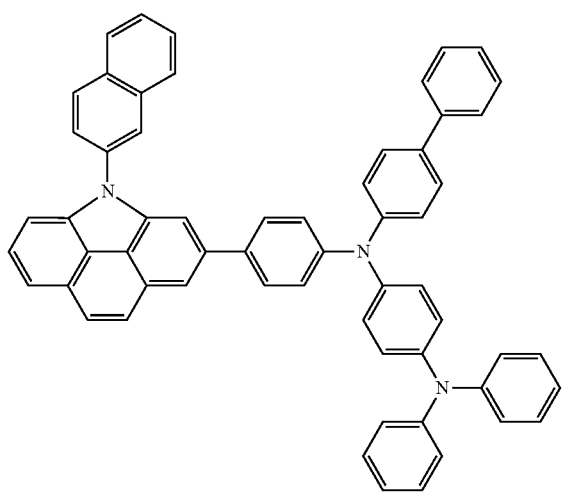

-continued
13
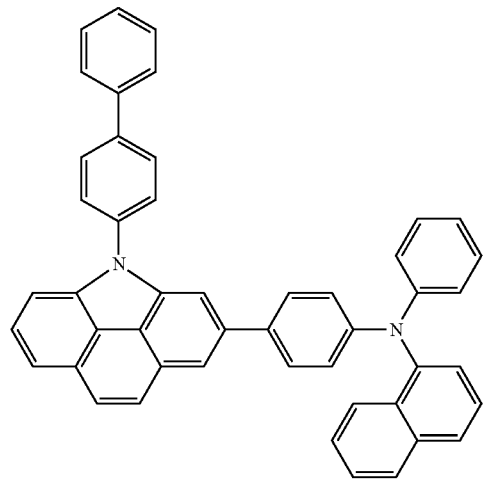
14
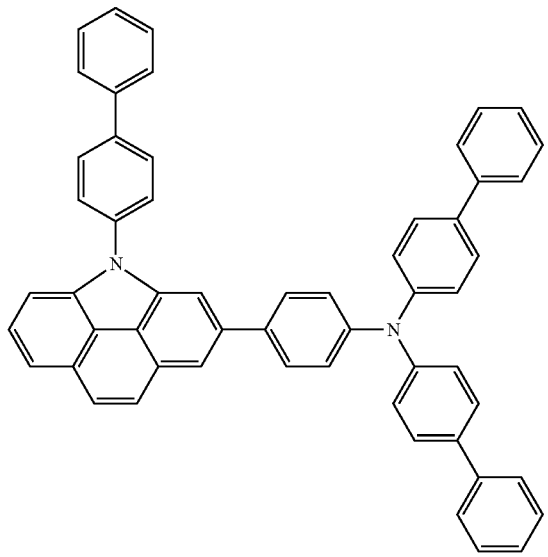
15
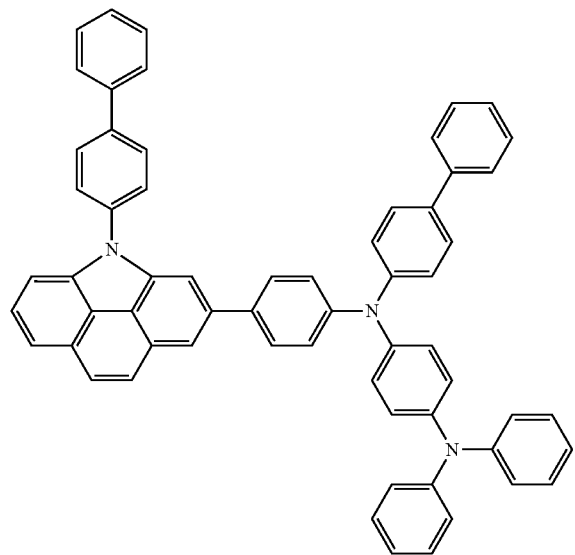
16
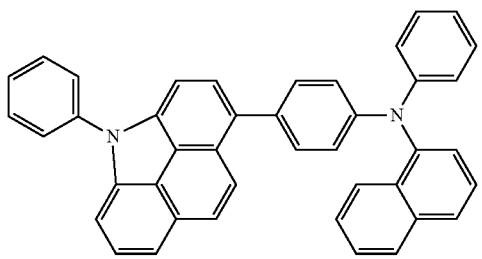
17
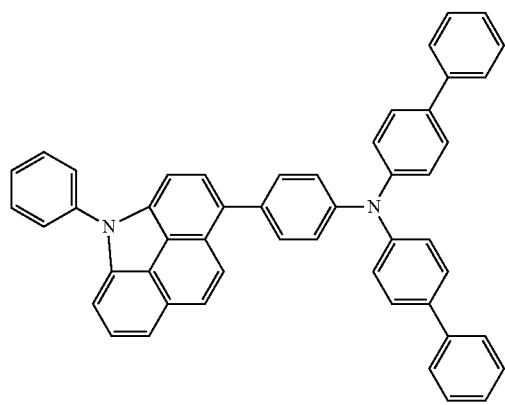
18
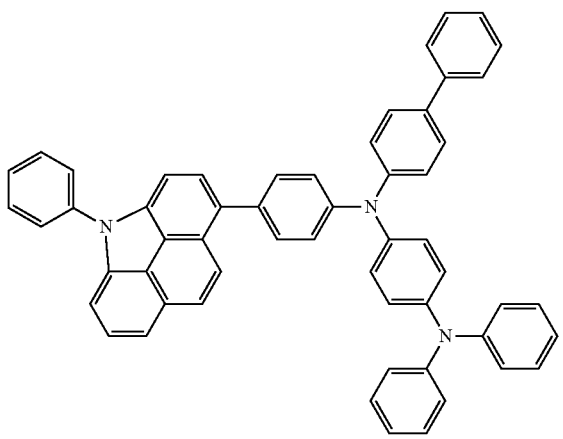

-continued
19
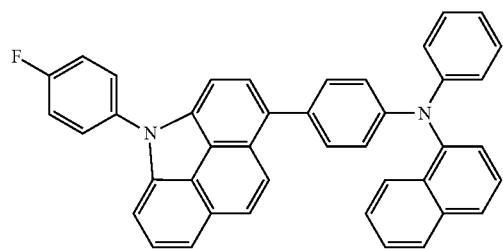
20
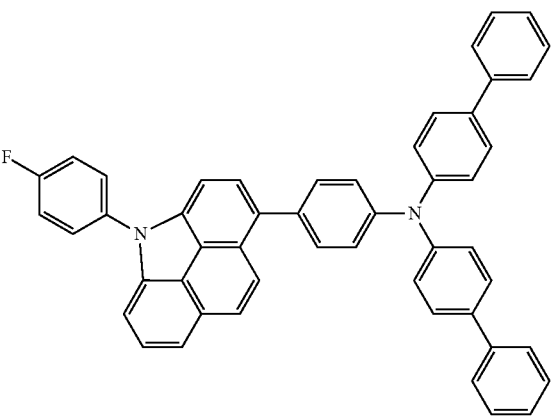
21
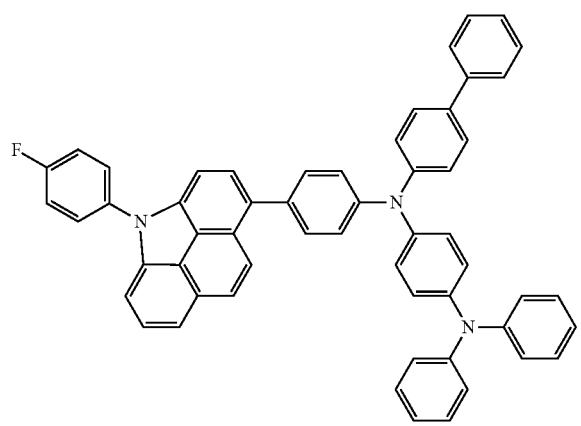
22
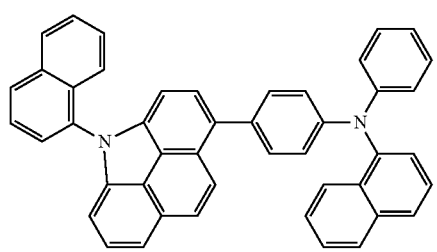
23
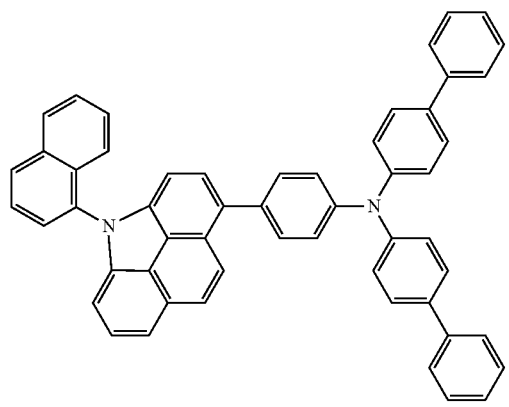
24
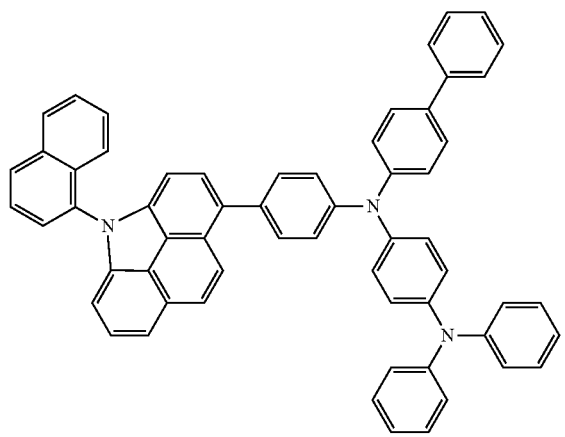

-continued
25
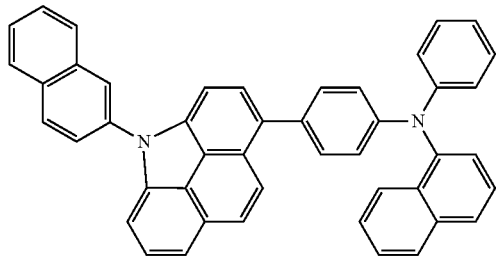
26
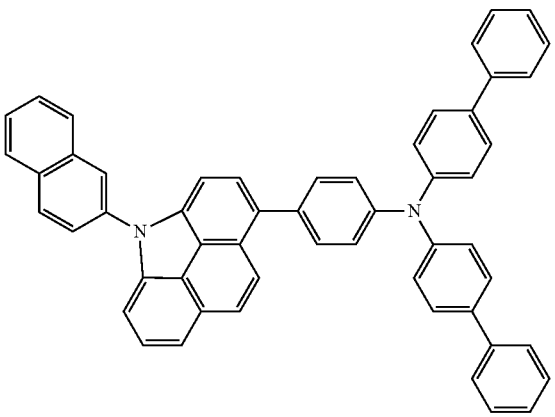
27
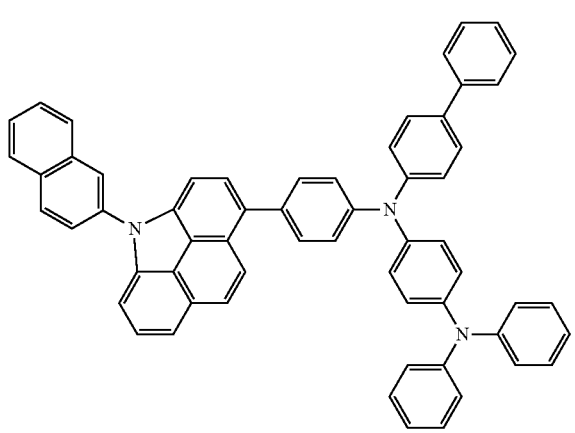
28
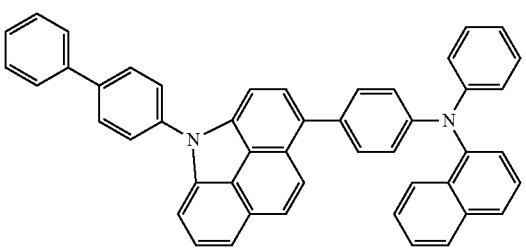
29
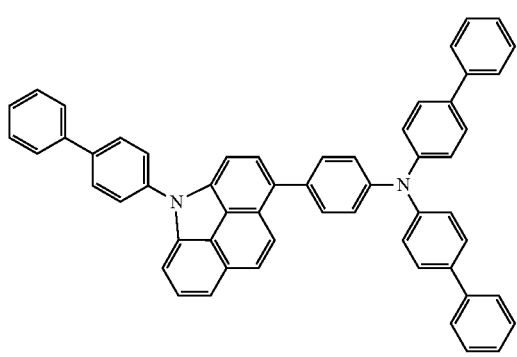
30
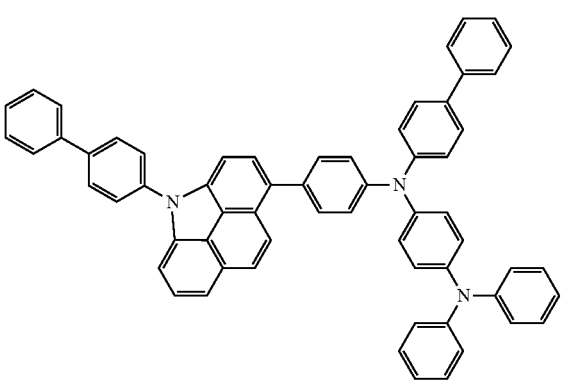
31
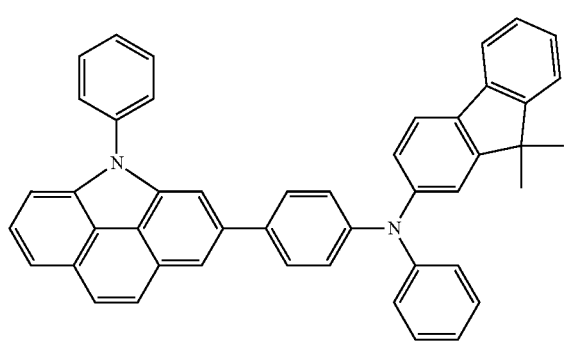
32
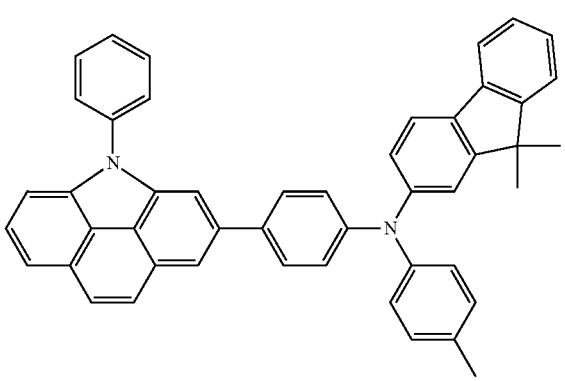

33
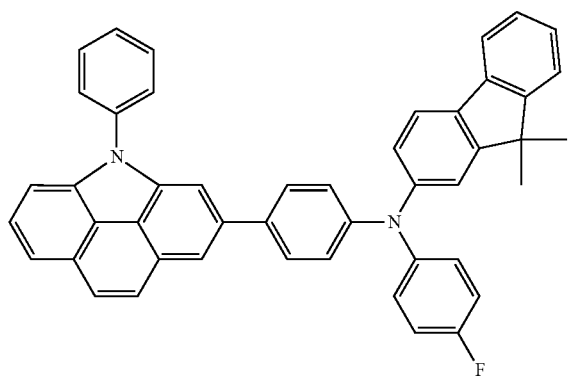
34
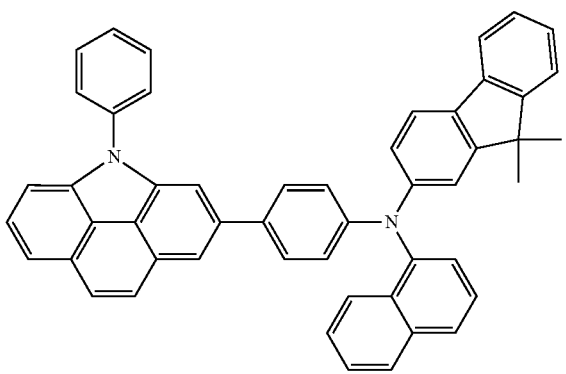
35
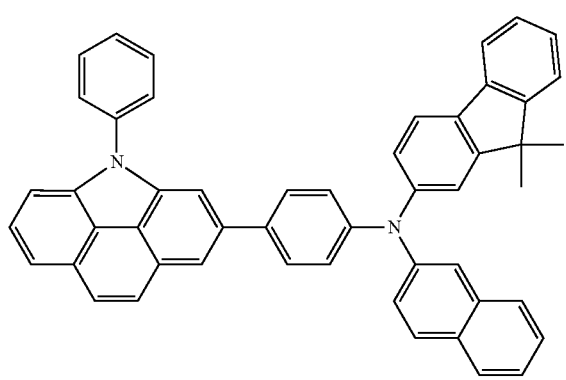
36
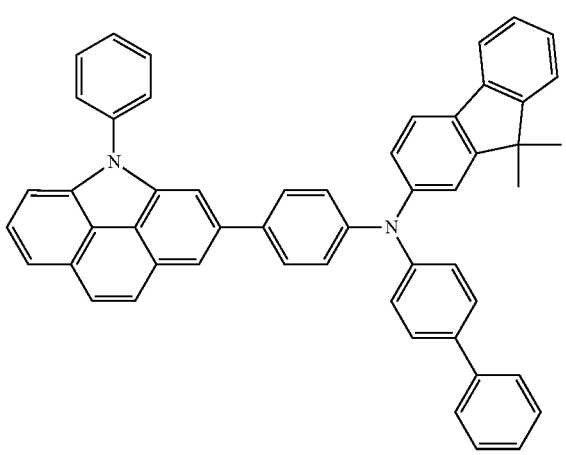
37
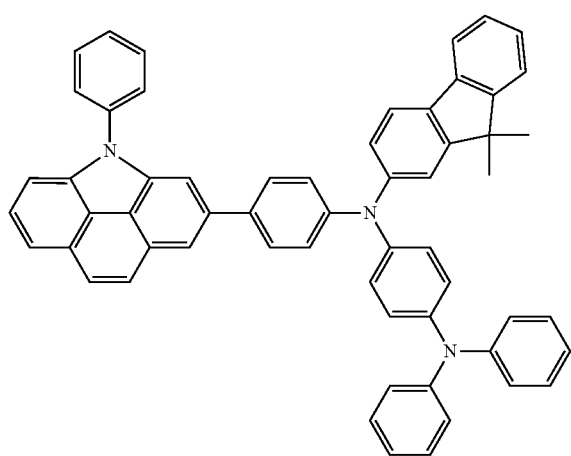
38
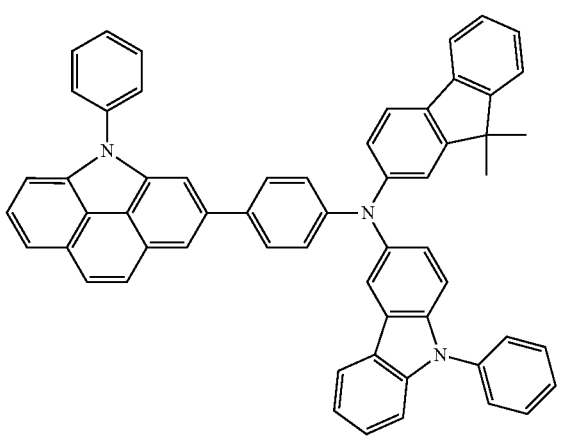

39
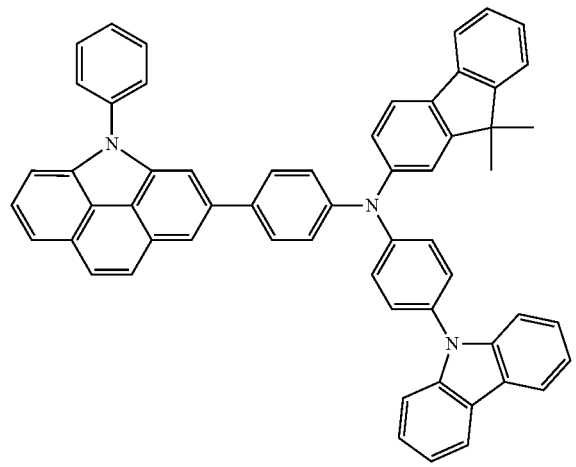
40
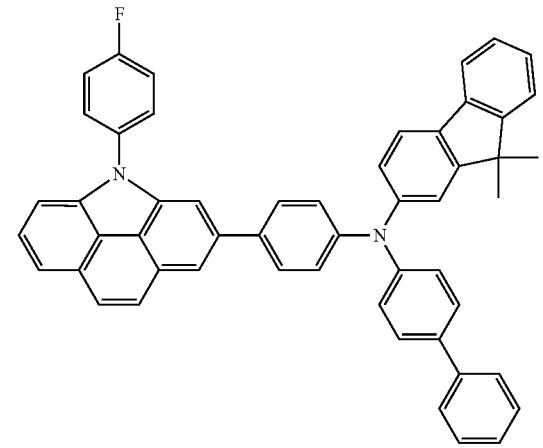
41
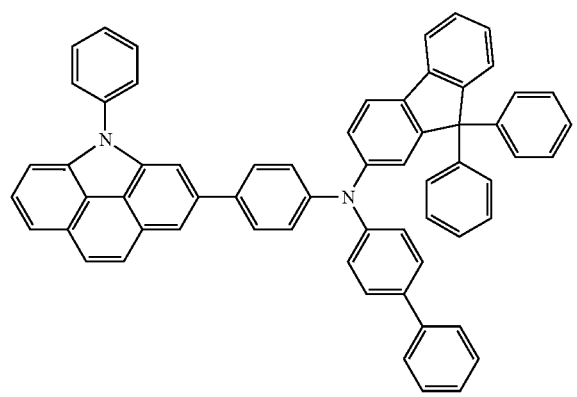
42
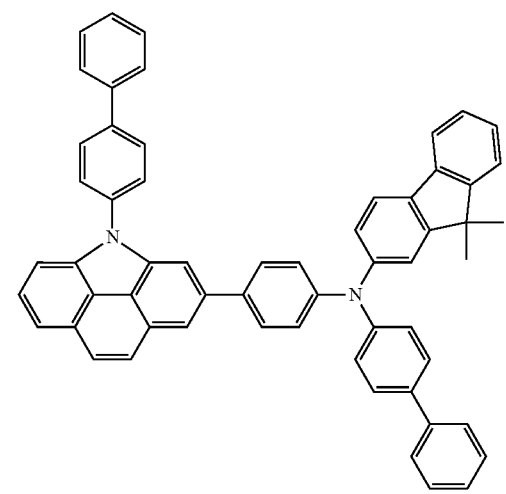
43
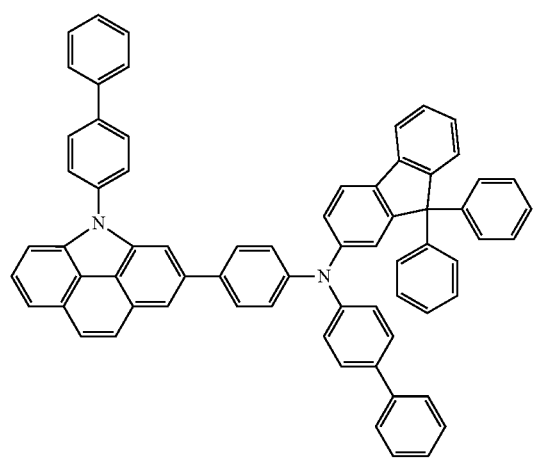
44
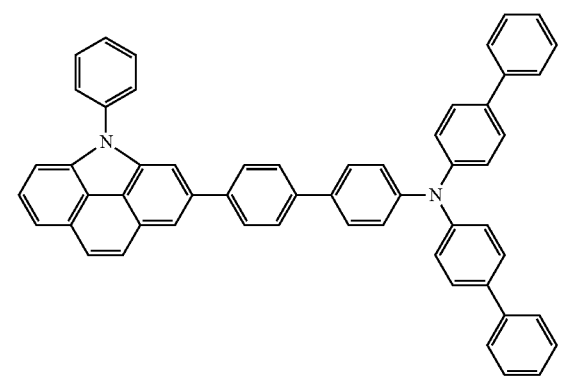

-continued
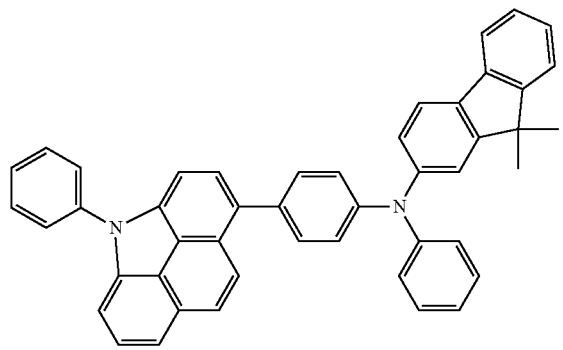
45
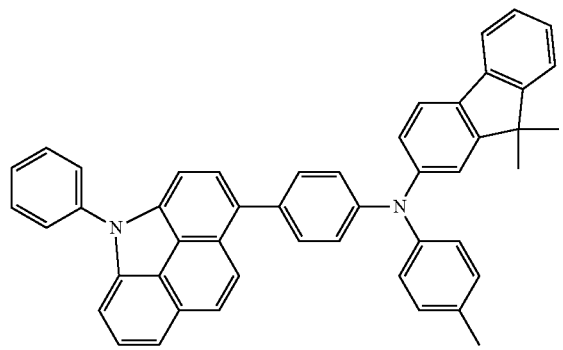
46
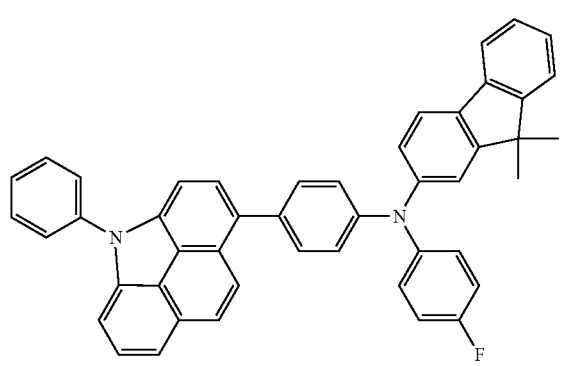
47
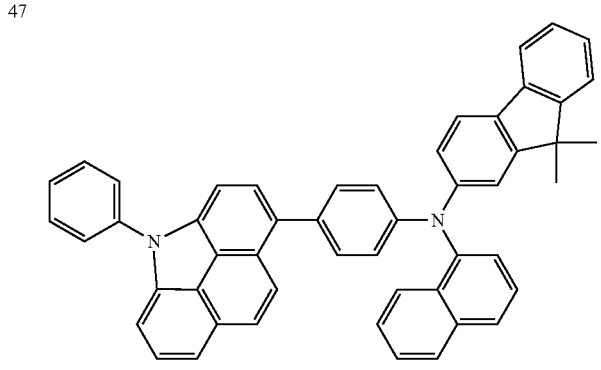
48
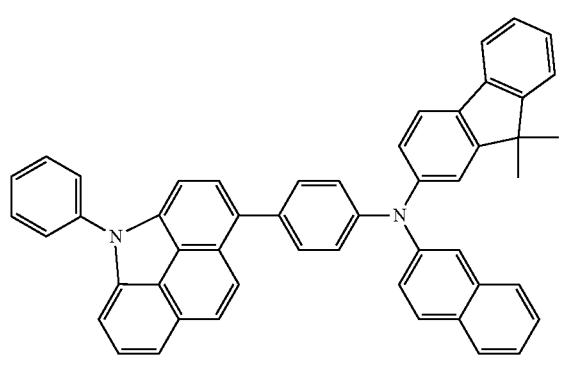
49
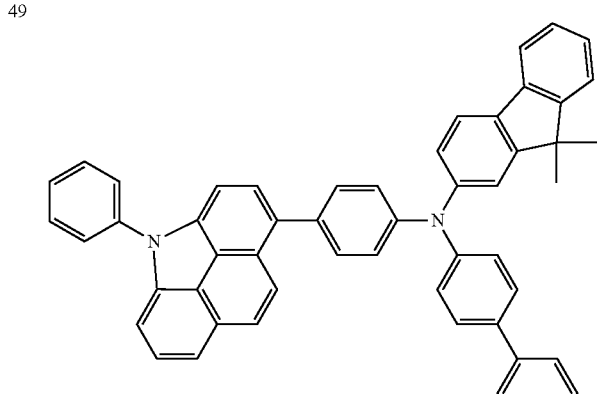
50
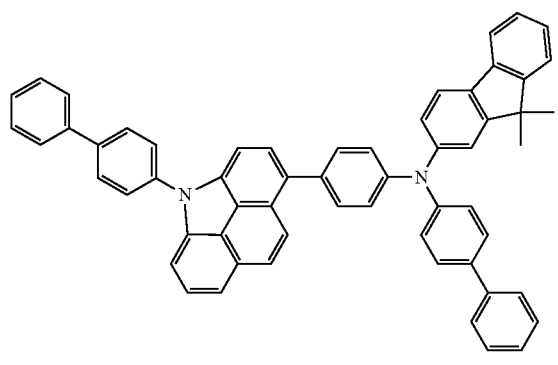
51
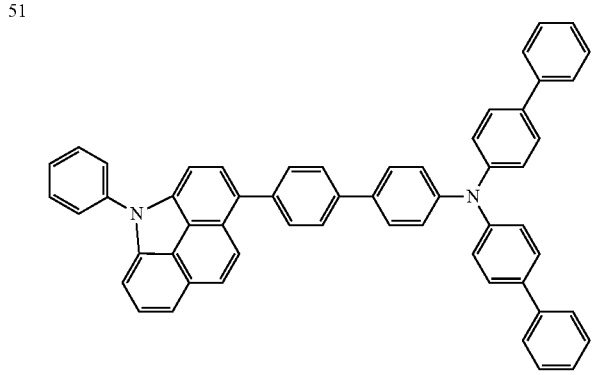
52

-continued
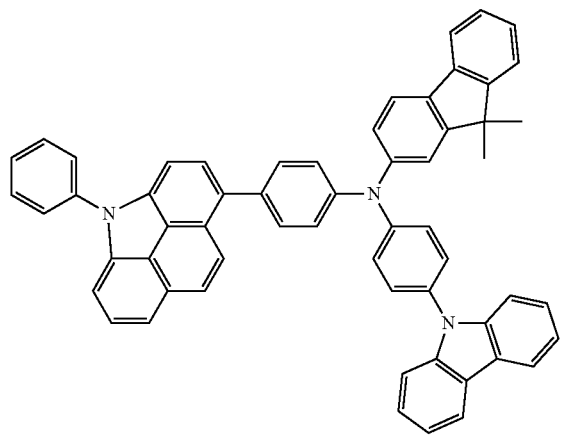
53
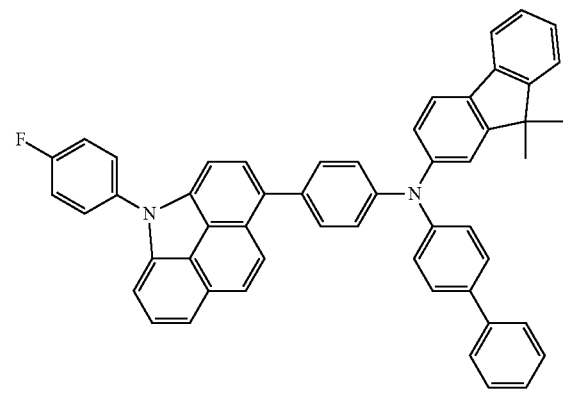
54
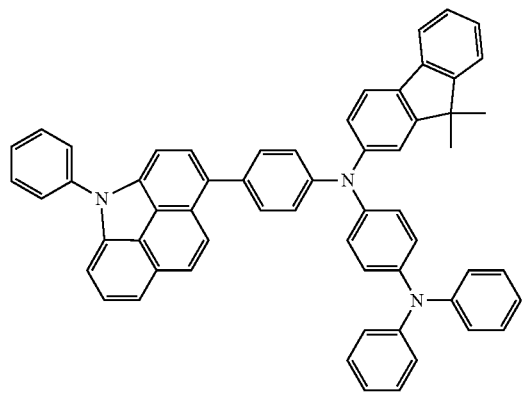
55
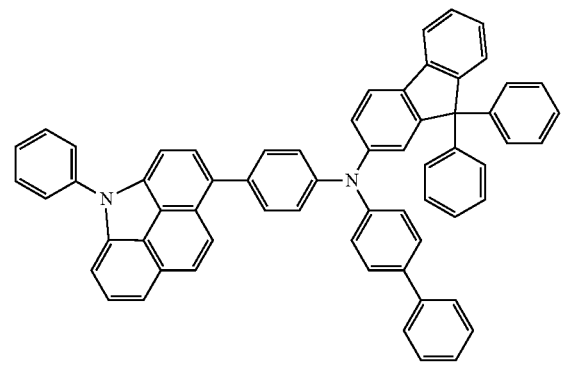
56
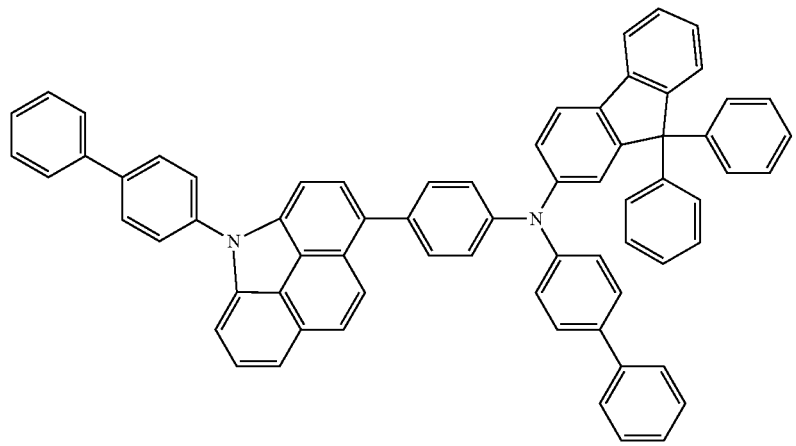
57

-continued
58
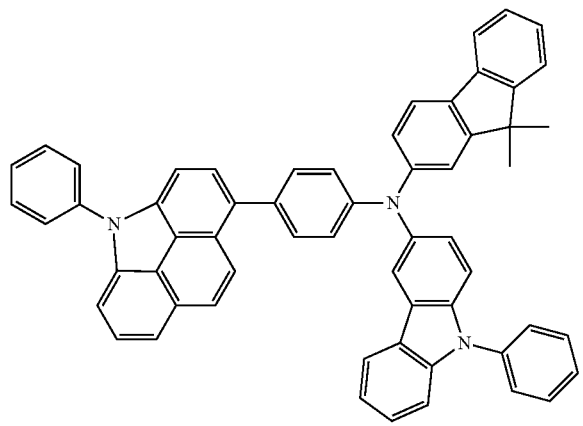
59
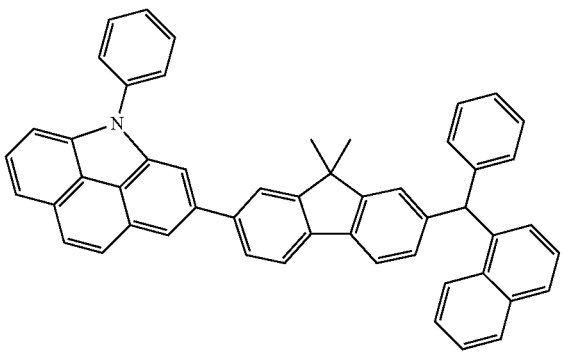
60
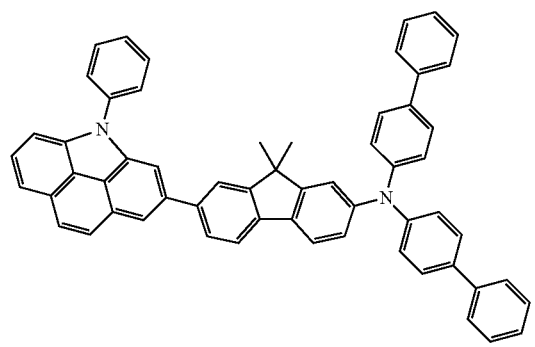
61
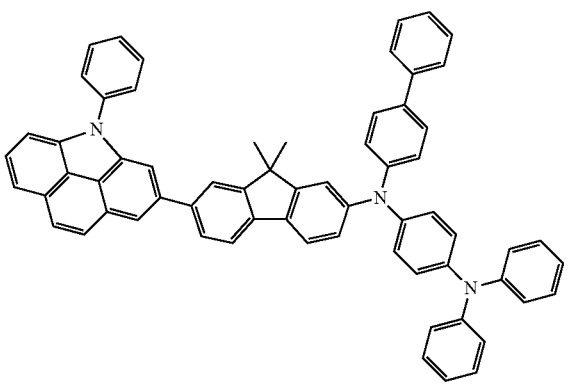
62
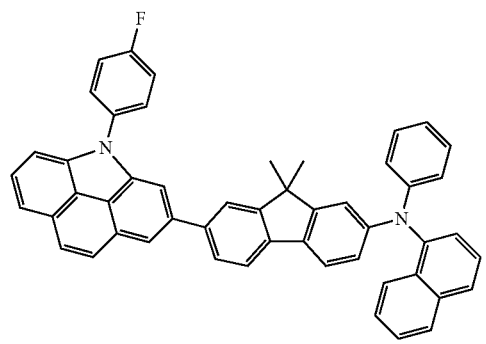
63
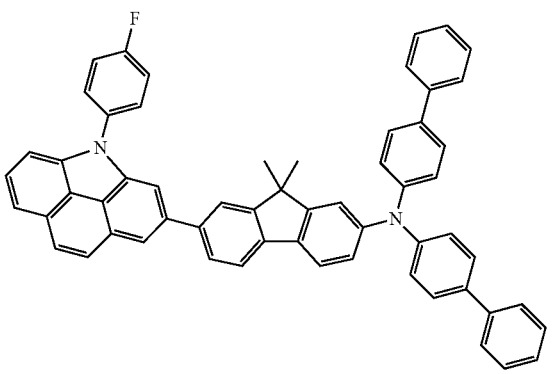
64
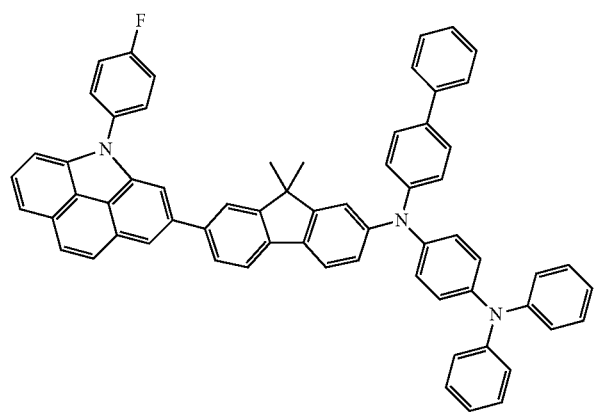
65
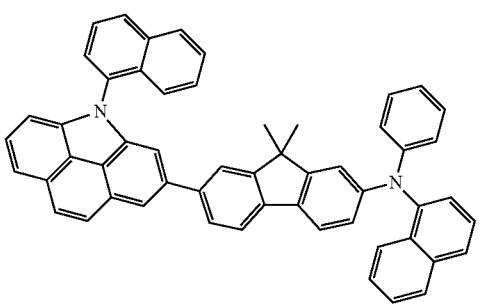

-continued
66
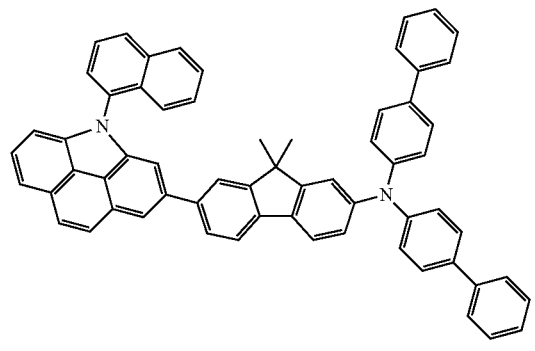
67
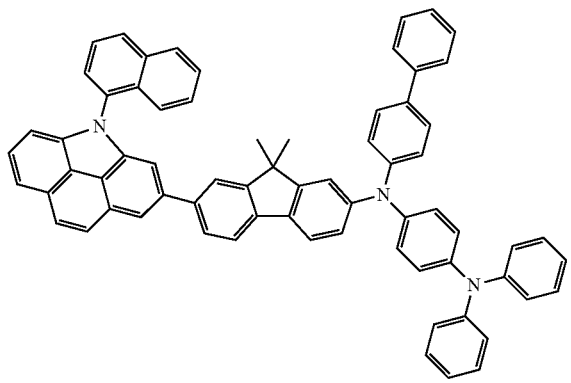
68
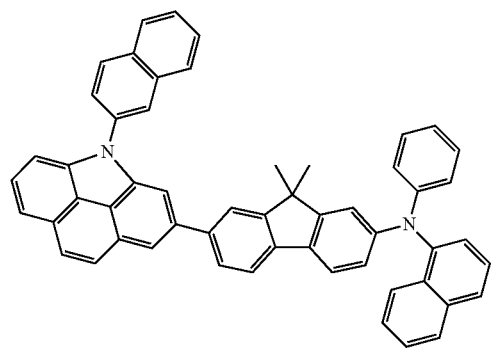
69
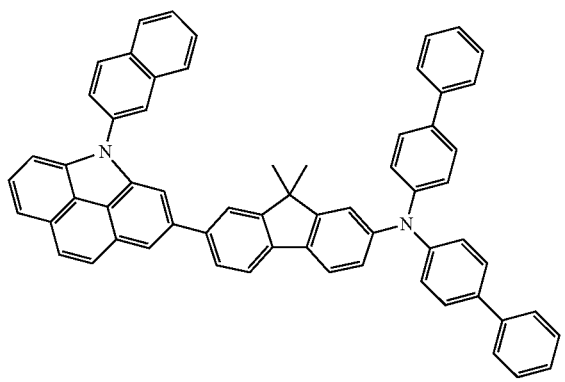
70
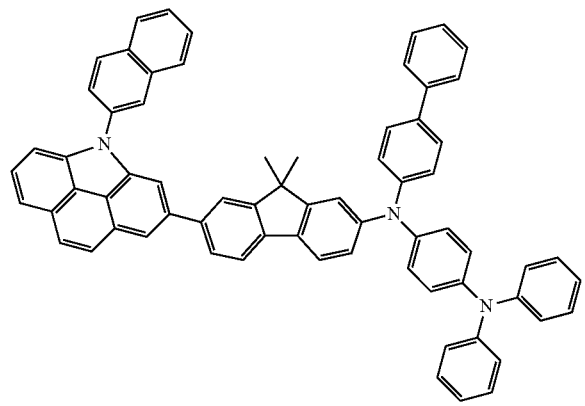
71
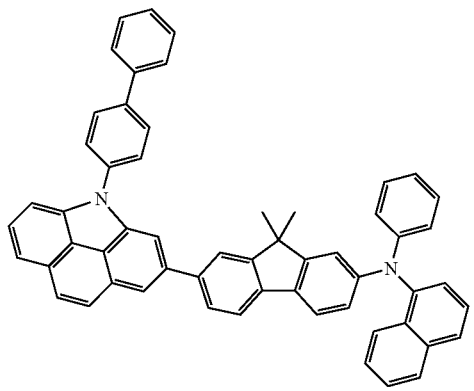

-continued
72
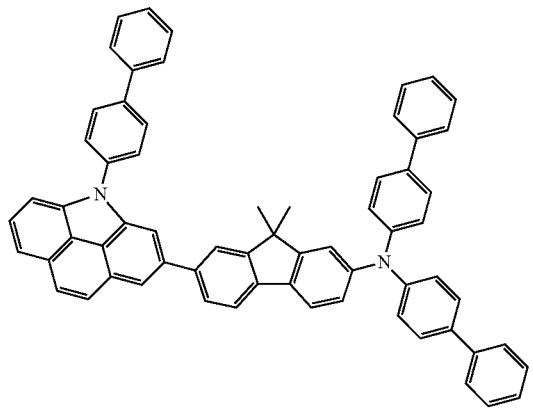
73
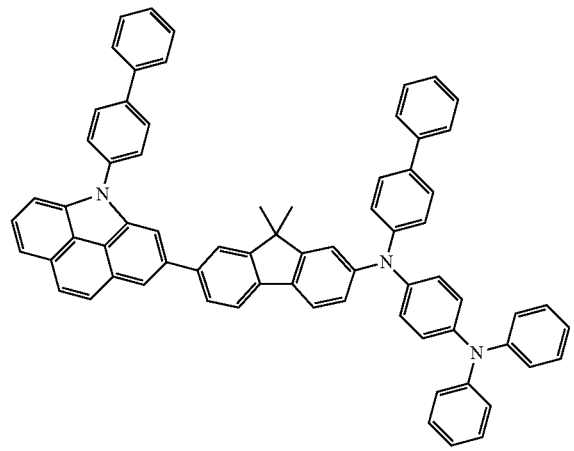
74
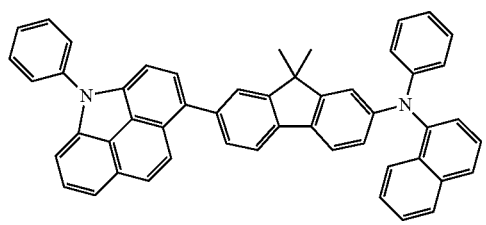
75
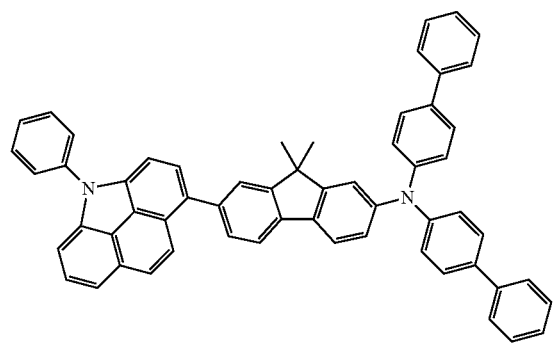
76
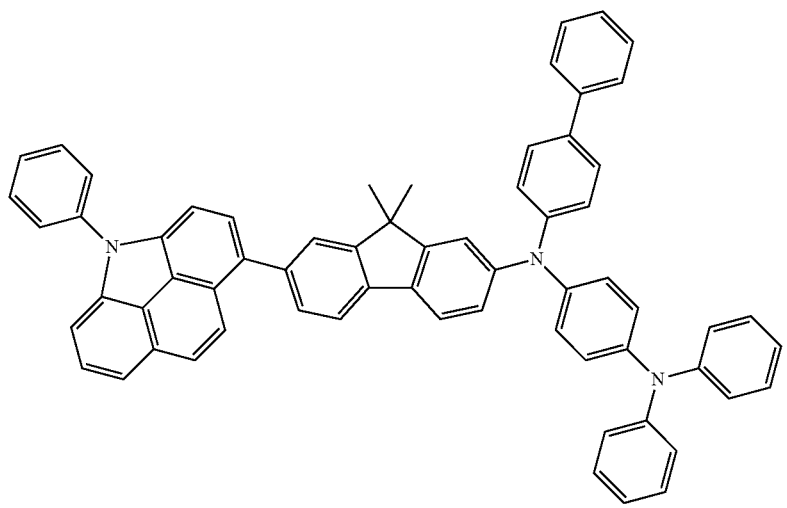

-continued
77
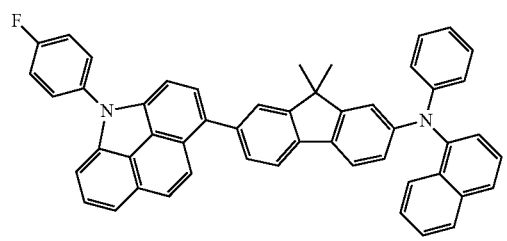
78
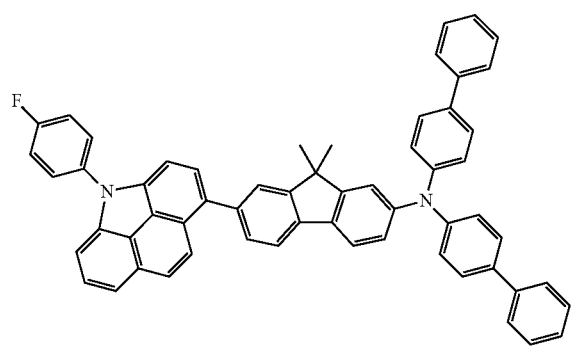
79
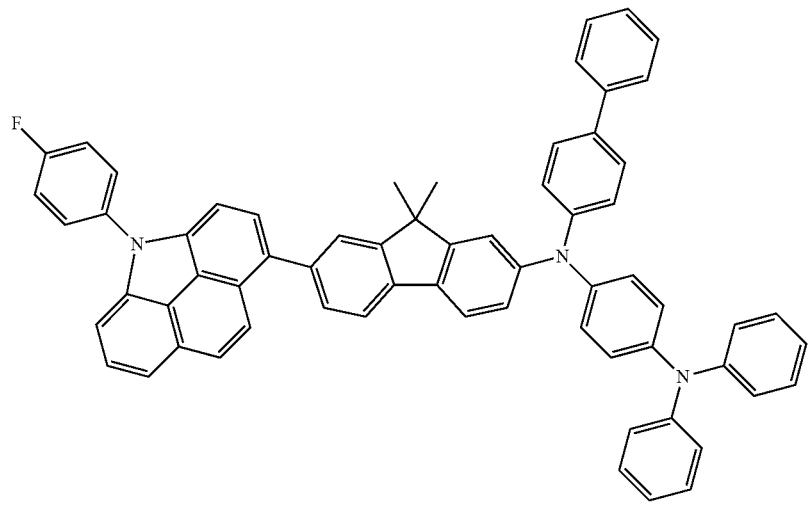
80
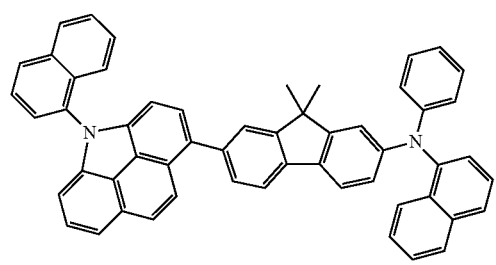
81
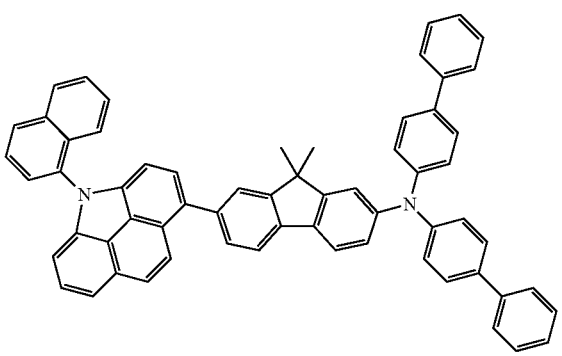
82
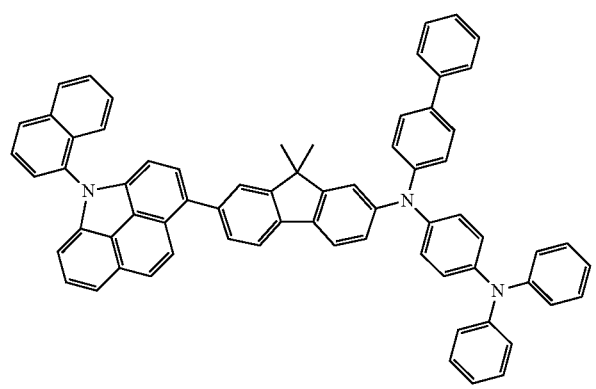
83

84
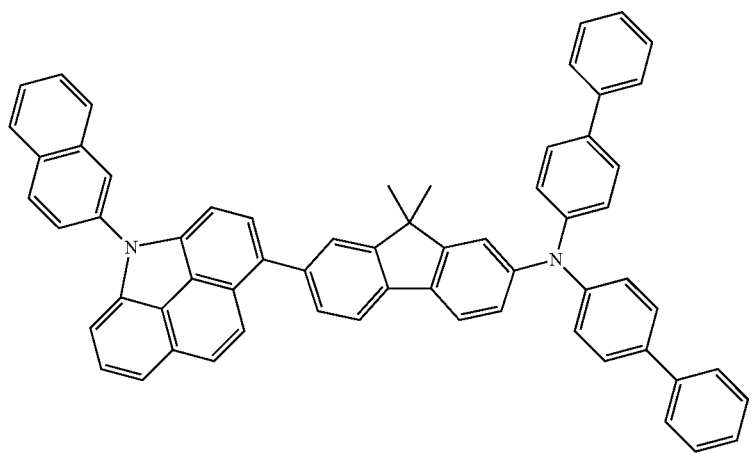
85
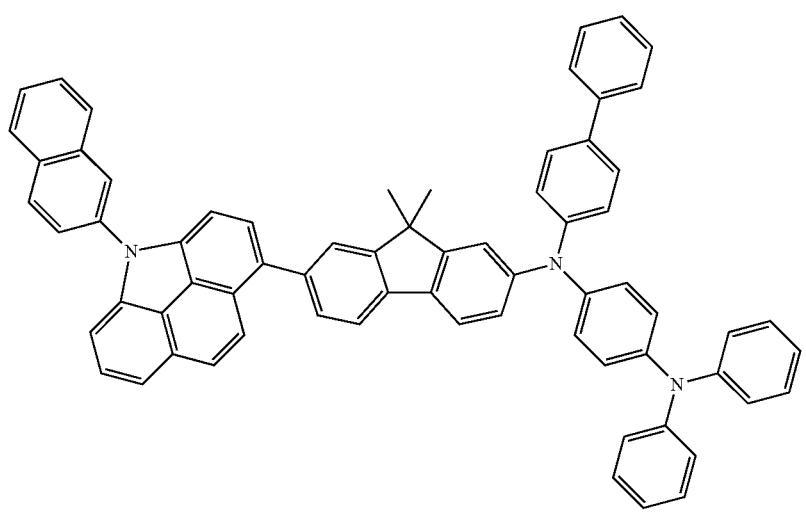
86
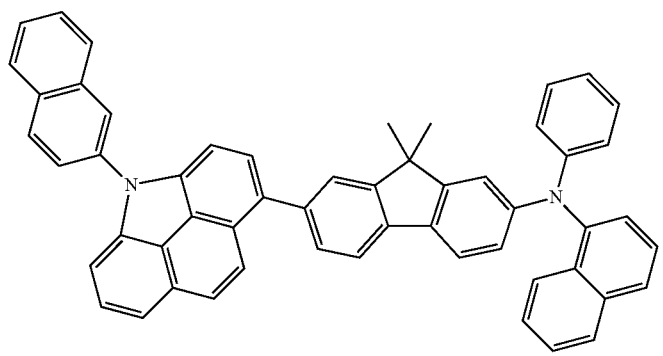

-continued
87
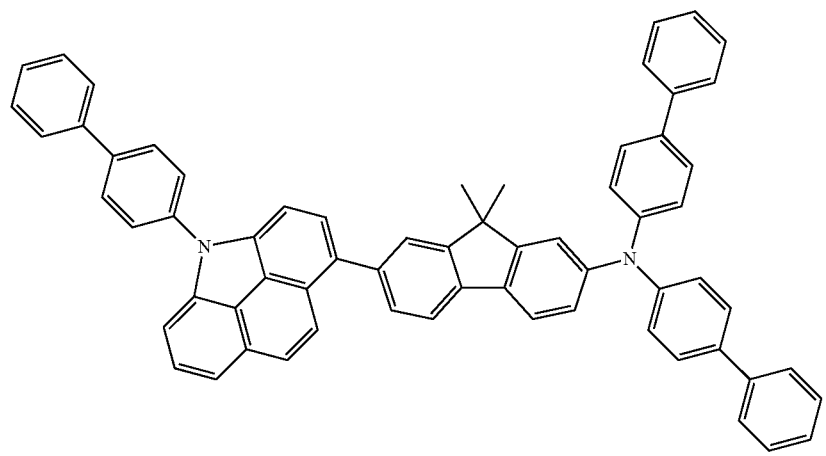
88
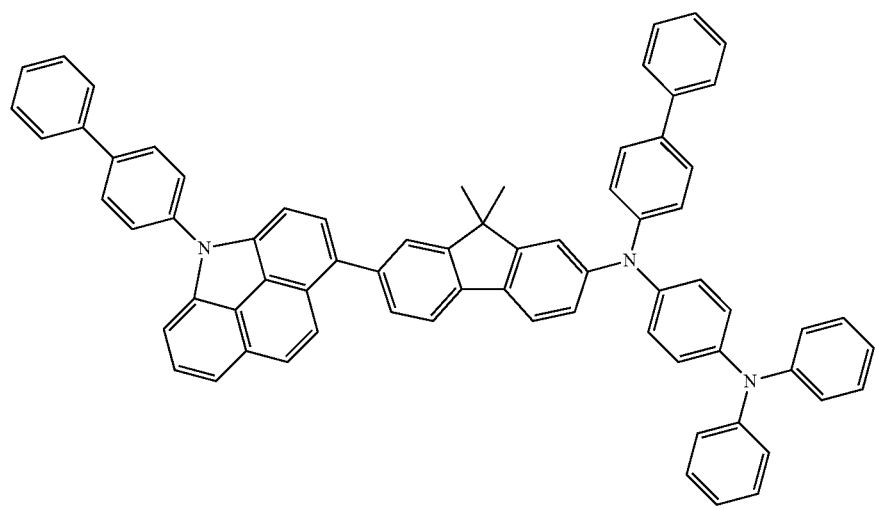
89
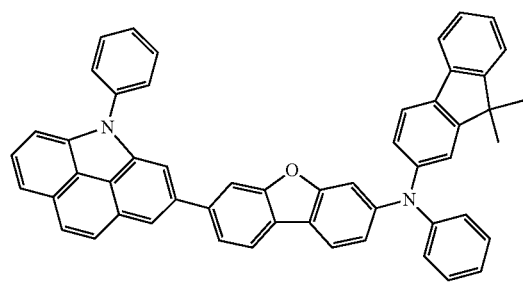
90
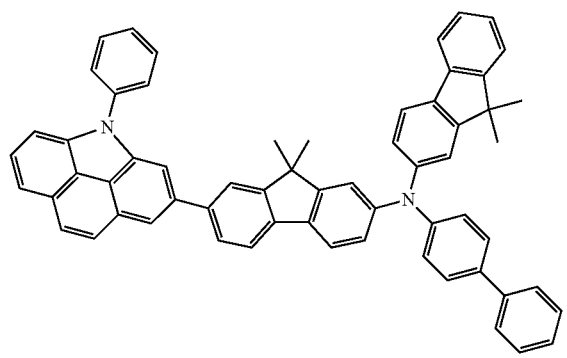

-continued
91
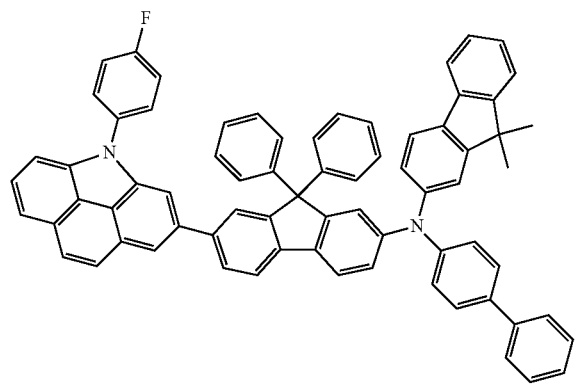
92
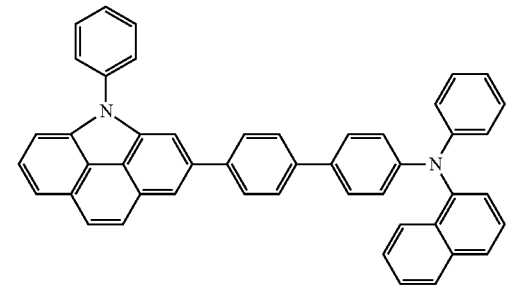
93
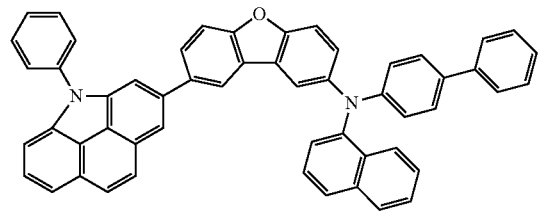
94
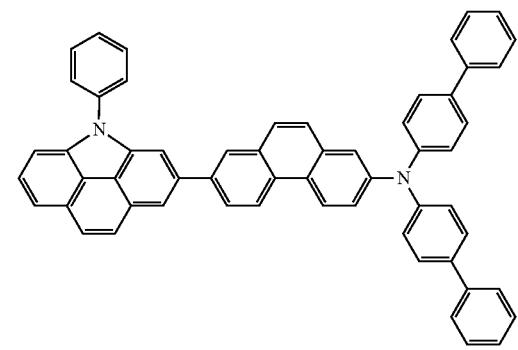
95
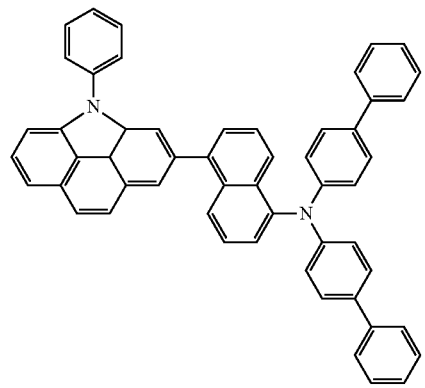
96
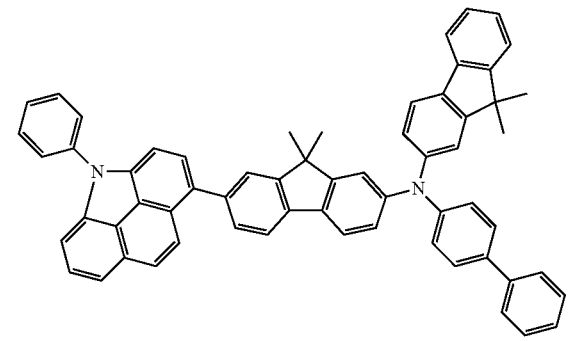
97
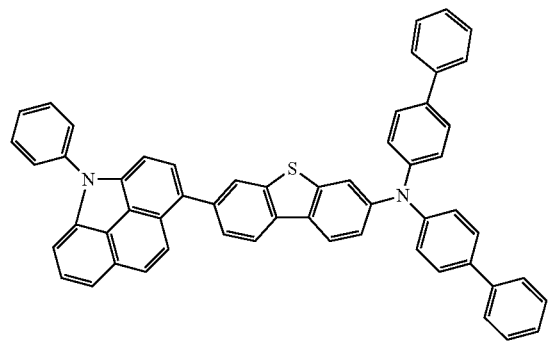
98
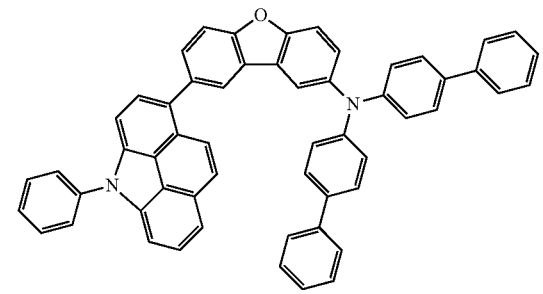

-continued

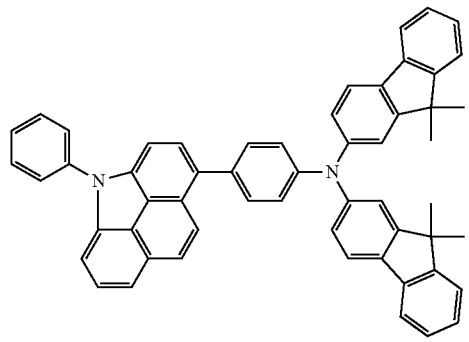
99

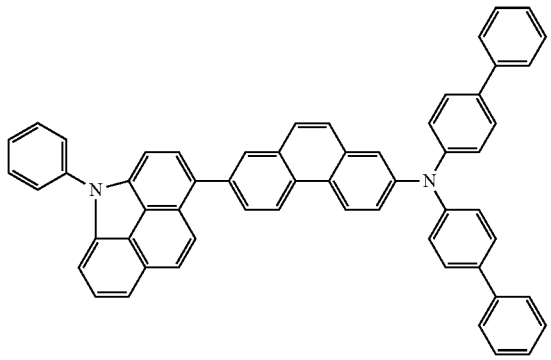
100

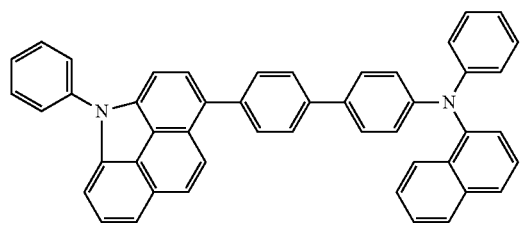
101

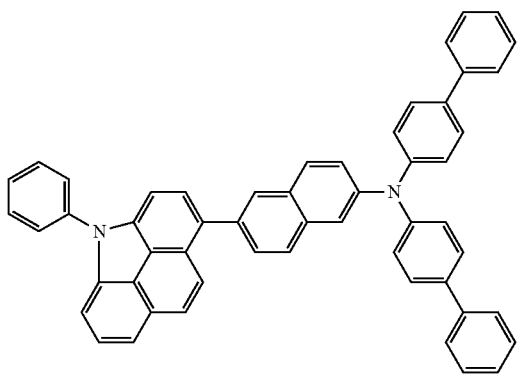
102

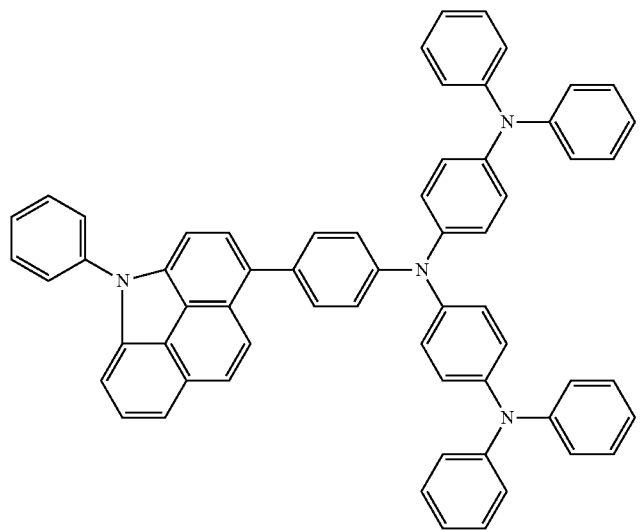
103

Another embodiment of the present invention provides an organic light-emitting device including a first electrode, a second electrode, and an organic layer disposed between the first electrode and the second electrode, the organic layer including a compound of Formula 1 as described above.

The organic layer may include at least one layer selected from among a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer").

In particular, the organic layer may be used as a hole injection layer, a hole transport layer, or a functional layer having both hole injection and transport capabilities.

In some embodiments of the invention, the organic light-emitting device may include at least one of an electron injection layer, an electron transport layer, an emission layer, a hole injection layer, a hole transport layer, and a functional layer having both hole injection and transport capabilities; the hole injection layer, the hole transport layer, or the functional layer having both hole injection and hole transport capabilities may include a compound of Formula 1 above; and the emission layer may include one of an anthracene-based compound, an arylamine-based compound and a styryl-based compound.

In some other embodiments of the invention, the organic light-emitting device may include at least one of an electron injection layer, an electron transport layer, an emission layer, a hole injection layer, a hole transport layer, and a functional layer having both hole injection and transport capabilities; at least one of a red emission layer, a green emission layer, a blue emission layer, and a white emission layer of the emission layer may include a phosphorescent compound; and at least one of the hole injection layer, the hole transport layer, and the functional layer having both hole injection and hole transport capabilities may further include a charge-generating material in addition to a compound of the present invention. In some embodiments, the charge-generating material may be a p-dopant, and the p-dopant may be one of a quinine derivative, a metal oxide, and a cyano group-containing compound.

In some embodiments of the invention, the organic layer may include an electron transport layer, and the electron transport layer may include an electron-transporting organic compound and a metal complex. The metal complex may be a lithium (Li) complex.

The term "organic layer" as used herein refers to a single layer and/or a plurality of layers disposed between the first and second electrodes of the organic light-emitting device.

The organic layer may include an emission layer, and the emission layer may include a compound of Formula 1 as described above. The organic layer may include at least one of a hole injection layer, a hole transport layer, and a functional layer having both hole injection and hole transport capabilities (hereinafter, "H-functional layer"); and at least one of the hole injection layer, the hole transport layer, and the functional layer having both hole injection and hole transport capabilities may include a compound of Formula 1.

FIG. 1 is a schematic sectional view of an organic light-emitting device according to an embodiment of the present invention. Hereinafter, a structure of an organic light-emitting device according to an embodiment of the present invention and a method of manufacturing the same will be described with reference to FIG. 1.

A substrate (not shown) may be any substrate that is used in existing organic light emitting devices. In some embodiments of the invention, the substrate may be one of a glass substrate and a transparent plastic substrate with strong mechanical strength, thermal stability, transparency, surface smoothness, ease of handling and water resistance.

The first electrode may be formed by depositing or sputtering a first electrode-forming material on the substrate. When the first electrode is an anode, a material having a high work function may be used as the first electrode-forming material in order to facilitate hole injection. The first electrode may be a reflective electrode or a transmission electrode. Transparent and conductive materials such as indium tin oxide (ITO), indium zinc oxide (IZO), $SnO_2$, and ZnO may be used to form the first electrode. The first electrode may be formed as a reflective electrode using one of magnesium (Mg), aluminum (Al), aluminum-lithium (Al—Li), calcium (Ca), magnesium-indium (Mg—In), magnesium-silver (Mg—Ag), and the like.

The first electrode may have one of a single-layer structure and a multi-layer structure including at least two layers. For example, the first electrode may have a three-layered structure of ITO/Ag/ITO, but is not limited thereto.

An organic layer may be disposed on the first electrode.

The organic layer may include at least one of a hole injection layer (HIL), a hole transport layer (HTL), a buffer layer (not shown), an emission layer (EML), an electron transport layer (ETL) and an electron injection layer (EIL).

The HIL may be formed on the first electrode by one of vacuum deposition, spin coating, casting, Langmuir-Blodgett (LB) deposition, and the like.

When the HIL is formed using vacuum deposition, vacuum deposition conditions may vary according to the compound that is used to form the HIL and the desired structure and thermal properties of the HIL to be formed. For example, vacuum deposition may be performed at a temperature of from about 100° C. to about 500° C., a pressure of from about $10^{-8}$ torr to about $10^{-3}$ torr, and a deposition rate of from about 0.01 to about 100 Å/sec. However, the deposition conditions are not limited thereto.

When the HIL is formed using spin coating, the coating conditions may vary according to the material that is used to form the HIL and the desired structure and thermal properties of the HIL to be formed. For example, the coating rate may be in the range of from about 2000 rpm to about 5000 rpm, and a temperature at which heat treatment is performed to remove a solvent after coating may be in the range of from about 80° C. to about 200° C. However, the coating conditions are not limited thereto.

The HIL may be formed of any material that is commonly used to form a HIL, in addition to the compound of Formula 1. Non-limiting examples of the material that can be used to form the HIL are N,N'-bis[4-(di-m-tolylamino)phenyl]-N,N'-diphenylbenzidine (DNTPD), a phthalocyanine compound such as copper phthalocyanine, 4,4',4''-tris(N-3-methylphenyl-N-phenylamino)triphenylamine (m-MTDATA), N,N'-di(1-naphthyl)-N,N'-diphenylbenzidine (NPB), 4,4',4''-tris(diphenylamino)triphenylamine (TDATA), 4,4',4''-tris[N-(2-naphthyl)-N-phenyl-amino]triphenylamine (2T-NATA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate) (PANI/PSS).

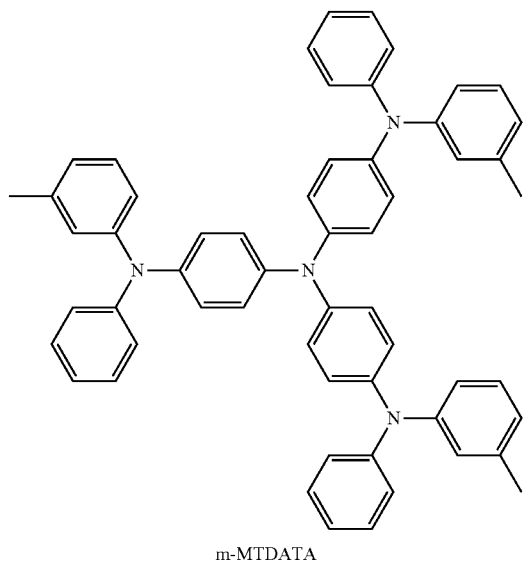

m-MTDATA

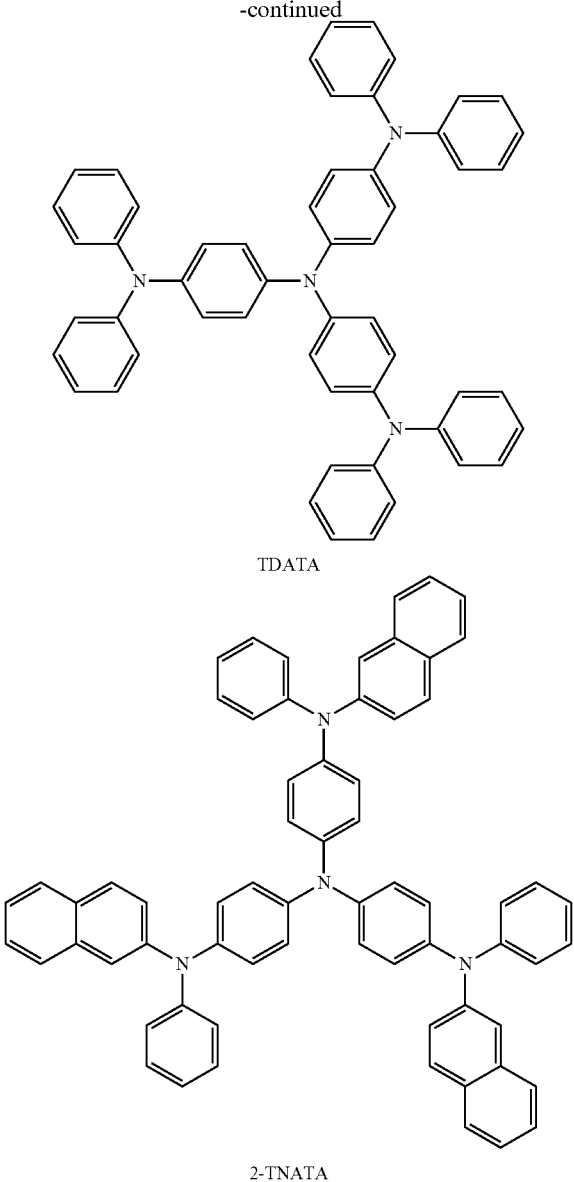

TDATA

2-TNATA

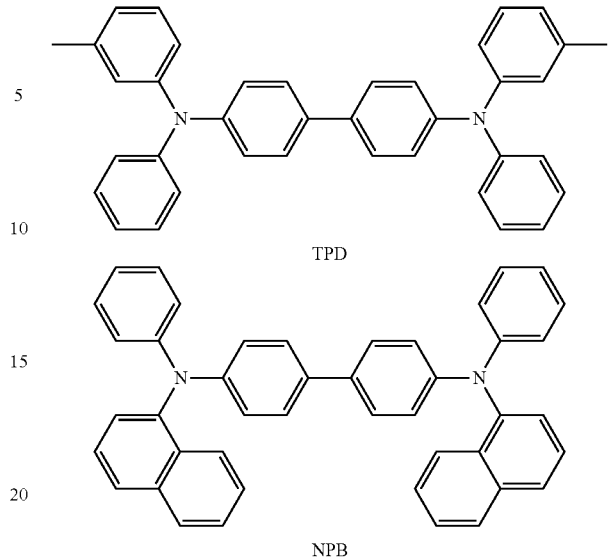

TPD

NPB

The thickness of the HTL may be from about 50 Å to about 2000 Å, and, in some embodiments, from about 100 Å to about 1500 Å. When the thickness of the HTL is within these ranges, the HTL may have good hole transporting ability without imparting a substantial increase in driving voltage to the OLED.

The H-functional layer (having both hole injection and hole transport capabilities) may contain at least one material from each group, including the group of hole injection layer materials and the group of hole transport layer materials. The thickness of the H-functional layer may be from about 500 Å to about 10,000 Å, and, in some embodiments, may be from about 100 Å to about 1,000 Å. When the thickness of the H-functional layer is within these ranges, the H-functional layer may have good hole injection and transport capabilities without imparting a substantial increase in driving voltage to the OLED.

In some embodiments, at least one of the HIL, HTL, and H-functional layer may include at least one of a compound of Formula 300 below and a compound of Formula 350 below:

The thickness of the HIL may be from about 100 Å to about 10000 Å, and in some embodiments, may be from about 100 Å to about 1000 Å. When the thickness of the HIL is within these ranges, the HIL may have good hole injecting ability without imparting a substantial increase in driving voltage of the OLED.

Then, a HTL may be formed on the HIL by using one of vacuum deposition, spin coating, casting, Langmuir-Blodgett (LB) deposition, and the like. When the HTL is formed using one of vacuum deposition and spin coating, the conditions for deposition and coating may be similar to those for the formation of the HIL, though the conditions for the deposition and coating may vary according to the material that is used to form the HTL.

The HTL may be formed of a material selected from a compound of Formula 1 and other hole transporting materials. Non-limiting examples of suitable known HTL forming materials are carbazole derivatives, such as one of N-phenyl-carbazole, polyvinylcarbazole, N,N-bis(3-methylphenyl)-N, N-diphenyl-[1,1-biphenyl]-4,4'-diamine (TPD), 4,4',4''-tris (N-carbazolyl)triphenylamine (TCTA), and N,N'-di(1-naphthyl)-N,N'-diphenylbenzidine (NPB).

<Formula 300>

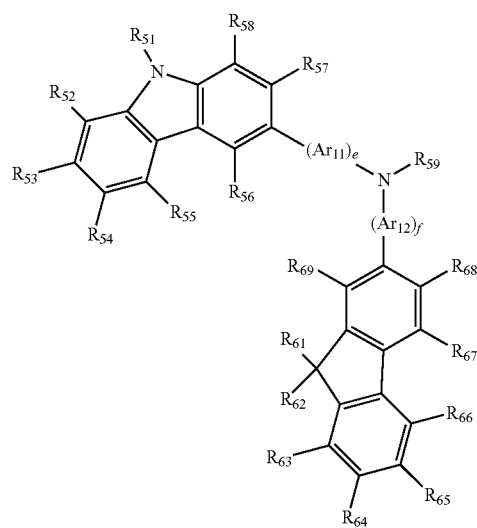

<Formula 350>

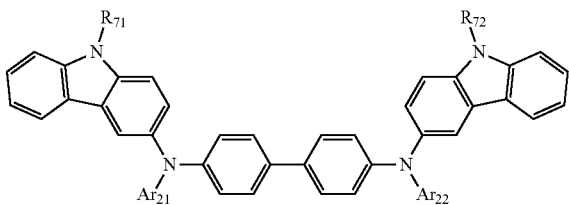

In Formulae 300 and 350, $Ar_{11}$ and $Ar_{12}$ may be each independently a substituted or unsubstituted $C_5$-$C_{60}$ arylene group, and $Ar_{21}$ and $Ar_{22}$ may be each independently a substituted or unsubstituted $C_5$-$C_{60}$ aryl group.

In Formula 300, e and f may be each independently an integer from 0 to 5, for example, may be 0, 1, or 2. In a non-limiting embodiment of the invention, e may be 1, and f may be 0.

In Formulae 300 and 350 above, $R_{51}$ to $R_{58}$, $R_{61}$ to $R_{69}$, and $R_{71}$ to $R_{72}$ may be each independently selected from a hydrogen atom, a deuterium atom, a halogen atom, a hydroxyl group, a cyano group, a nitro group, an amino group, an amidino group, a hydrazine group, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, and a substituted or unsubstituted $C_5$-$C_{60}$ arylthio group. In some embodiments, $R_{51}$ to $R_{58}$, $R_{61}$ to $R_{69}$, $R_{71}$, and $R_{72}$ may be each independently one of a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group.

In Formula 300, $R_{59}$ may be one of a phenyl group, a naphthyl group, an anthryl group, a biphenyl group, a pyridyl group; and a phenyl group, a naphthyl group, an anthryl group, a biphenyl group, and a pyridyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

In an embodiment of the invention, a compound of Formula 300 may be a compound represented by Formula 300A below:

<Formula 300A>

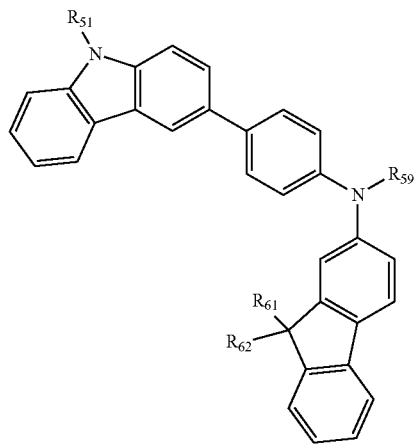

In Formula 300A, $R_{51}$, $R_{62}$, $R_{61}$, and $R_{59}$ may be as defined above.

In some non-limiting embodiments of the invention, at least one of the HIL, HTL, and H-functional layer may include at least one of compounds represented by Formulae 301 to 320 below:

301

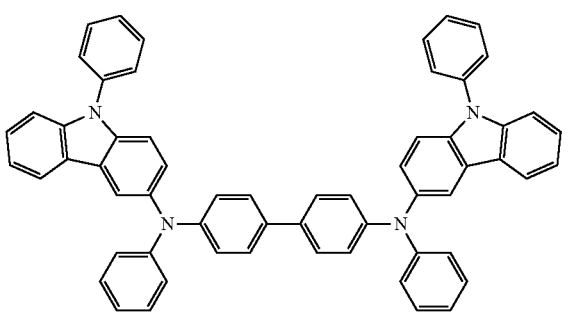

302

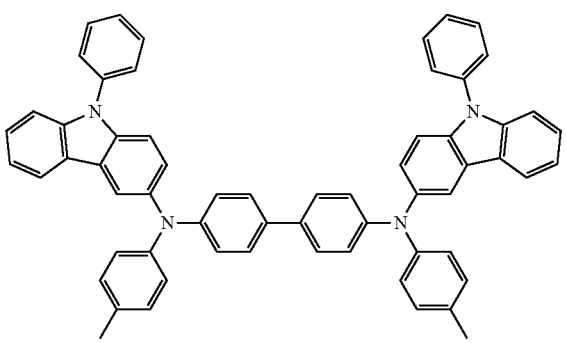

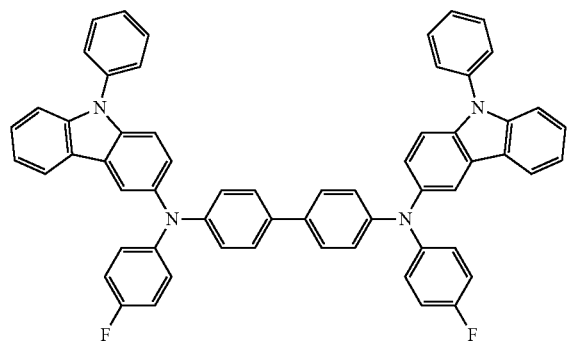
303
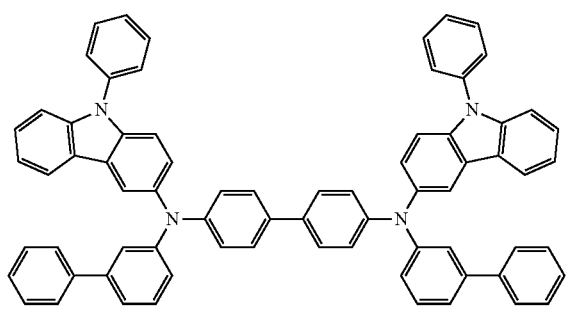
307
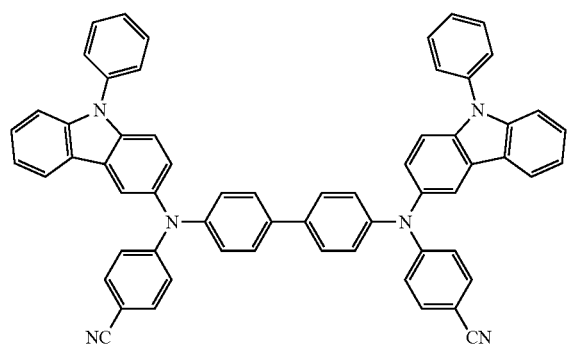
304
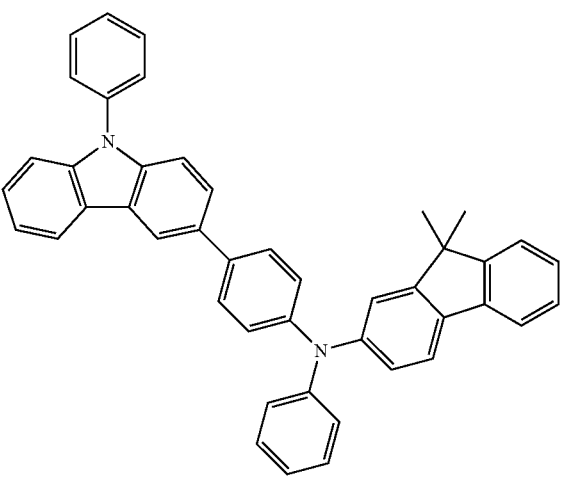
308
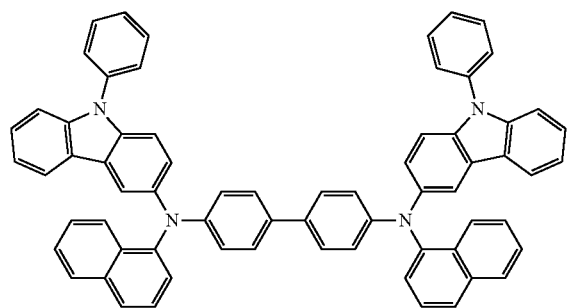
305
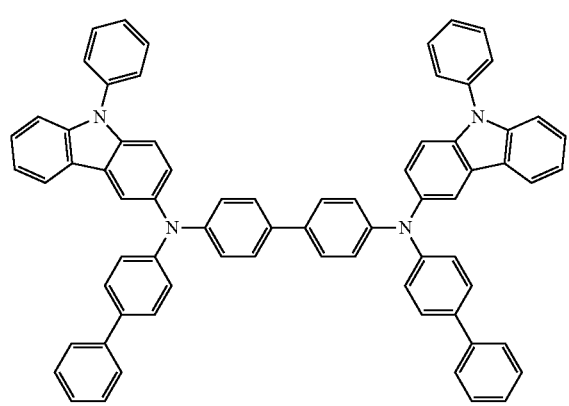
306
309

310
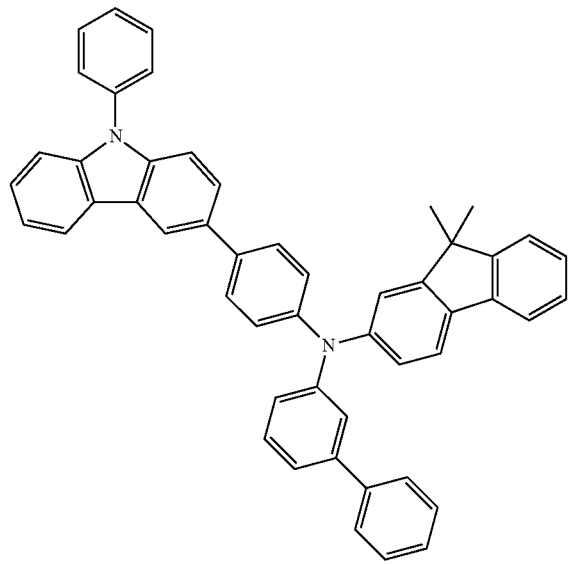
311
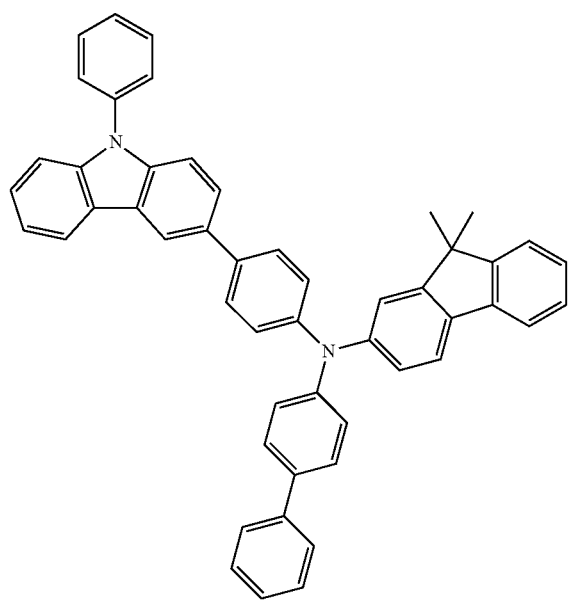
312
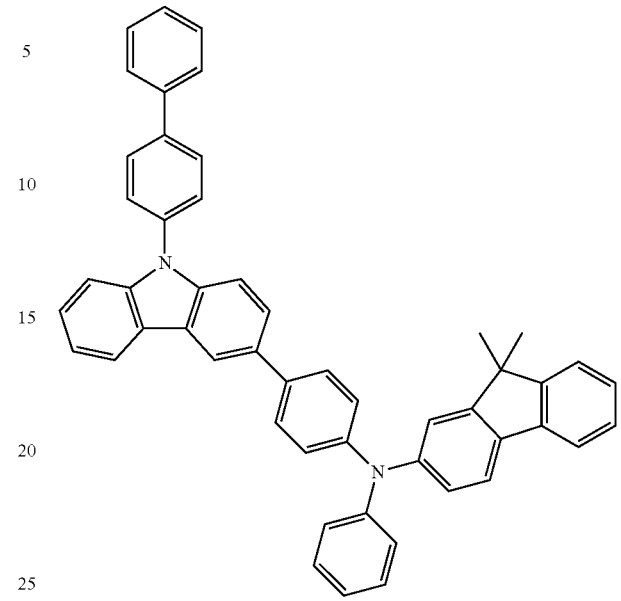
313
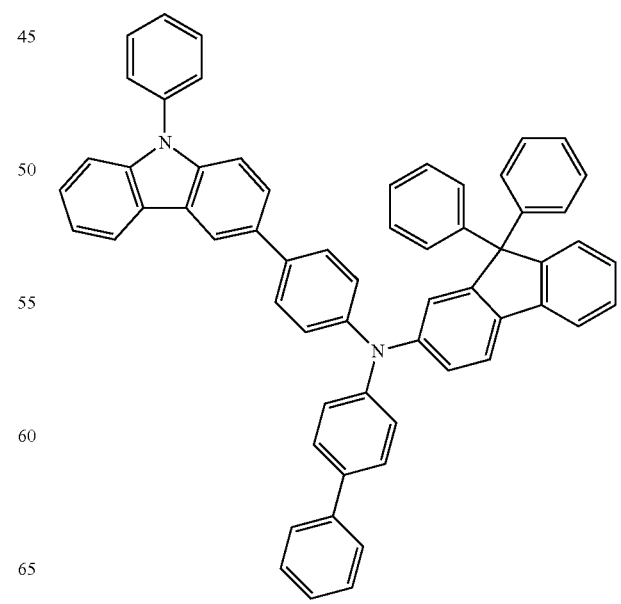

314
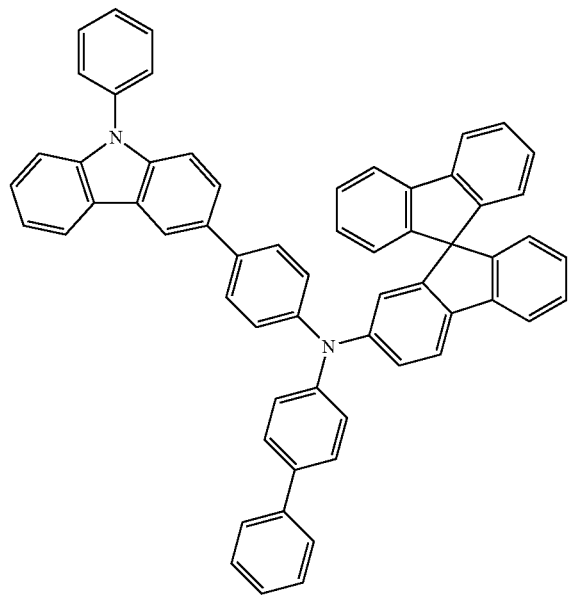
315
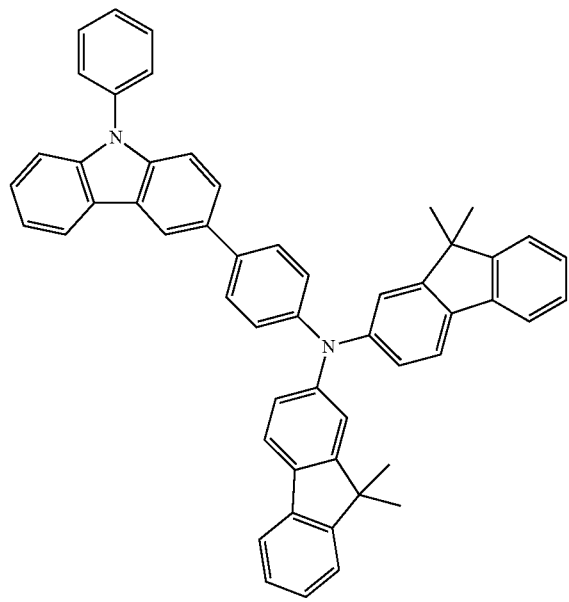
316
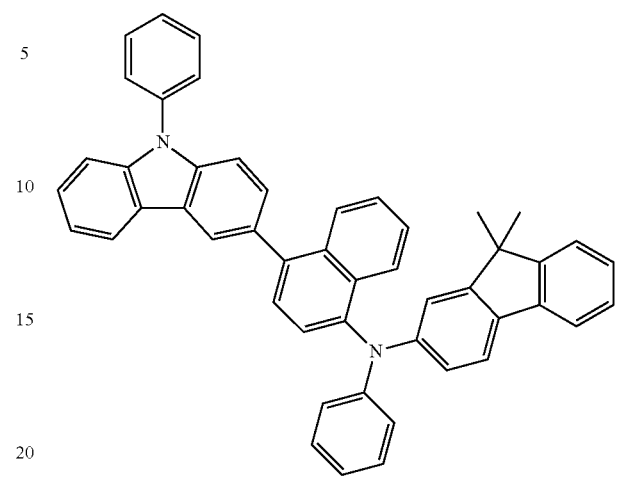
317
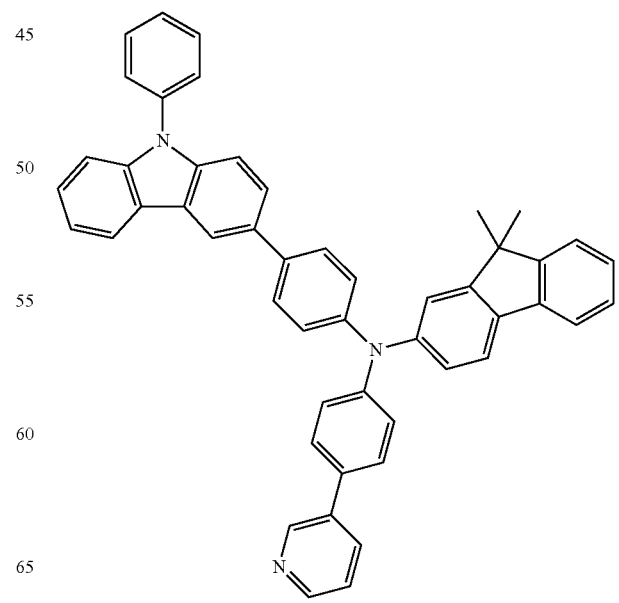
318

319

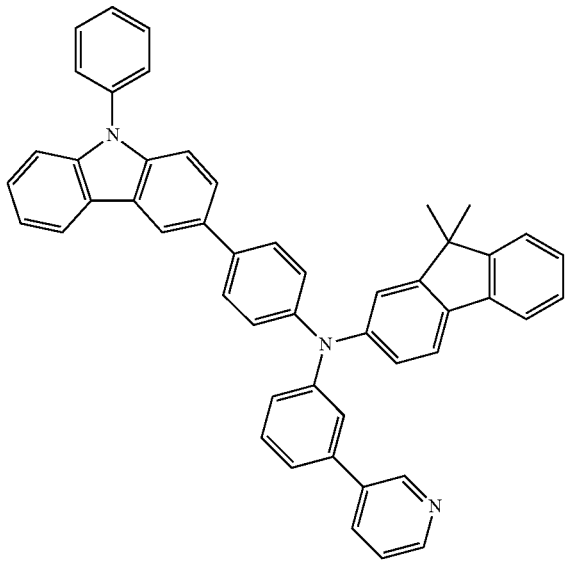

320

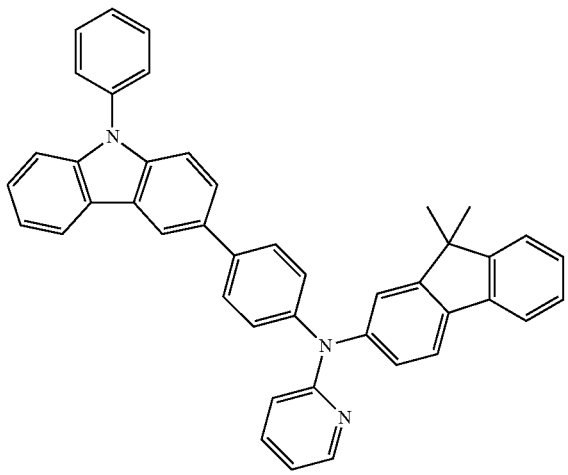

At least one of the HIL, HTL, and H-functional layer may further include a charge-generating material for improved layer conductivity, in addition to a known hole injecting material, hole transport material, and/or material having both hole injection and hole transport capabilities as described above.

The charge-generating material may be, for example, a p-dopant. The p-dopant may be selected from quinine derivatives, metal oxides, and compounds with a cyano group, but are not limited thereto. Non-limiting examples of the p-dopant are quinone derivatives such as tetracyanoquinodimethane (TCNQ), 2,3,5,6-tetrafluoro-7,7,8,8-tetracyanoquinodimethane (F4-TCNQ), and the like; metal oxides such as tungsten oxide, molybdenum oxide, and the like; and cyano-containing compounds such as Compound 200 below:

<Compound 200>

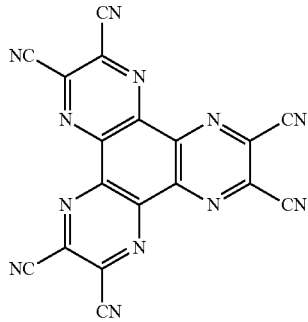

<F4-TCNQ>

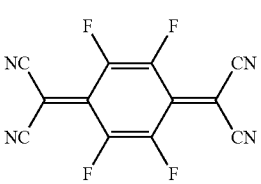

When the hole injection layer, hole transport layer, or H-functional layer further includes a charge-generating material, the charge-generating material may be homogeneously dispersed or inhomogeneously distributed in the layer.

A buffer layer may be disposed between the EML and at least one of the HIL, HTL, and H-functional layer. The thickness of the buffer layer may correspond to an optical resonance distance of light, which depends upon the wavelength of the light emitted from the EML, and the buffer layer may increase efficiency thereby. The buffer layer may include at least one of a hole injecting material and a hole transporting material. In some other embodiments of the invention, the buffer layer may include the same material as one of the materials included in the HIL, HTL, and H-functional layer that underly the buffer layer.

Then, an EML may be formed on one of the HTL, H-functional layer, and buffer layer by any of vacuum deposition, spin coating, casting, LB deposition, and the like. When the EML is formed using vacuum deposition or spin coating, the deposition and coating conditions may be similar to those for the formation of the HIL, though the conditions for deposition and coating may vary according to the material that is used to form the EML.

The EML may be formed using any of a variety of light-emitting materials. In some embodiments, the EML may be formed using a host and a dopant. Dopants that may be used to form the EML may include either a fluorescent dopant or a phosphorescent dopant. Suitable hosts and dopants are widely known in the art.

Non-limiting examples of the host are tris(8-hydroxyquinolinato)aluminum (Alq3), 4,4'-bis(N-carbazolyl)1,1'-biphenyl (CBP), poly(n-vinylcarbazole) (PVK), 9,10-di(naphthalene-2-yl)anthracene (ADN), tris(4-carbazolyl-9-ylphenyl)amine (TCTA), 1,3,5-tris(N-phenylbenzimidazole-2-yl)benzene (TPBI), 3-tert-butyl-9,10-di-2-naphthylanthracene (TBADN), 2,7-bis(9,9-diethylfluoren-2-yl)-9,9-diethylfluorene (E3), a distyrylarylene (DSA), 4,4'-bis(carbazol-9-yl)-2,2'-dimethylbiphenyl (dmCBP) (see formula below), and Compounds 501 to 509 below:

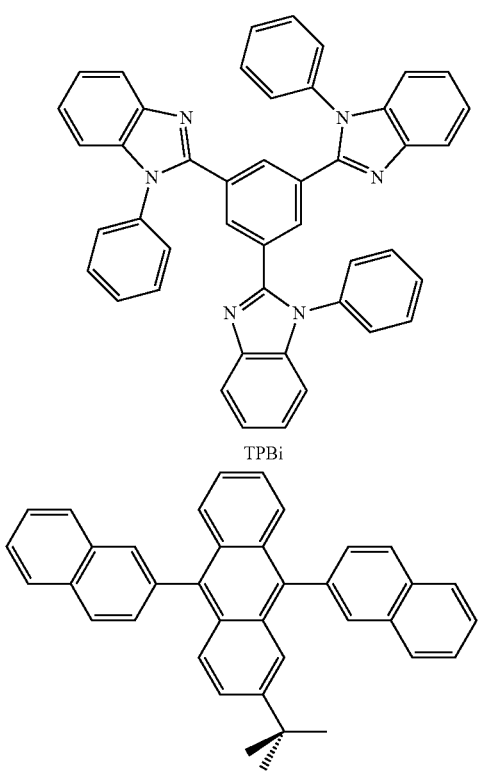
TPBi
TBADN
E3
PVK
ADN
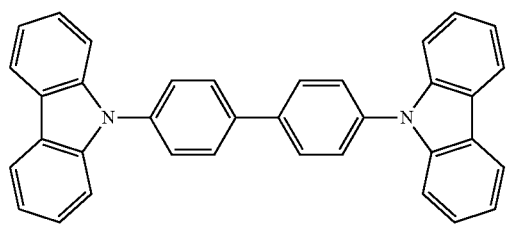
CBP
-continued
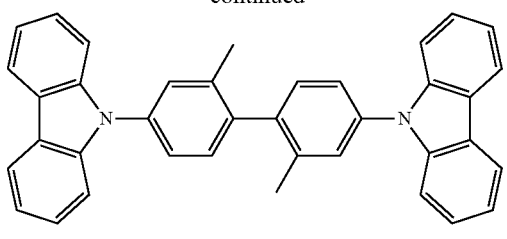
dmCBP
507
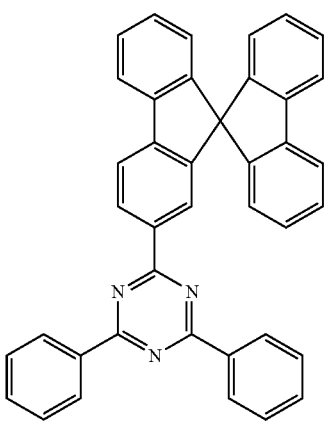
508
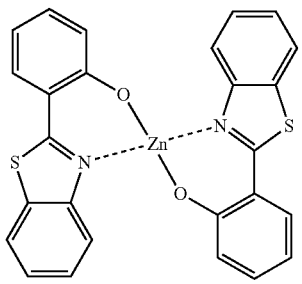
509
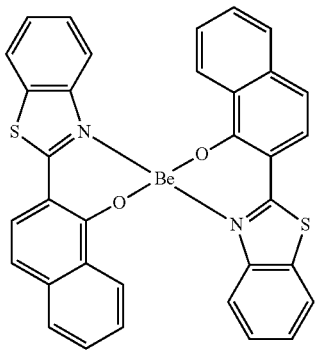
501
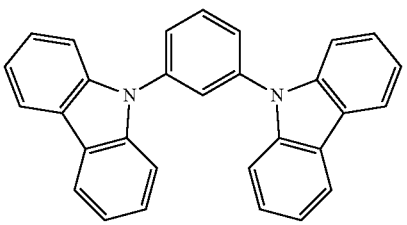

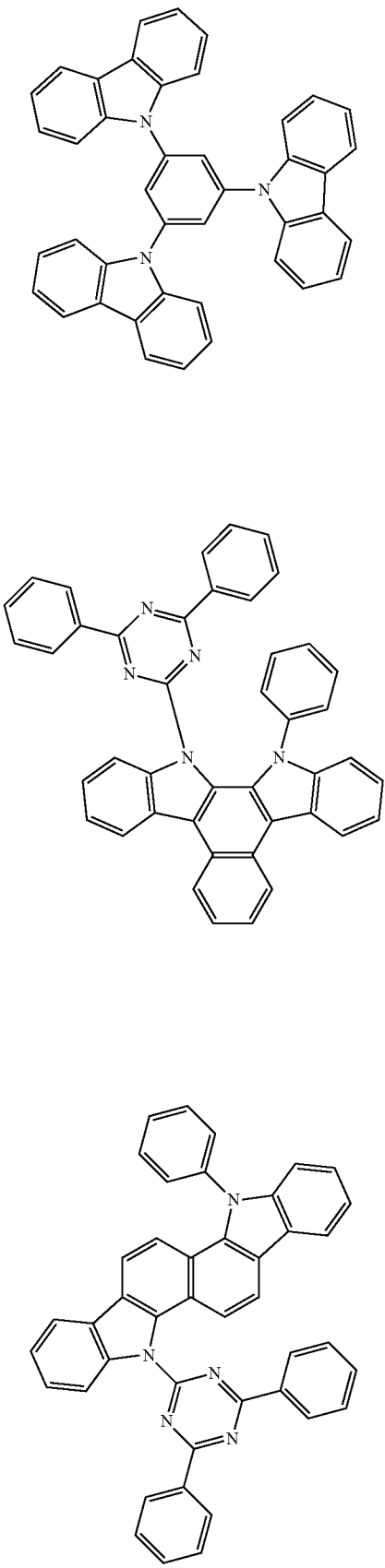

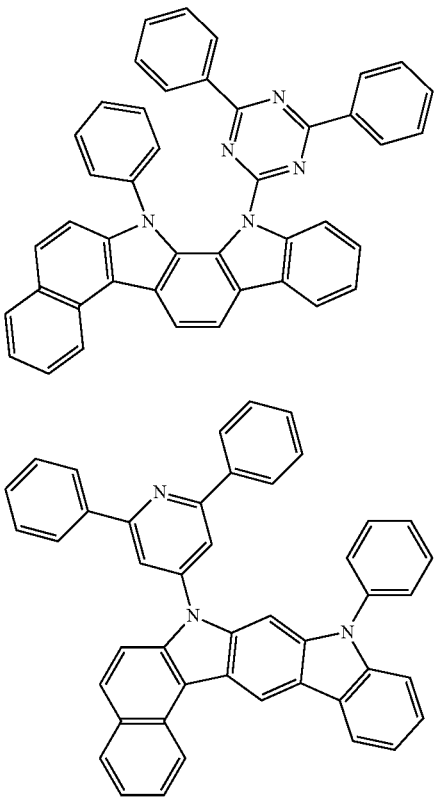

In some embodiments, an anthracene-based compound represented by Formula 400 below may be used as the host.

<Formula 400>

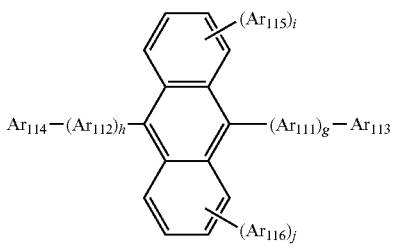

In Formula 400, $Ar_{111}$ and $Ar_{112}$ may be each independently a substituted or unsubstituted $C_5$-$C_{60}$ arylene group; $Ar_{113}$ to $Ar_{116}$ may be each independently one of a substituted or unsubstituted $C_1$-$C_{10}$ alkyl group and a substituted or unsubstituted $C_5$-$C_{60}$ aryl group; and g, h, i, and j may be each independently an integer from 0 to 4.

In some non-limiting embodiments, $Ar_{111}$ and $Ar_{112}$ in Formula 400 may be each independently a phenylene group, a naphthylene group, a phenanthrenylene group, or a pyrenylene group; or a phenylene group, a naphthylene group, a phenanthrenylene group, a fluorenyl group, or a pyrenylene group that are substituted with at least one of a phenyl group, a naphthyl group, and an anthryl group.

In Formula 400 above, g, h, I, and j may be each independently 0, 1, or 2.

In Formula 400, $Ar_{113}$ to $Ar_{116}$ may be each independently one of a $C_1$-$C_{10}$ alkyl group that is substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group; and

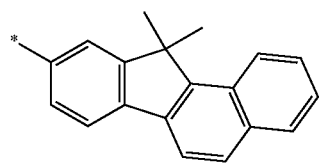
, but are not limited thereto.

For example, the anthracene-based compound of Formula 400 above may be one of the compounds represented by the following formulae, but is not limited thereto:

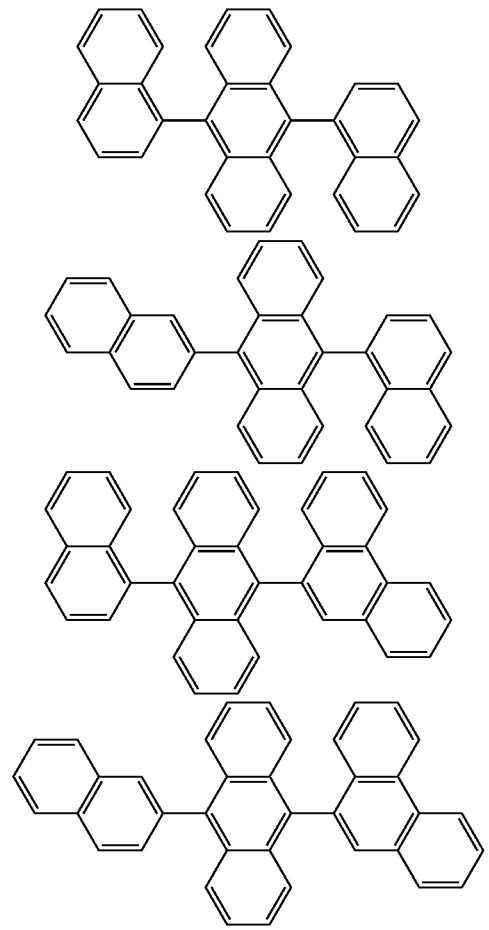

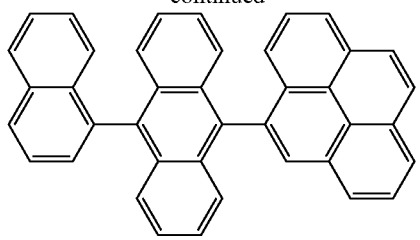

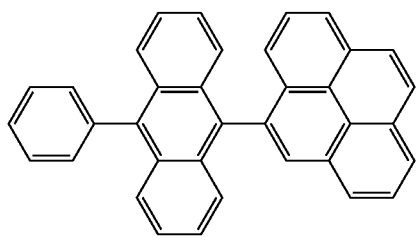

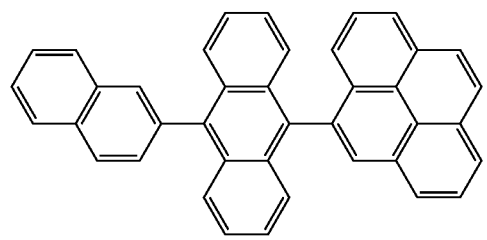

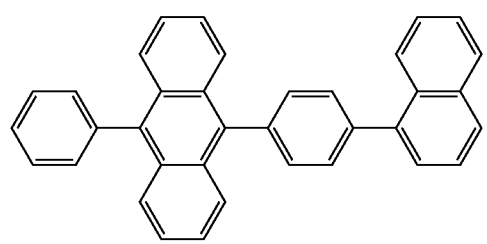

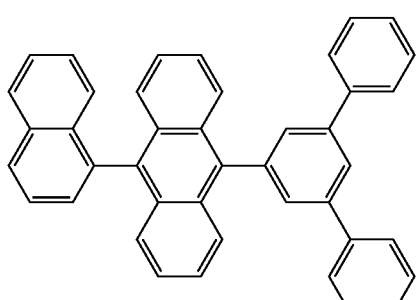

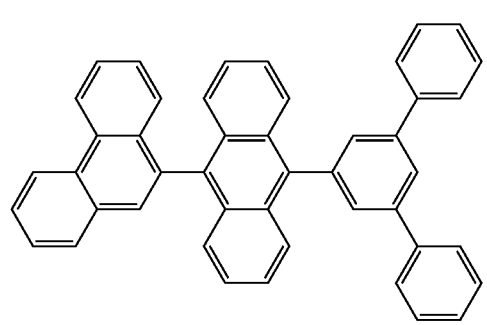

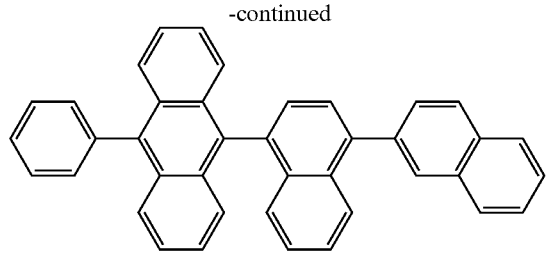

63
-continued
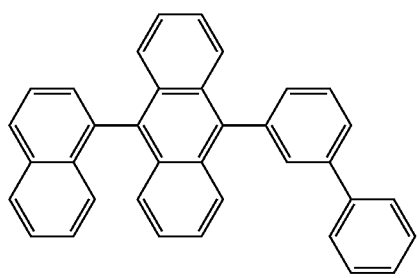
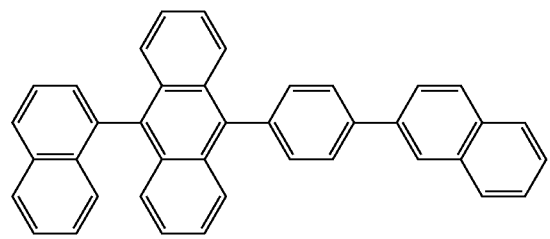
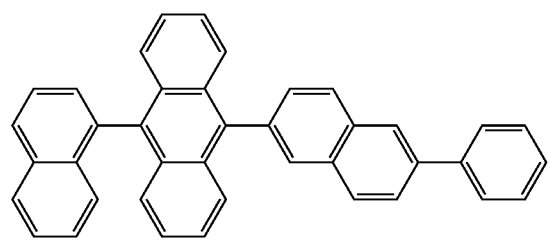
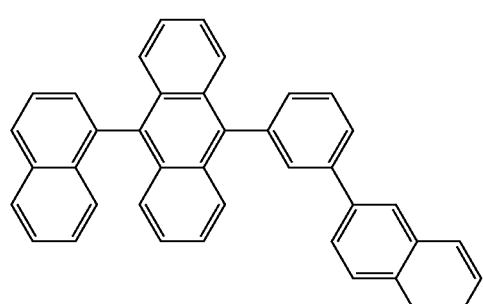
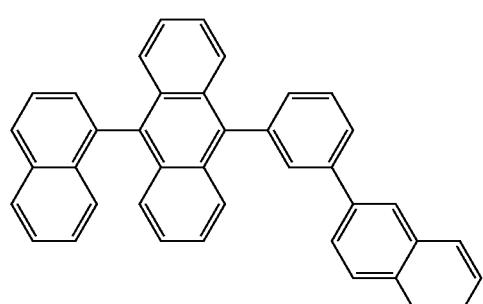
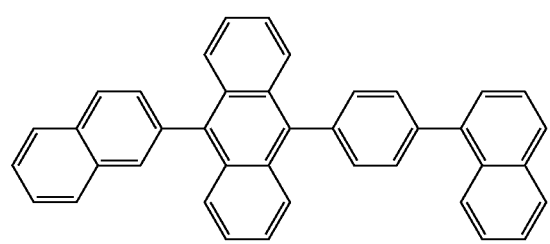
64
-continued
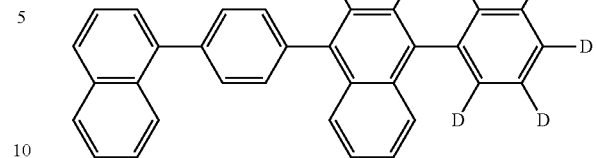
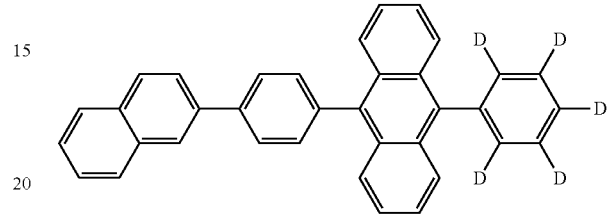
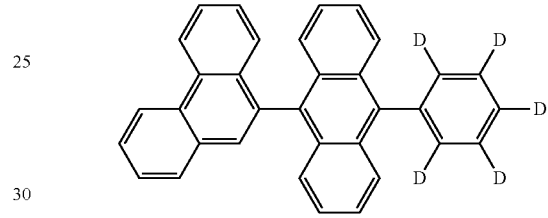
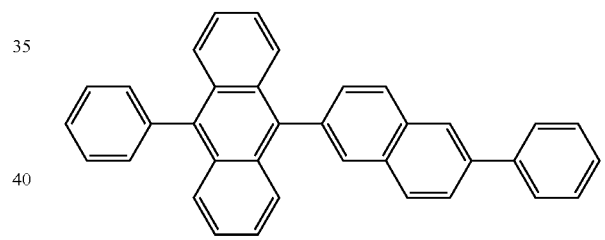
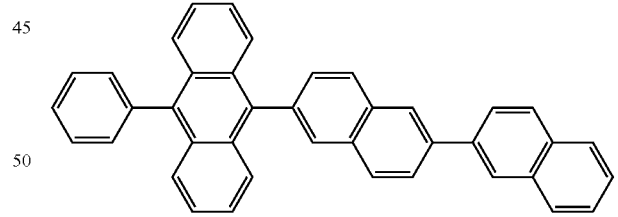
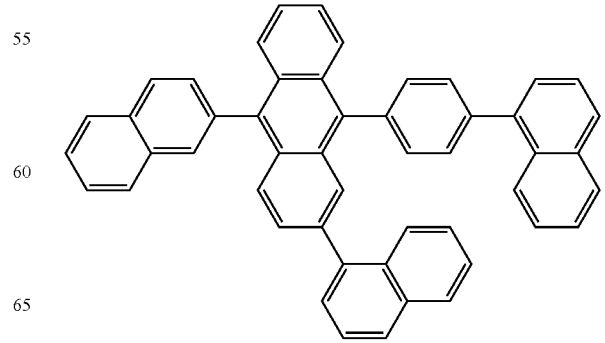

-continued

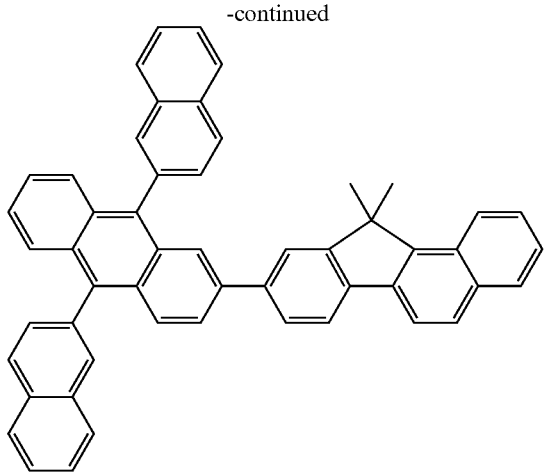

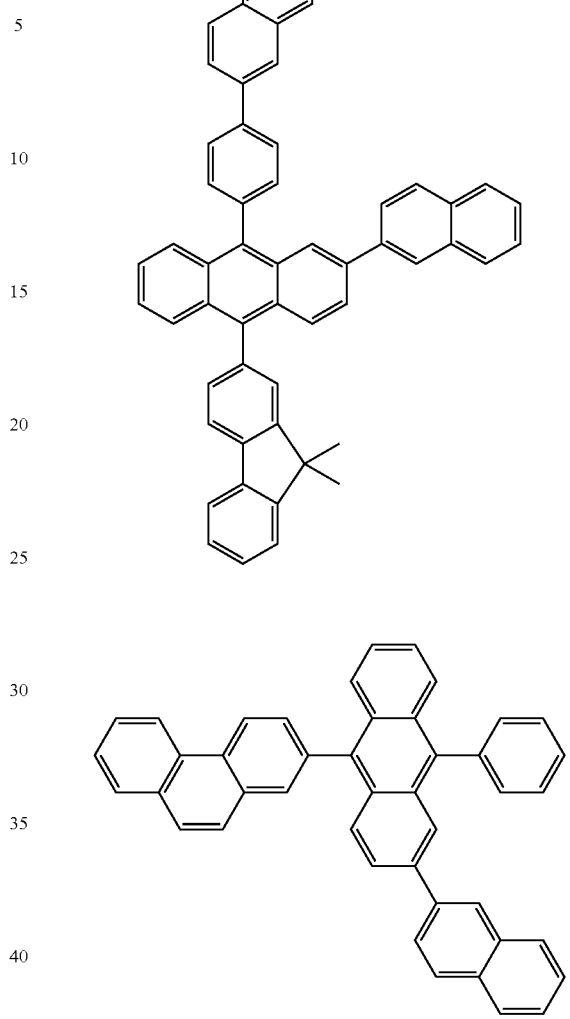

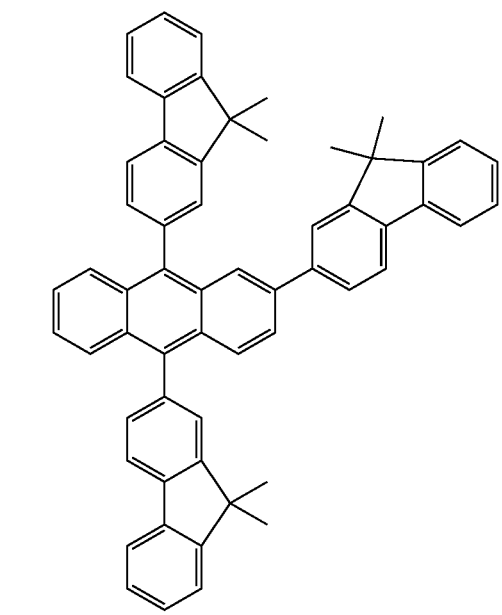

In some embodiments, an anthracene-based compound represented by Formula 401 below may be used as the host:

<Formula 401>

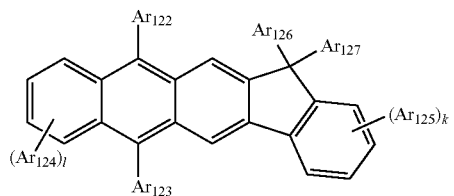

Ar$_{122}$ to Ar$_{125}$ in Formula 401 above may be defined as described above in conjunction with Ar$_{113}$ of Formula 400, and thus detailed descriptions thereof will not be provided here.

Ar$_{126}$ and Ar$_{127}$ in Formula 401 above may be each independently a C$_1$-C$_{10}$ alkyl group, for example, a methyl group, an ethyl group, or a propyl group.

In Formula 401, k and l may be each independently an integer from 0 to 4, for example, 0, 1, or 2.

For example, the anthracene-based compound of Formula 401 above may be one of the compounds represented by the following formulae, but is not limited thereto:

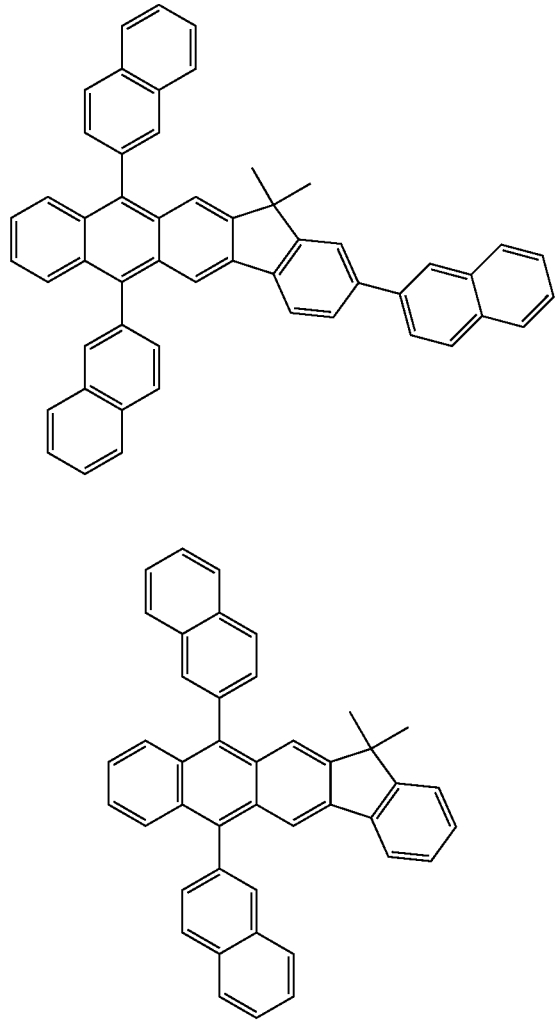

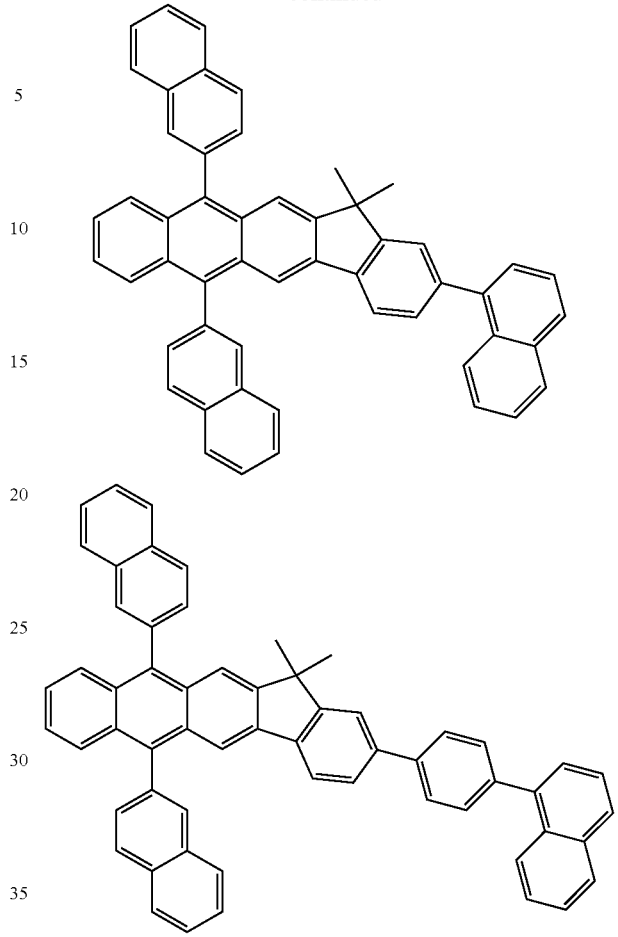

When the organic light-emitting device is a full color organic light-emitting device, the emission layer may be patterned into a red emission layer, a green emission layer, and a blue emission layer.

At least one of the red EML, the green EML, and the blue EML may include a dopant such as one of those shown below (ppy=phenylpyridine).

Non-limiting examples of the blue dopant are compounds represented by the following formulae.

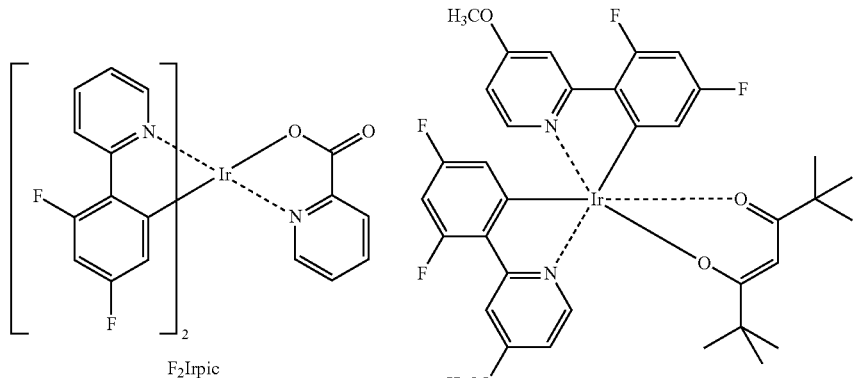

F$_2$Irpic (F2ppy)2Ir(tmd)

-continued
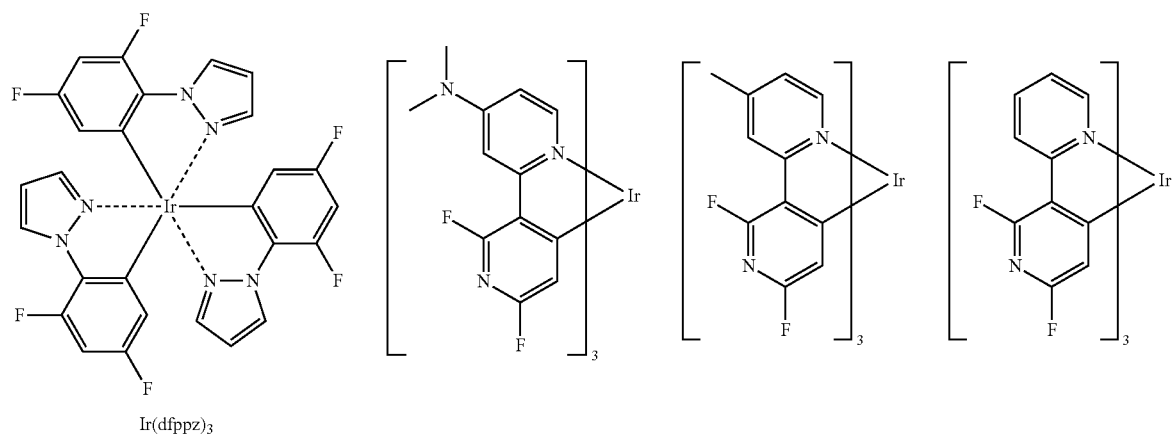
Ir(dfppz)₃
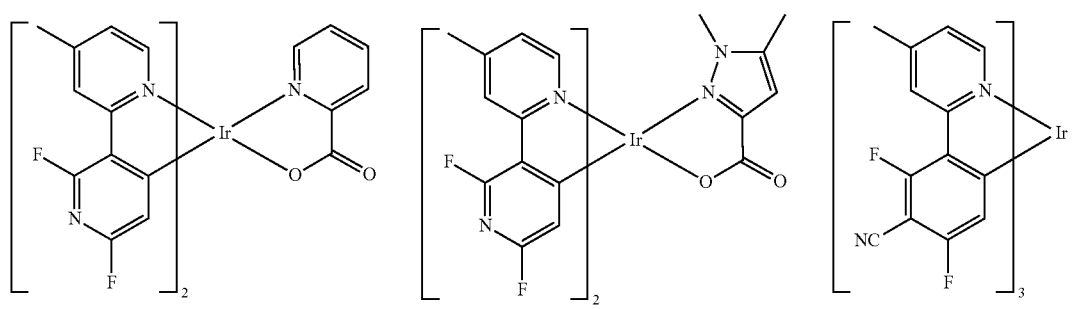
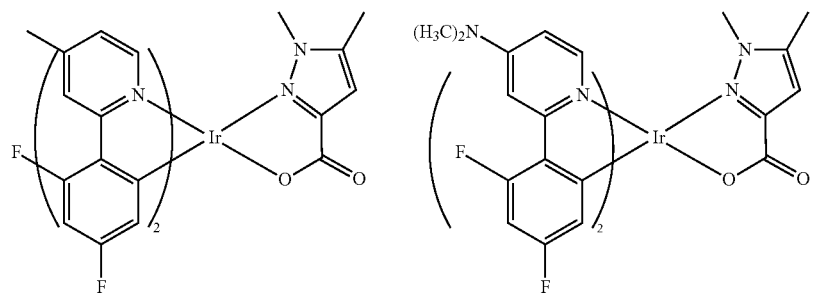
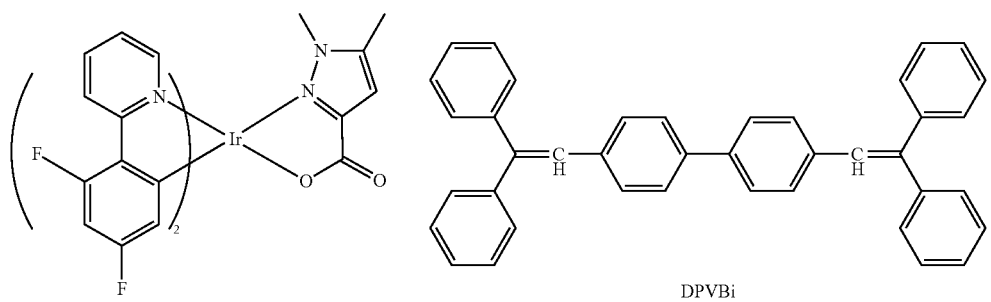
DPVBi
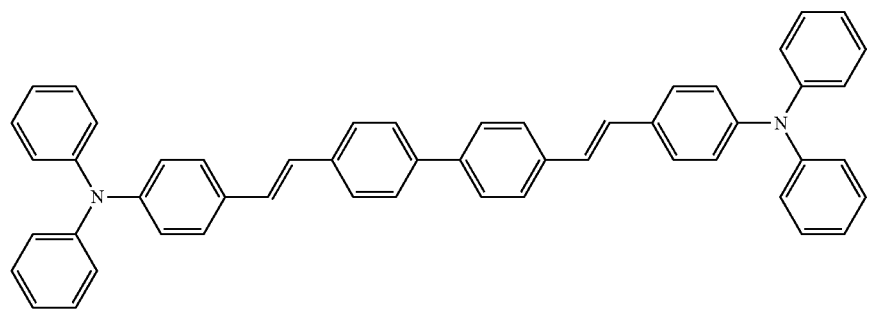
DPAVBi

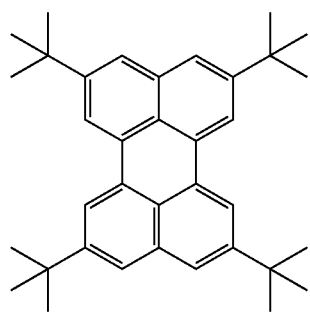
TBPe
Non-limiting examples of the red dopant are compounds represented by the following formulae.
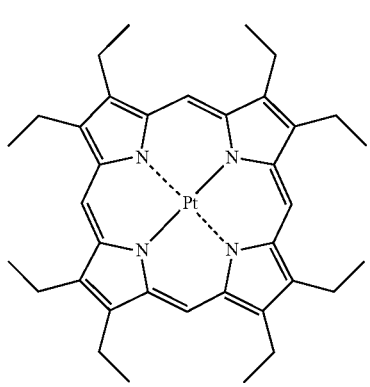
PtOEP
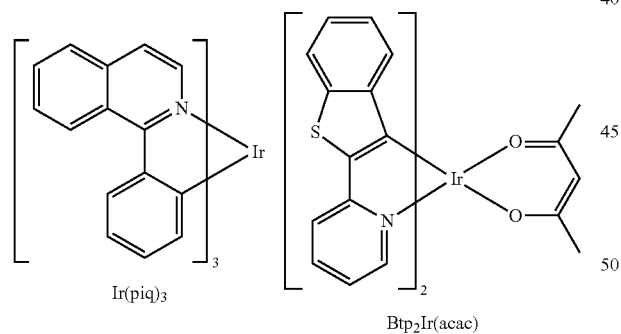
Ir(piq)₃             Btp₂Ir(acac)
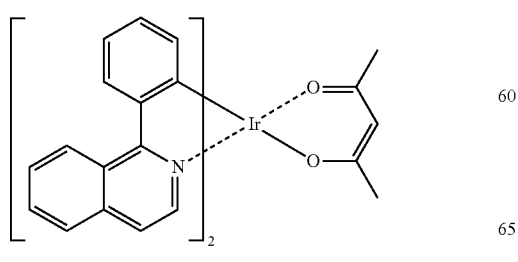
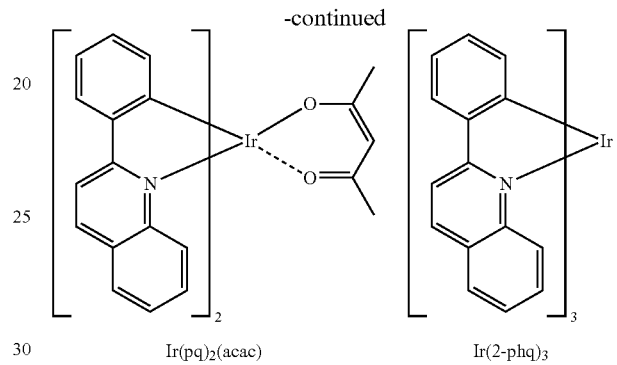
Ir(pq)₂(acac)        Ir(2-phq)₃
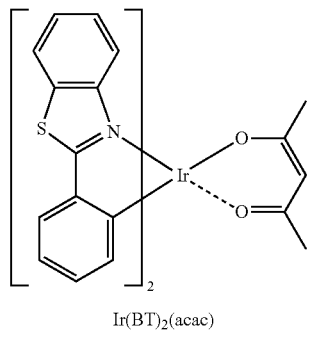
Ir(BT)₂(acac)
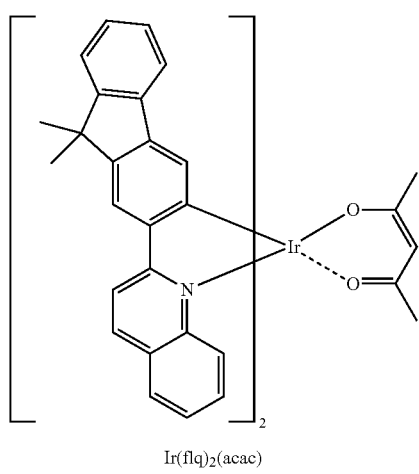
Ir(flq)₂(acac)

-continued
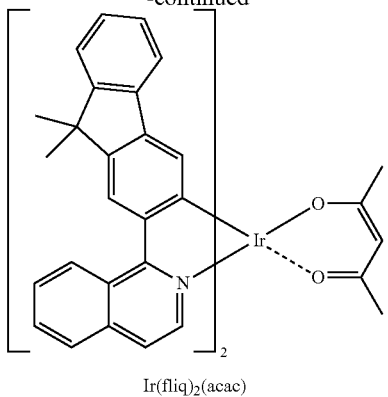
Ir(fliq)₂(acac)
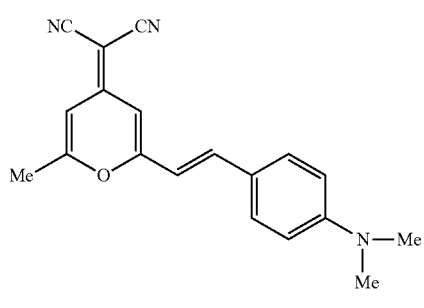
DCM
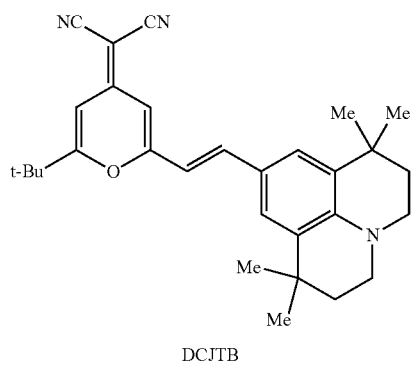 [SMILES: CC(C)(C)C1=CC(=C(C#N)C#N)C=C(/C=C/c2cc3c4c(c2)C(C)(C)CCN4CCC3(C)C)O1]
DCJTB
Non-limiting examples of the green dopant are compounds represented by the following formulae.
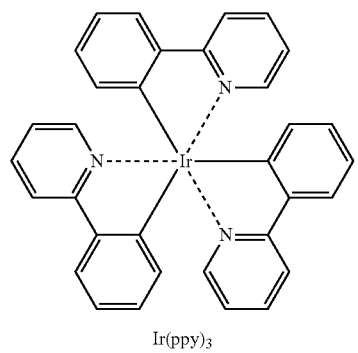
Ir(ppy)₃
-continued
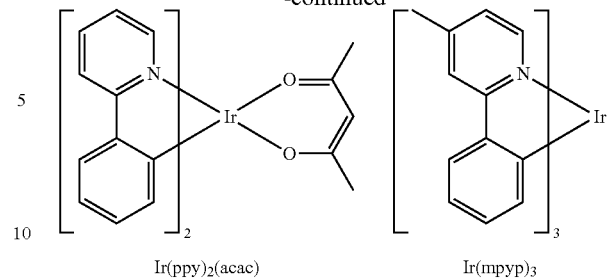
Ir(ppy)₂(acac)   Ir(mpyp)₃
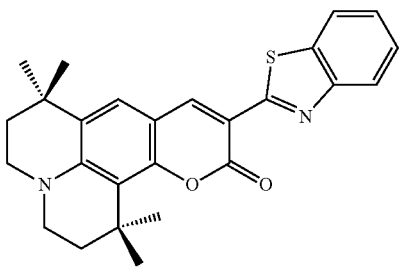
C545T
Non-limiting examples of the dopant that may be used in the EML are Pt complexes represented by the following formulae:
D1
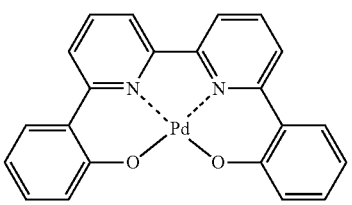
D2
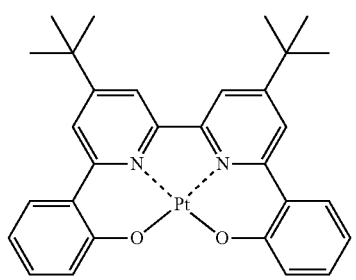
D3
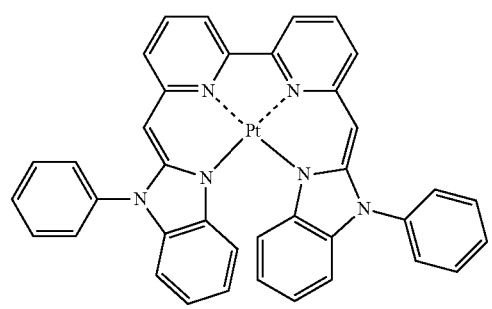

D4
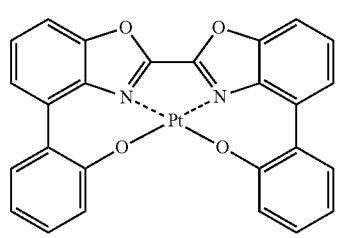
D5
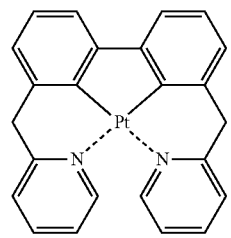
D6
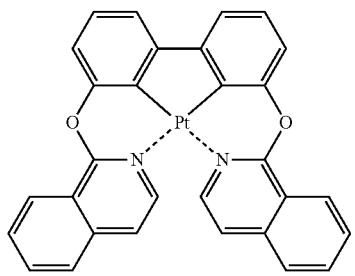
D7
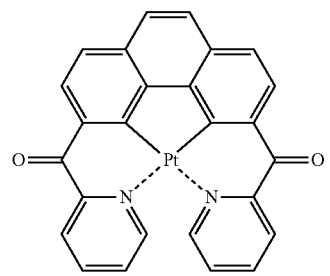
D8
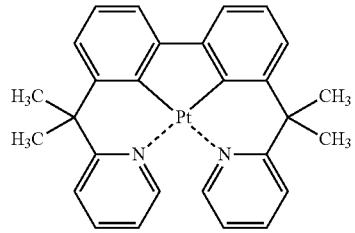
D9
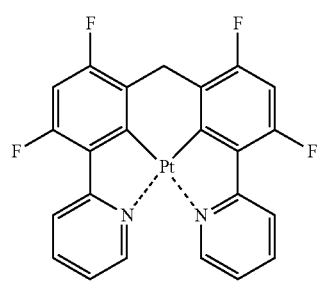
D10
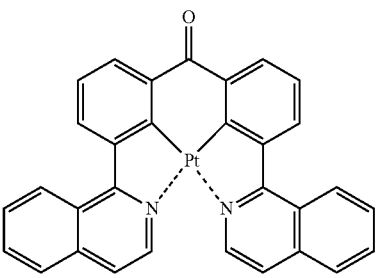
D11
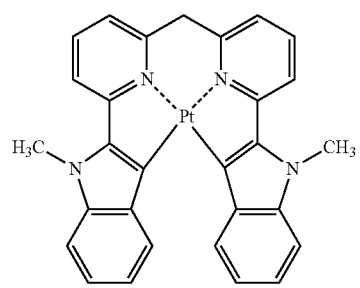
D12
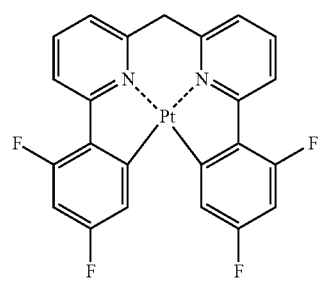
D13
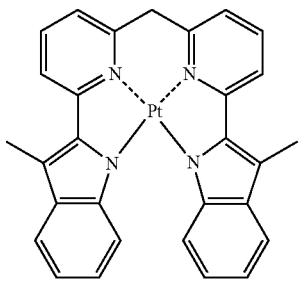
D14
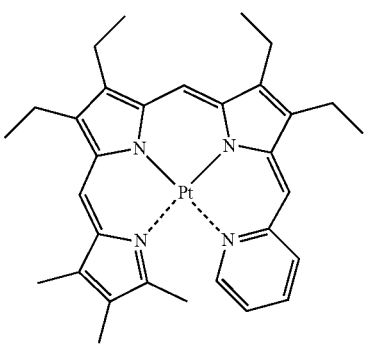

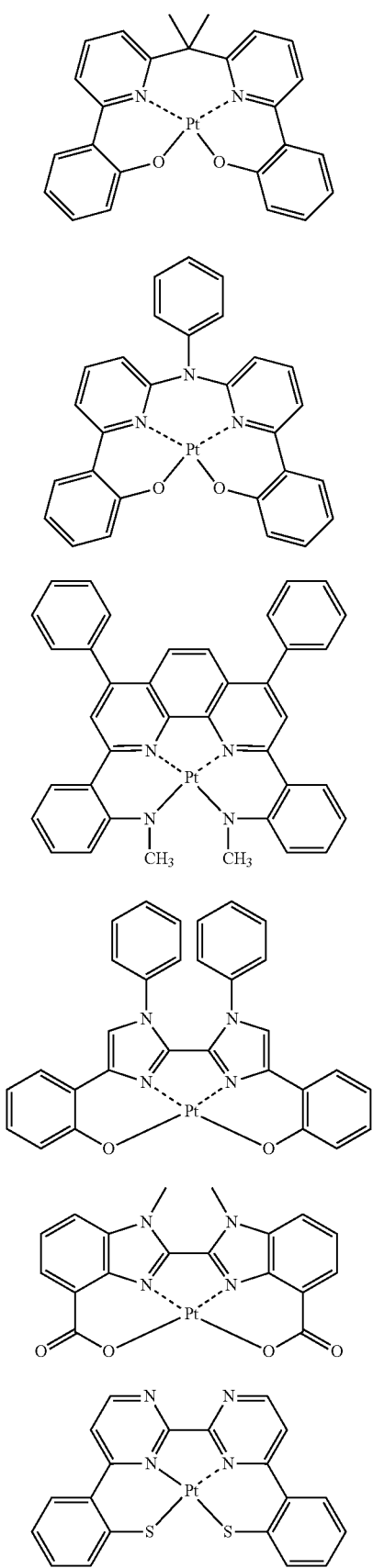
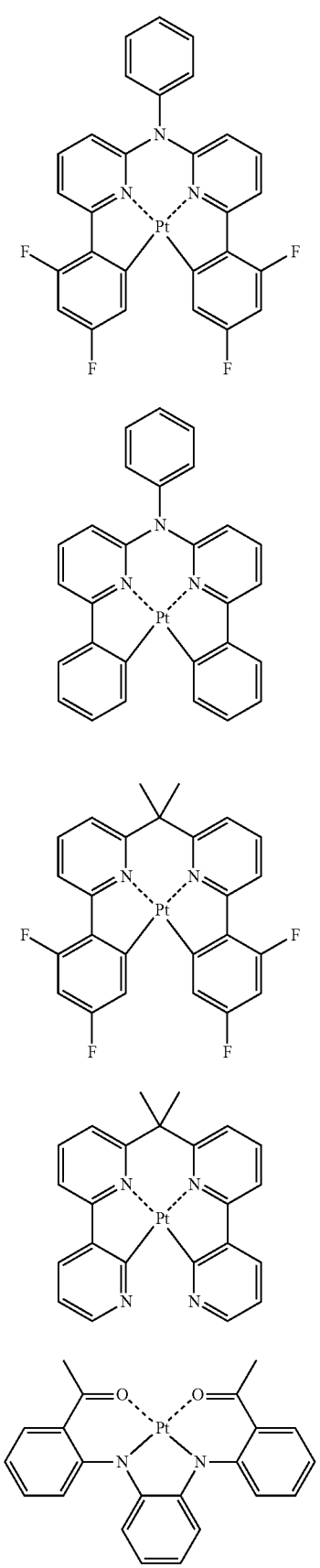

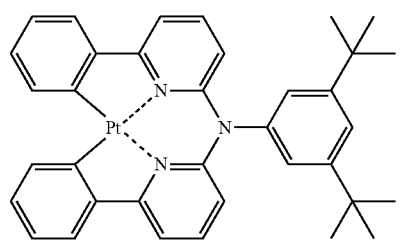 D26
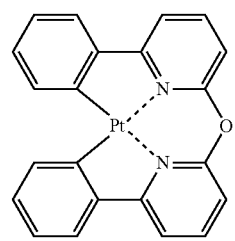 D27
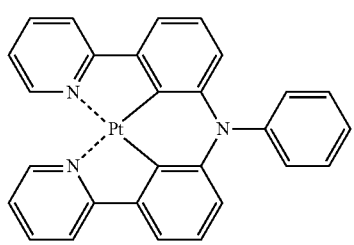 D28
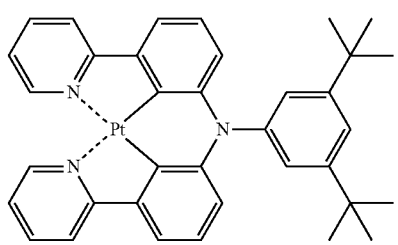 D29
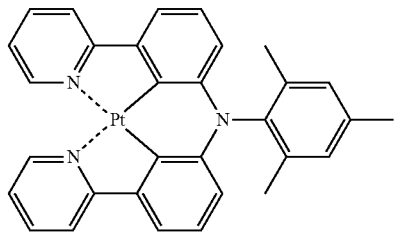 D30
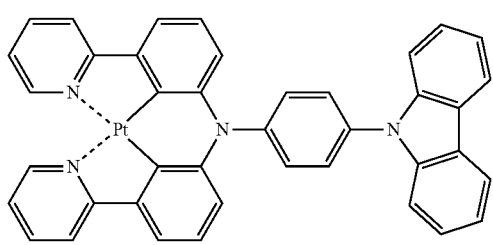 D31
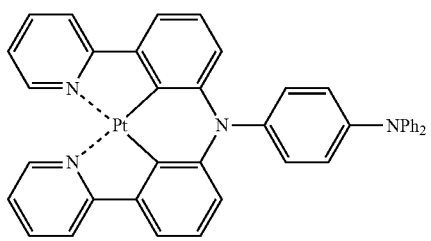 D32
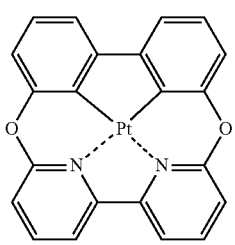 D33
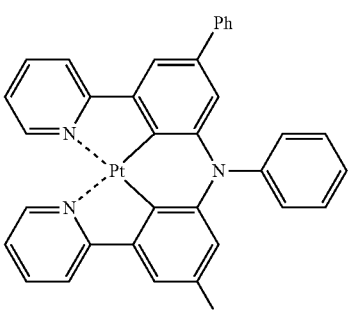 D34
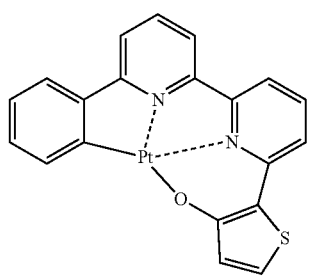 D35
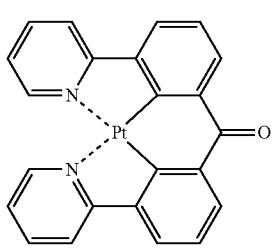 D36

-continued
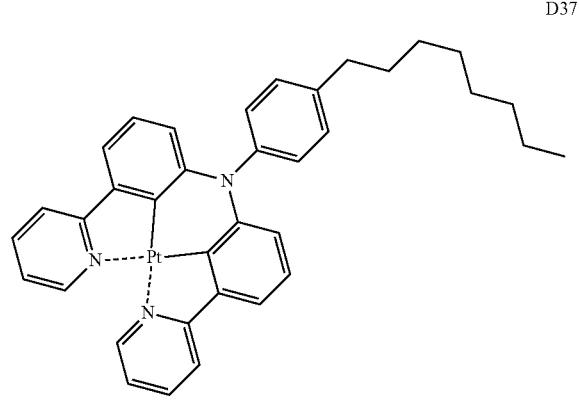
D37
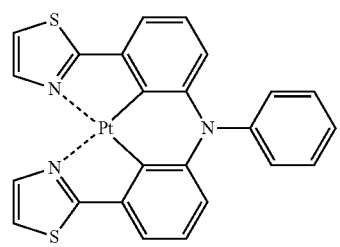
D38
D39
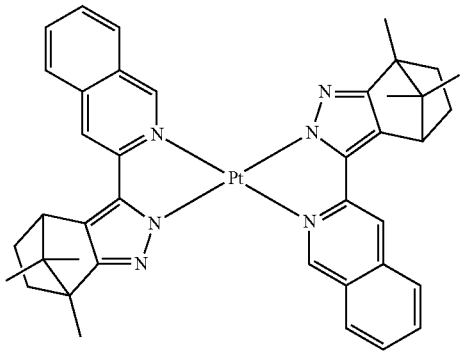
D40
D41
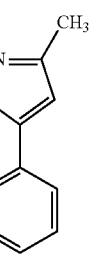
D42
D43
D44
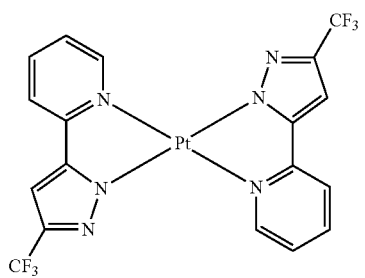
D45
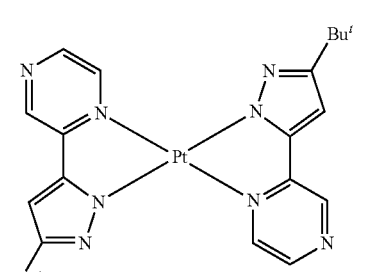
D46
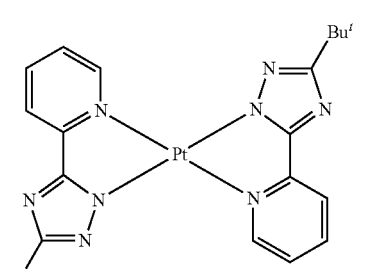

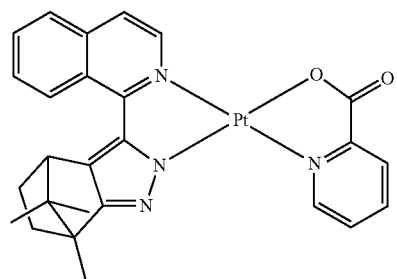

D47

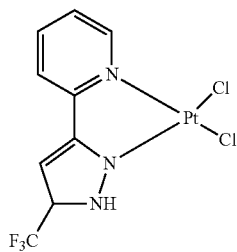

D48

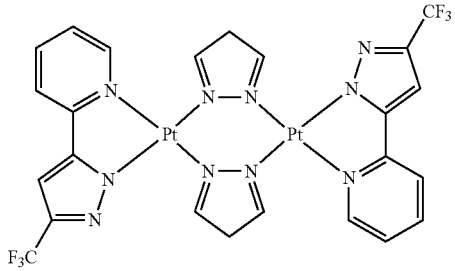

D49

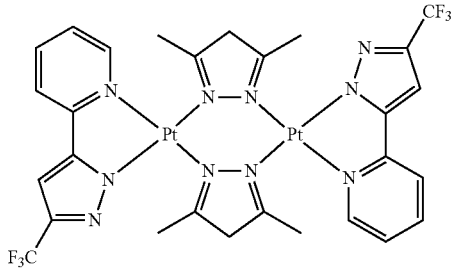

D50

Non-limiting examples of the dopant that may be used in the EML are Os complexes represented by the following formulae:

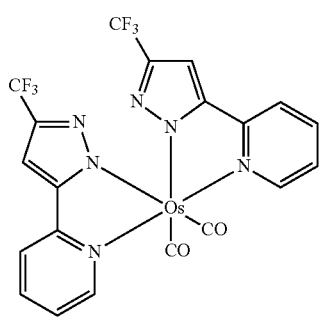

Os(fppz)₂(CO)₂

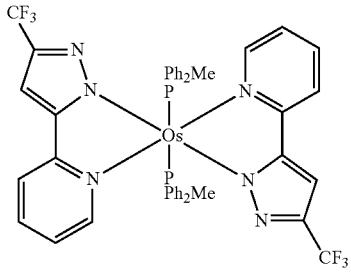

Os(fppz)₂(PPh₂Me)₂

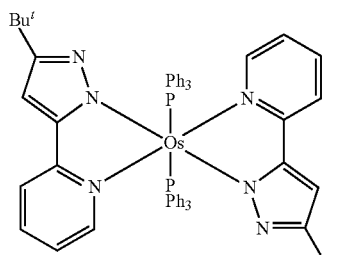

Os(bppz)₂(PPh₃)₂

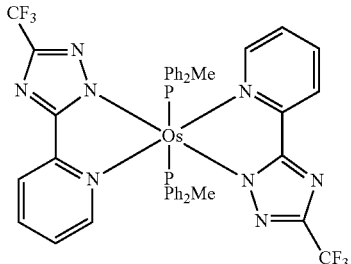

Os(fptz)₂(PPh₂Me)₂

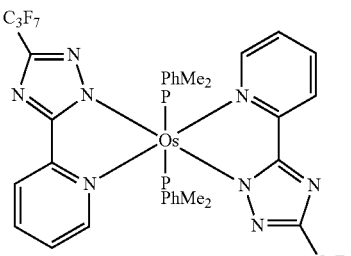

Os(bptz)₂(PPhMe₂)₂

When the EML includes both a host and a dopant, the amount of the dopant may be from about 0.01 to about 15 parts by weight based on 100 parts by weight of the host. However, the amount of the dopant is not limited to this range.

The thickness of the EML may be from about 100 Å to about 1000 Å, and in some embodiments, from about 200 Å to about 600 Å. When the thickness of the EML is within these ranges, the EML may have good light emitting ability without a substantial increase in driving voltage.

Then, an ETL may be formed on the EML by one of vacuum deposition, spin coating, casting, and the like. When the ETL is formed using one of vacuum deposition and spin coating, the deposition and coating conditions may be similar to those used for the formation of the HIL, though the deposition and coating conditions may vary according to the compound that is used to form the ETL. A material for forming the ETL may be the compound of Formula 1 above or any material that can stably transport electrons injected from an electron injecting electrode (cathode). Non-limiting examples of materials for forming the ETL are a quinoline derivative, such as tris(8-hydroxyquinolinato)aluminum (Alq3), 3-(biphen-4-yl)-4-phenyl-5-(4-tert-butylphenyl)-1,2,4-triazole (TAZ), bis (2-methyl-8-quinolinato)-4-phenylphenolate aluminum (BAlq), beryllium bis(benzoquinolin-10-olate (Bebq$_2$), 9,10-di(naphthalene-2-yl)anthracene (ADN), Compound 201, and Compound 202, but are not limited thereto.

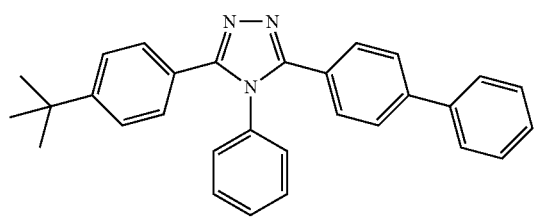

TAZ

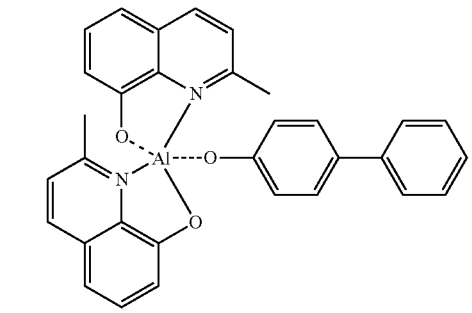

BAlq

<Compound 201>

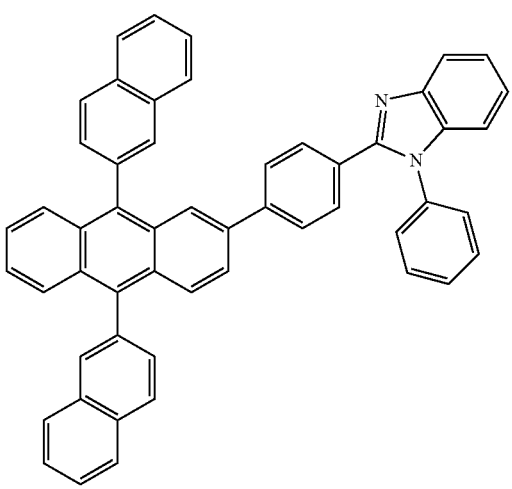

<Compound 202>

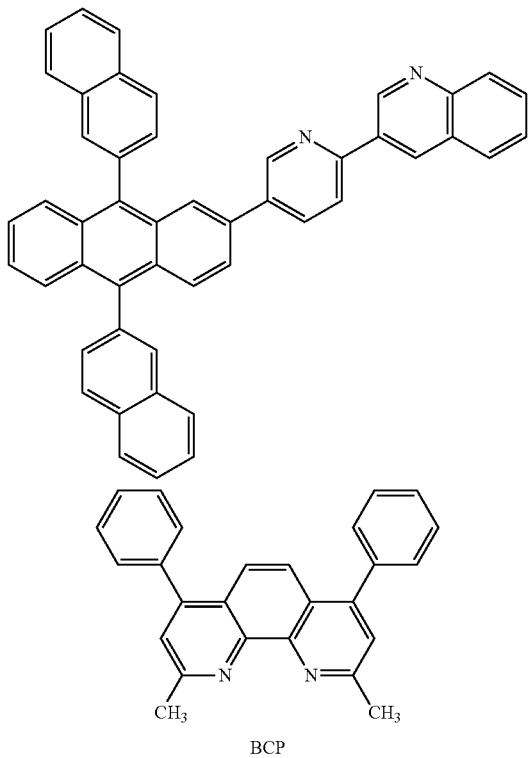

BCP

The thickness of the HTL may be from about 100 Å to about 1000 Å, and in some embodiments, from about 150 Å to about 500 Å. When the thickness of the ETL is within these ranges, the ETL may have satisfactory electron transporting ability without imparting a substantial increase in driving voltage to the OLED.

In some embodiments of the invention, the ETL may further include a metal-containing material, in addition to an electron-transporting organic compound.

The metal-containing material may include a lithium (Li) complex. Non-limiting examples of the Li complex are lithium quinolate (LiQ) and Compound 203 below:

<Compound 203>

Then, an EIL, which facilitates injection of electrons from the cathode, may be formed on the ETL. Any suitable electron-injecting material may be used to form the EIL.

Non-limiting examples of materials for forming the EIL are LiF, NaCl, CsF, Li$_2$O, and BaO, which are known in the art. The deposition and coating conditions for forming the EIL may be similar to those for the formation of the HIL, though the deposition and coating conditions may vary according to the material that is used to form the EIL.

The thickness of the EIL may be from about 1 Å to about 100 Å, and, in some embodiments, from about 3 Å to about 90 Å. When the thickness of the EIL is within these ranges, the EIL may have satisfactory electron injection ability without imparting a substantial increase in driving voltage to the OLED.

Finally, the second electrode is disposed on the organic layer. The second electrode may be a cathode that is an electron injection electrode. A suitable material for forming the second electrode may be one of a metal, an alloy, an electro-conductive compound that has a low work function, and a mixture thereof. In this regard, the second electrode may be formed of one of lithium (Li), magnesium (Mg), aluminum (Al), aluminum (Al)-lithium (Li), calcium (Ca), magnesium (Mg)-indium (In), magnesium (Mg)-silver (Ag), and the like, and may be formed as a thin film type transmission electrode. In some embodiments of the invention, to manufacture a top-emission light-emitting device, the transmission electrode may be formed of indium tin oxide (ITO) or indium zinc oxide (IZO).

Although the organic light-emitting device of FIG. 1 is described above, the present invention is not limited thereto.

When a phosphorescent dopant is used in the EML, a HBL may be formed between the HTL and the EML or between the H-functional layer and the EML by using one of vacuum deposition, spin coating, casting, Langmuir-Blodgett (LB) deposition, and the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. Any suitable hole-blocking material may be used. Non-limiting examples of hole-blocking materials are oxadiazole derivatives, triazole derivatives, and phenanthroline derivatives. For example, bathocuproine (BCP), which is represented by the following formula, may be used as a material for forming the HBL.

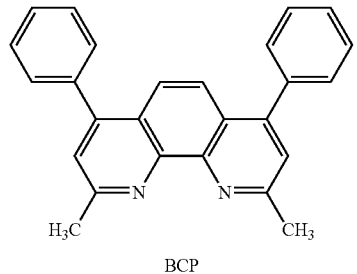 [SMILES: Cc1cc(-c2ccccc2)c2ccc3c(-c4ccccc4)cc(C)nc3c2n1 ; "BCP"]

BCP

The thickness of the HBL may be from about 20 Å to about 1000 Å, and in some embodiments, from about 30 Å to about 300 Å. When the thickness of the HBL is within these ranges, the HBL may have improved hole blocking ability without imparting a substantial increase in driving voltage to the OLED.

According to embodiments of the present invention, the organic light-emitting device may be included in various types of flat panel display devices, such as in one of a passive matrix organic light-emitting display device and an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

In some embodiments of the invention, the organic layer of the organic light-emitting device may be formed of the compound of Formula 1 by using a deposition method or may be formed using a wet method of coating a solution of the compound of Formula 1.

Hereinafter, the present invention will be described in detail with reference to the following synthesis examples and other examples. However, these examples are for illustrative purposes only and are not intended to limit the scope of the present invention.

EXAMPLES

Synthesis Example 1

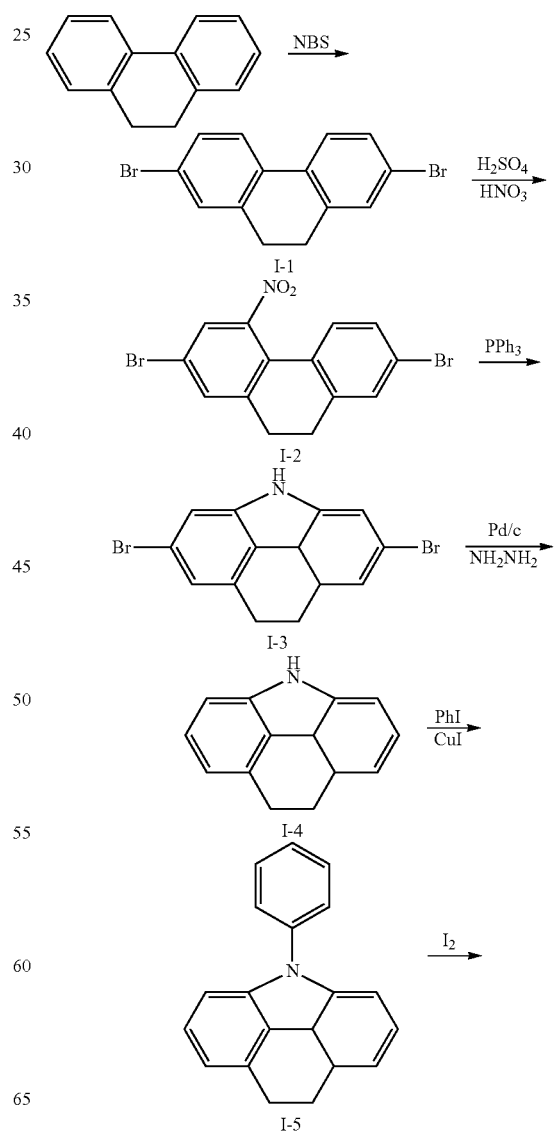

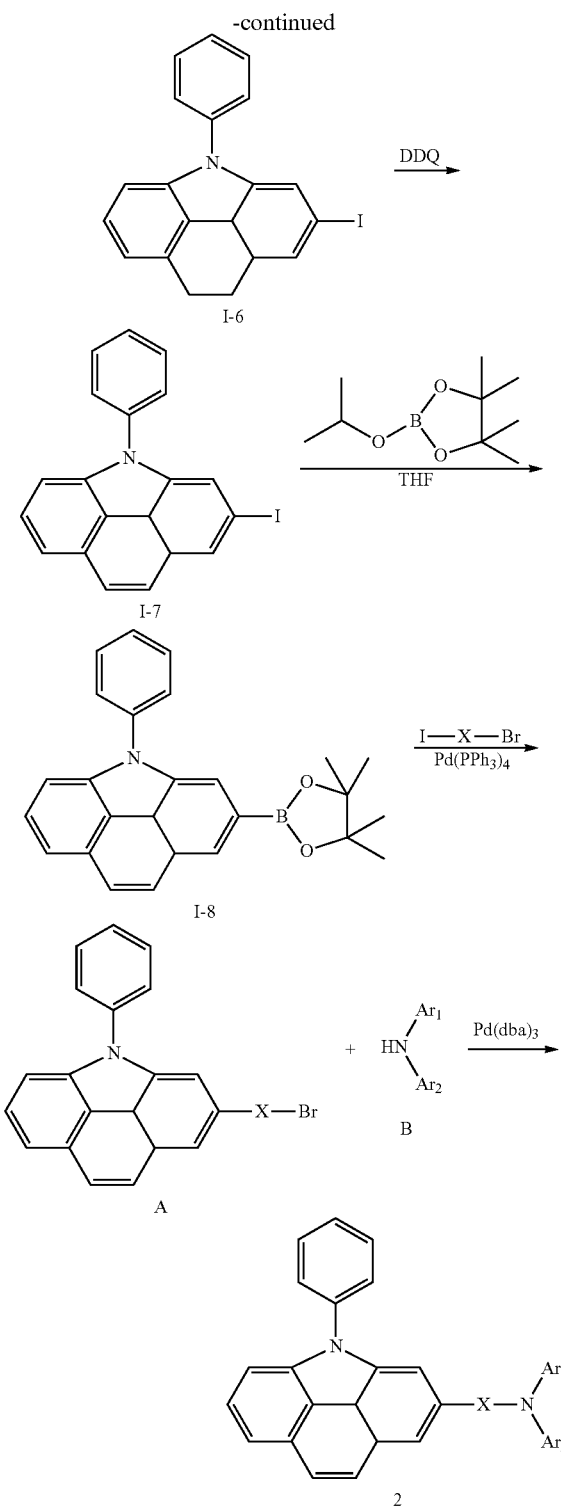

Synthesis of Intermediate I-1

Quantities of 10.0 g (55.4 mmol) of 9,10-dihydrophenanthrene, 21.8 g (121.0 mmol) of N-bromosuccinimide, and 0.5 g (2.7 mmol) of p-toluenesulfonic acid (p-TsOH), respectively, were dissolved in 30 mL of acetonitrile, then stirred at about 50° C. for about 12 hours. The reaction solution was cooled to room temperature, then stirred for about 30 minutes to precipitate crystals. The crystals were collected using a filter under reduced pressure, then washed with methanol to yield 8.4 g of Intermediate I-1 as gray crystals (yield: 45%). This compound was identified using LC-MS. $C_{14}H_{10}Br_2$ $M^+335.9$

Synthesis of Intermediate I-2

A quantity of 5.0 g (15.0 mmol) of Intermediate I-1 was completely dissolved in 50 mL of dichloromethane, followed by an addition of 1.7 g (30.0 mmol) of nitric acid at room temperature to obtain a mixture. 1.5 g (15.0 mmol) of sulfuric acid was slowly dropwise added to the mixture and then stirred at about 30° C. for about 6 hours. After completion of the reaction, the reaction solution was cooled to room temperature. Then, 50 mL of methanol was added thereto and stirred for about 2 hours to precipitate crystals. The crystals were collected using a filter under reduced pressure, then washed with methanol to obtain 5.2 g of Intermediate I-2 as yellow crystals (yield: 90%). This compound was identified using LC-MS. $C_{14}H_9Br_2NO_2$ $M^+380.9$

Synthesis of Intermediate I-3

A quantity of 4.6 g (12.0 mmol) of Intermediate I-2 was dissolved in 30 mL of o-dichlorobenzene, then heated until it was completely dissolved, and this was followed by an addition of 4.7 g (18.0 mmol) of triphenylphosphine and stirring at about 180° C. for about 3 hours. The reaction solution was then cooled room temperature, and the solvent was evaporated from the solution. The residue was separated and purified using silica gel column chromatography, then washed with methanol to obtain 2.9 g of Intermediate I-3 as white crystals (yield: 70%). This compound was identified using LC-MS. $C_{14}H_{11}Br_2N$ $M^+350.9$

Synthesis of Intermediate I-4

A quantity of 10 g (28.5 mmol) of Intermediate I-3 and 0.03 g (0.28 mmol) of Pd/c (10%) were completely dissolved in 100 mL of ethanol at room temperature. Next, the solution was heated to about 50° C., followed by dropwise addition of 5.48 g (171 mmol) of hydrazine, and then the solution was stirred for about 24 hours. After cooling the solution to room temperature, the solution was diluted with acetone, and then 100 ml of ice water was added to obtain 3.63 g of Intermediate I-4 as white crystals (yield: 66%). This compound was identified using LC-MS. $C_{14}H_{13}N$; M+196.1

Synthesis of Intermediate I-5

Quantities of 1.93 g (10.0 mmol) of Intermediate I-4, 2.5 g (12.0 mmol) of iodobenzene, 0.2 g (1.0 mmol) of 1,10-phenanthroline, 0.2 g (2.0 mmol) of CuI, and 4.1 g (30.0 mmol) $K_2CO_3$, respectively, were dissolved in 30 mL of N,N-dimethylformamide (DMF) and stirred at about 80° C. for about 24 hours. The reaction solution was cooled to room temperature and then extracted three times with 30 mL portions of water and 40 mL portions of diethylether. The organic phase was collected and was dried using magnesium sulfate, and the solvent was removed by evaporation. The residue was separated and purified using silica gel column chromatography to obtain 2.39 g of Intermediate I-5 (yield: 89%). This compound was identified using LC-MS. $C_{20}H_{17}N$ $M^+272.1$

Synthesis of Intermediate I-6

A quantity of 10 g (37.1 mmol) of Intermediate I-5 was completely dissolved in 100 mL of dichloromethane, and then 3.58 g (14.1 mmol) of iodine and 2.38 g (11.13 mmol) of KIO$_3$ were divided, each into five equal portions, and ⅕ of each was added at a time to the dichloromethane solution. The resulting reaction solution was stirred for about 6 hours and washed with methanol to obtain 8.06 g of Intermediate I-6 (yield: 55%). This compound was identified using LC-MS. C$_{20}$H$_{16}$IN; M+398.1

Synthesis of Intermediate I-7

A quantity of 10 g (25.3 mmol) of Intermediate I-6 was dissolved in 100 mL of toluene in an oxygen atmosphere, and 1.57 g (7.6 mmol) of 2,3-dichloro-5,6-dicyano-1,4-benzoquinone and 0.52 g (7.6 mmol) of NaNO$_2$ were added. The reaction solution was stirred at about 110° C. for about 6 hours. After completion of the reaction, the reaction solution was cooled to room temperature, and the solvent was removed by evaporation. The residue was separated and purified using silica gel column chromatography to obtain 8.94 g of Intermediate I-7 (yield: 90%). This compound was identified using LC-MS. C$_{20}$H$_{14}$IN; M+396.1

Synthesis of Intermediate I-8

A quantity of 10 g (25.3 mmol) of Intermediate I-7 was dissolved in 30 mL of THF, and 10 mL (25.0 mmol, 2.5 M in Hexane) of n-BuLi was slowly dropwise added at about −78° C. The solution was stirred for about 1 hour at the same temperature, and 9.3 mL (50 mmol) of 2-isoproxy-4,4,5,5,-tetramethyl-1,3,2-dioxaborolane was slowly dropwise added. The reaction solution was then stirred at about −78° C. for about 1 hour, followed by stirring at room temperature for about 24 hours. After completion of the reaction, 50 mL of 10% HCl aqueous solution and 50 mL of H$_2$O were added, and the reaction mixture was then extracted three times with 80 mL portions of diethyl ether. The organic phase was collected and was dried using magnesium sulfate, and the solvent was removed by evaporation. The residue was separated and purified using silica gel column chromatography to obtain 7.49 g of Intermediate I-7 (yield: 75%). This compound was identified using LC-MS. C$_{26}$H$_{23}$BNO$_2$; M+396.2

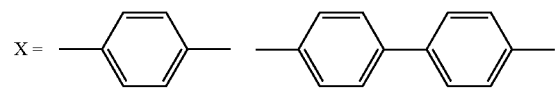

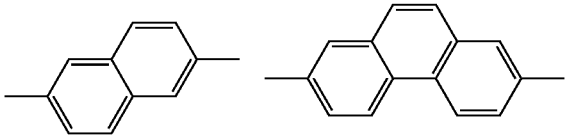

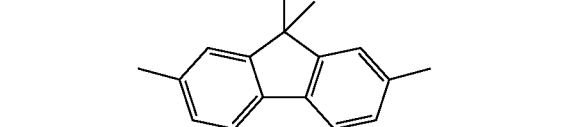

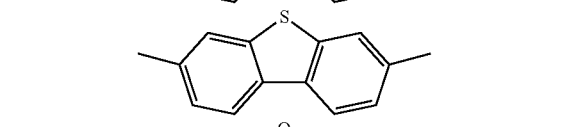

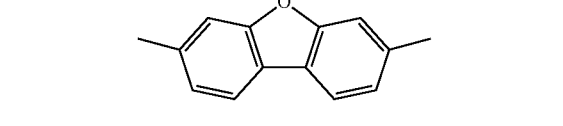

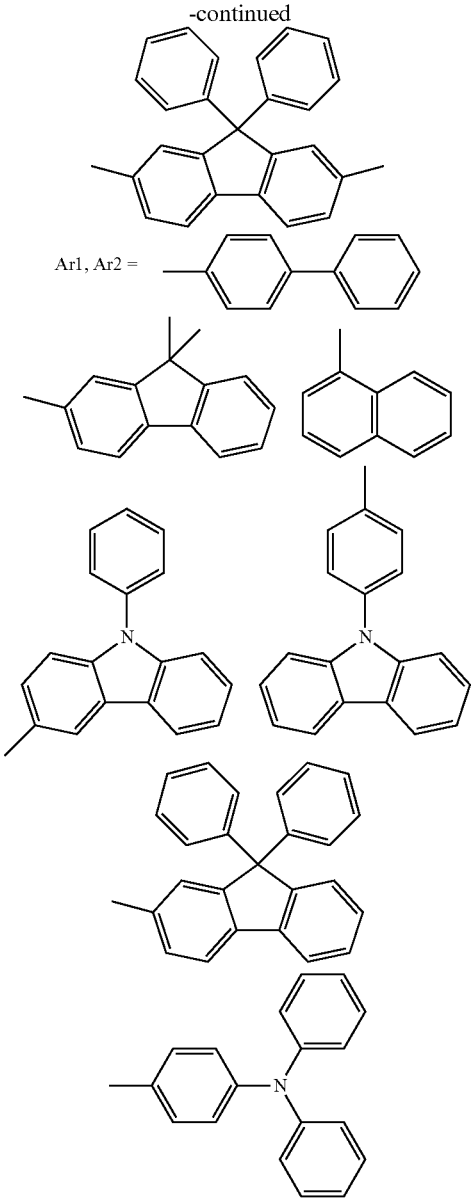

Synthesis of Intermediate A

Quantities of 3.95 g (10 mmol) of Intermediate I-8, 15.0 mmol of I—X—Br, 0.5 mmol of Pd(PPh$_3$)$_4$, and 30.0 mmol of K$_2$CO$_3$, respectively, were dissolved in 30 mL of a mixed solvent of THF/H$_2$O (2:1 by volume), then stirred at about 80° C. for about 5 hours. After the reaction solution was cooled to room temperature, 40 mL of water was added to the reaction solution, which was then extracted three times with 50 mL of diethyl ether. The organic phase was collected and was dried using magnesium sulfate, and the solvent was removed by evaporation. The residue was separated and purified using silica gel column chromatography to obtain Intermediate A. This compound was identified using LC-MS.

Synthesis of Compound 2

Quantities of 1.41 g (5.0 mmol) of Intermediate A (1-bromo-4-iodobenzene), 1.92 g (6.0 mmol) of Intermediate B (bis(biphenyl-4-yl)amine), 0.09 g (0.1 mmol) of Pd$_2$(dba)$_3$, 0.01 g (0.1 mmol) of PtBu$_3$, and 1.0 g (10.0 mmol) of KOtBu, respectively, were dissolved in 20 mL of toluene, then stirred at about 85° C. for about 4 hours. After the reaction solution was cooled to room temperature, then extracted three times with 20 mL portions of water and 20 mL portions of diethylether. The organic phase was collected and was dried using magnesium sulfate, and the solvent was removed by evaporation. The residue was separated and purified using silica gel column chromatography to obtain 2.68 g of Compound 2 (yield: 81%). This compound was identified using MS/FAB and $^1$HNMR. $C_{50}H_{34}N_2$ cal. 662.27. found 663.35

δ=8.12-8.10 (m, 2H), 7.87-7.85 (m, 2H), 7.62-7.58 (m, 2H), 7.49-7.39 (m, 11H), 7.31 (d, 2H), 7.29 (s, 2H), 7.08-7.03 (m, 4H), 6.79 (d, 2H), 6.74-6.72 (dd, 2H), 6.65-6.51 (m, 2H), 6.11-6.08 (m, 4H)

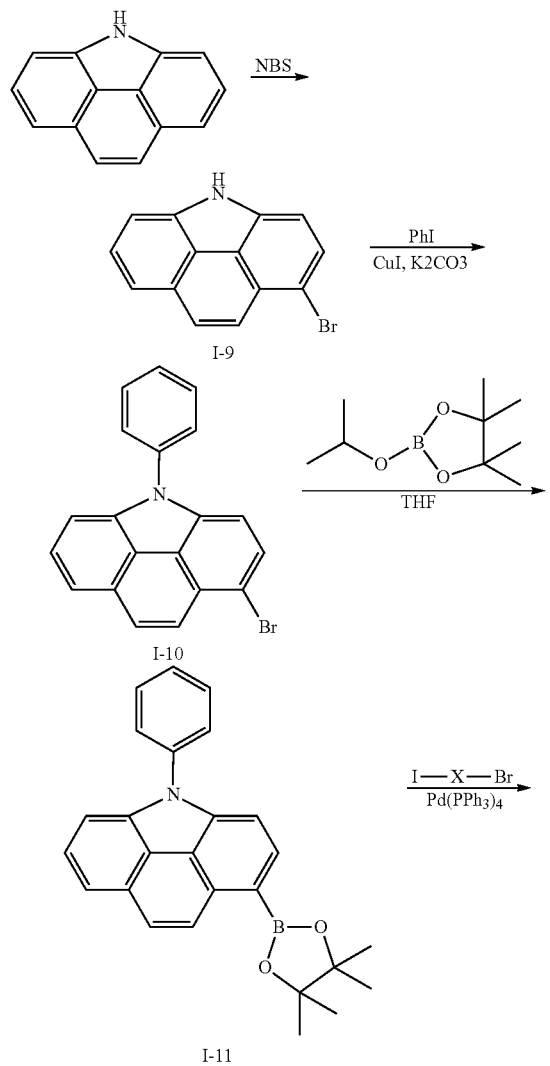

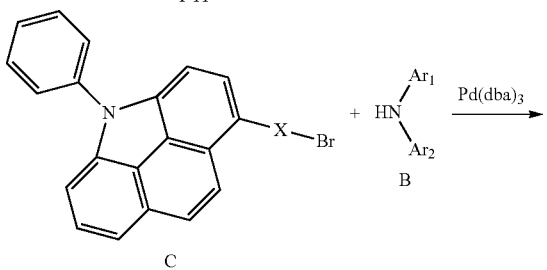

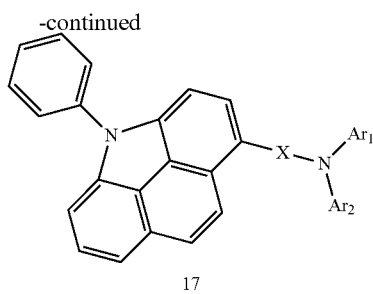

Synthesis of Intermediate I-9

A quantity of 1.78 g (10.0 mmol) of N-bromosuccinimide was added to a solution including 1.91 g (10.0 mmol) of 6H-benzo[def]carbazole that was completely dissolved in 60 mL of carbon tetrachloride ($CCl_4$), then stirred at about 80° C. for about 30 minutes. The reaction solution was cooled to room temperature, then stirred for about 30 minutes to precipitate crystals. The crystals were collected using a filter under reduced pressure, then washed with methanol to obtain 1.1 g of Intermediate I-9 as white crystals (yield: 45%). This compound was identified using LC-MS. $C_{14}H_8BrN$; $M^+245.9$ Synthesis of Intermediate I-10

Intermediate I-10 was synthesized in the same manner as in the synthesis of Intermediate 1-5, except that Intermediate I-9 was used, instead of Intermediate I-4. This compound was identified using LC-MS. $C_{18}H_{12}BrN$; $M^+322.1$ Synthesis of Intermediate I-11

Intermediate I-11 was synthesized in the same manner as in the synthesis of Intermediate 1-8, except that Intermediate I-10 was used, instead of Intermediate I-7. This compound was identified using LC-MS. $C_{24}H_{24}BNO_2$; $M^+322.1$ Synthesis of Intermediate C Quantities of 3.69 g (10 mmol) of Intermediate I-11, 15.0 mmol of I—X—Br, 0.5 mmol of $Pd(PPh_3)_4$, and 30.0 mmol of $K_2CO_3$, respectively, were dissolved in 30 mL of a mixed solvent of $THF/H_2O$ (2:1 by volume), then stirred at about 80° C. for about 5 hours. After the reaction solution was cooled to room temperature, 40 mL of water was added to the reaction solution, which was then extracted three times with 50 mL of diethyl ether. The organic phase was collected and was dried using magnesium sulfate, and the solvent was removed by evaporation. The residue was separated and purified using silica gel column chromatography to obtain Intermediate C. This compound was identified using LC-MS.

Synthesis of Compound 17

Quantities of 1.41 g (5.0 mmol) of Intermediate C (1-bromo-4-iodobenzene), 1.92 g (6.0 mmol) of Intermediate B (bis(biphenyl-4-yl)amine), 0.09 g (0.1 mmol) of $Pd_2(dba)_3$, 0.01 g (0.1 mmol) of $PtBu_3$, and 1.0 g (10.0 mmol) of KOtBu were dissolved in 20 mL of toluene, and stirred at about 85° C. for about 4 hours. After the reaction solution was cooled to room temperature, then extracted three times with 20 mL portions of water and 20 mL portions of diethyl ether. The organic phase was collected and was dried using magnesium sulfate, and the solvent was removed by evaporation. The residue was separated and purified using silica gel column chromatography to obtain 2.54 g of Compound 17 (yield: 77%). This compound was identified using MS/FAB and ¹HNMR. $C_{50}H_{34}N_2$ cal. 662.27. found 663.37

δ=7.79-7.77 (ss, 1H), 7.75-7.73 (m, 1H), 7.65-7.36 (m, 25H), 7.32-7.30 (dd, 1H), 6.96-6.93 (m, 2H), 6.85-6.82 (m, 4H)

Additional compounds were synthesized using appropriate intermediate materials according to the synthetic pathways and the methods described above, and product compounds were identified using ¹H NMR and MS/FAB. The results are shown in Table 1 below.

Synthetic pathways and source materials for other compounds not in Table 1 will be obvious to one of ordinary skill in the art based on the synthetic pathways and source materials described above.

TABLE 1

¹H NMR Data for Selected Derivatives of 4,5-Iminophenanthrene

| | ¹H NMR (CDCl₃, 400 MHz) | MS/FAB found | MS/FAB calc. |
|---|---|---|---|
| 2 | δ = 8.12-8.10 (m, 2H), 7.87-7.85 (m, 2H), 7.62-7.58 (m, 2H), 7.49-7.39 (m, 11H), 7.31 (d, 2H), 7.29 (s, 2H), 7.08-7.03 (m, 4H), 6.79 (d, 2H), 6.74-6.72 (dd, 2H), 6.65-6.51 (m, 2H), 6.11-6.08(m, 4H) | 663.35 | 662.27 |
| 17 | δ = 7.79-7.77 (ss, 1H), 7.75-7.73 (m, 1H), 7.65-7.36 (m, 25H), 7.32-7.30 (dd, 1H), 6.96-6.93 (m, 2H), 6.85-6.82 (m, 4H) | 663.37 | 662.27 |
| 36 | δ = 8.04 (m, 1H), 7.77-7.76 (m, 2H), 7.64-7.62 (m, 2H), 7.57-7.30 (m, 18H), 7.28-7.27 (d, 1H), 7.14-7.08 (m, 2H), 6.79-6.70 (m, 2H), 6.71-6.68 (dd, 1H), 6.53-6.49 (m, 2H), 6.42-6.41 (d, 1H), 1.61 (s, 6H) | 703.31 | 702.30 |
| 38 | δ = 8.23-8.20 (m, 1H), 8.03 (d, 1H), 7.81 (m, 1H), 7.77-7.76 (m, 2H), 7.57-7.40 (m, 13H), 7.39-7.23 (m, 10H), 7.14-7.10 (m, 2H), 6.96-6.93 (dd, 1H), 6.87-6.83 (m, 2H), 6.76-6.73 (dd, 1H), 6.52-6.51 (d, 1H), 1.61 (m, 6H) | 792.33 | 791.33 |
| 43 | δ = 8.04 (d, 1H), 7.86-7.85 (dd, 1H), 7.77-7.75 (dd, 1H), 7.64-7.62 (m, 4H), 7.58-7.56 (ss, 1H), 7.53-7.28 (m, 20H), 7.19-7.06 (m, 12H), 6.81-6.76 (m, 3H), 6.72-6.69 (dd, 1H), 6.53-6.49 (m, 1H), 6.42 (d, 1H) | 903.46 | 902.37 |
| 44 | δ = 8.08 (m, 1H), 7.85-7.82 (m, 2H), 7.78-7.75 (dd, 2H), 7.73-7.70 (m, 2H), 7.64-7.62 (m, 3H), 7.57-7.38 (m, 20H), 7.32-7.29 (m, 2H), 6.86-6.82 (m, 4H), 6.61-6.57 (m, 2H) | 845.37 | 844.36 |
| 52 | δ = 7.77 (s, 4H), 7.75-7.72 (m, 1H), 7.64-7.62 (m, 4H), 7.59-7.57 (m, 2H), 7.54-7.49 (m, 10H), 7.46-7.35 (m, 10H), 7.32-7.30 (dd, 1H), 6.86-6.82 (m, 4H), 6.61-6.57 (m, 2H) | 739.54 | 738.30 |
| 56 | δ = 7.86-7.85 (m, 1H), 7.79-7.77 (ss, 1H), 7.75-7.73 (m, 1H), 7.64-7.38 (m, 20H), 7.32-7.30 (dd, 1H), 7.19-7.06 (m, 11H), 6.89-6.85 (m, 2H), 6.81-6.79 (m, 1H), 6.72-6.70 (dd, 1H), 6.53-6.49 (m, 2H), 6.42 (d, 1H) | 827.42 | 826.33 |
| 59 | δ = 8.13-8.10 (dd, 1H), 8.03 (d, 1H), 7.87-7.85 (m, 1H), 7.77-7.75 (m, 2H), 7.67 (ss, 1H), 7.62 (dd, 1H), 7.59-7.53 (m, 3H), 7.47-7.39 (m, 9H), 7.32 (d, 1H), 7.30-7.25 (m, 2H), 7.07-7.03 (m, 2H), 6.74-6.72 (m, 1H), 6.65-6.58 (m, 2H), 6.32 (d, 1H), 6.06-6.03 (m, 2H), 1.61 (s, 6H) | 677.35 | 676.29 |
| 66 | δ = 8.04 (m, 1H), 8.00-7.98 (m, 1H), 7.86-7.83 (m, 1H), 7.80-7.77 (m, 1H), 7.73 (d, 1H), 7.69-7.57 (m, 10H), 7.52-7.33 (m, 15H), 7.27-7.25 (dd, 1H), 7.20-7.18 (dd, 1H), 6.73-6.70 (dd, 1H), 6.53-6.49 (m, 4H), 6.44 (d, 1H), 1.61 (s, 6H) | 829.43 | 828.35 |
| 68 | δ = 8.13-8.10 (dd, 1H), 8.03 (d, 1H), 7.96-7.94 (ss, 1H), 7.87-7.83 (m, 1H), 7.78-7.73 (m, 3H), 7.86-7.56 (m, 5H), 7.52-7.39 (m, 9H), 7.33-7.31 (dd, 1H), 7.27 (t, 1H), 7.21 (d, 1H), 7.07-7.02 (m, 2H), 6.74-6.72 (m, 1H), 6.65-6.58 (m, 2H), 6.32-6.31 (d, 1H), 6.06-6.03 (m, 2H), 1.61 (s, 6H) | 727.46 | 726.30 |
| 75 | δ = 7.92-7.90 (dd, 1H), 7.88-7.87 (m, 1H), 7.78 (d, 1H), 7.75-7.73 (m, 1H), 7.64-7.60 (m, 5H), 7.55-7.38 (m, 18H), 7.35 (s, 1H), 7.33-7.28 (m, 2H), 6.73-6.70 (dd, 1H), 6.53-6.49 (m, 4H), 6.44 (d, 1H), 1.61 (s, 6H) | 779.43 | 778.33 |
| 83 | δ = 8.13-8.10 (m, 1H), 7.92-7.90 (dd, 1H), 7.88-7.85 (m, 2H), 7.78-7.73 (m, 2H), 7.63-7.60 (m, 3H), 7.52-7.34 (m, 14H), 7.31-7.25 (m, 3H), 7.07-7.02 (m, 2H), 6.74-6.72 (m, 1H), 6.65-6.58 (m, 2H), 6.32-6.31 (d, 1H), 6.06-6.03 (m, 2H), 1.61 (s, 6H) | 753.45 | 752.32 |
| 89 | δ = 8.21-8.20 (tt, 1H), 8.12-8.10 (m, 1H), 7.93-7.90 (dd, 1H), 7.78-7.76 (m, 3H), 7.58-7.45 (m, 8H), 7.40-7.31 (m, 5H), 7.14-7.05 (m, 4H), 6.96-6.94 (dd, 1H), 6.78-6.76 (dd, 1H), 6.67-6.65 (m, 1H), 6.60-6.59 (d, 1H), 6.38-6.35 (m, 2H), 1.61(s, 6H) | 733.42 | 732.26 |
| 90 | δ = 8.03 (d, 1H), 7.77-7.73 (m, 3H), 7.65-7.45 (m, 16H), 7.42-7.30 (m, 5H), 7.24-7.23 (d, 1H), 7.14-7.08 (m, 2H), 6.76-6.72 (dd, 2H), 6.49-6.43 (m, 4H), 1.63 (s, 6H), 1.61 (s, 6H) | 819.45 | 818.37 |
| 92 | δ = 8.17-8.15 (m, 1H), 8.08 (d, 1H), 7.87-7382 (m, 3H), 7.77-7.70 (m, 3H), 7.57-7.38 (m, 13H), 7.32 (s, 1H), 7.30-7.29 (m, 1H), 7.25-7.21 (t, 1H), 7.06-7.01 (m, 2H), 6.86-6.82 (m, 2H), 6.74-6.72 (m, 1H), 6.65-6.61 (m, 1H), 6.07-6.05 (m, 2H) | 637.44 | 636.26 |
| 93 | δ = 8.39 (m, 1H), 8.13-8.11 (m, 1H), 8.06-8.03 (m, 2H), 7.87-7.85 (m, 1H), 7.77-7.75 (m, 1H), 7.69 (dd, 1H), 7.62-7.37 (m, 20H), 7.32-7.27 (m, 2H), 7.23 (d, 1H), 6.85-6.82 (dd, 1H), 6.74-6.71 (m, 1H), 6.45-6.41 (m, 2H) | 727.43 | 726.27 |
| 95 | δ = 8.08 (m, 1H), 8.05-8.03 (m, 1H), 7.77-7.75 (m, 1H), 7.64-7.62 (m, 4H), 7.57-7.39 (m, 20H), 7.36-7.35 (d, 1H), 7.32-7.30 (m, 3H), 6.77-6.75 (m, 1H), 6.46-6.43 (m, 5H) | 713.40 | 712.29 |
| 103 | δ = 7.79-7.77 (ss, 1H), 7.75-7.73 (m, 1H), 7.61-7.46 (m, 9H), 7.44 (s, 1H), 7.40-7.36 (m, 1H), 7.32-7.30 (dd, 1H), 7.08-7.03 (m, 8H), 6.97-6.93 (m, 2H), 6.67-6.65 (m, 4H), 6.61 (s, 8H), 6.16-6.13 (m, 8H) | 845.45 | 844.36 |

Example 1

To manufacture an anode, a corning 15 Ω/cm2 (1200 Å) ITO glass substrate was cut to a size of 50 mm×50 mm×0.7 mm and then sonicated in isopropyl alcohol and pure water each for five minutes, and then cleaned by irradiation with ultraviolet rays for 30 minutes, followed by exposure to ozone. The resulting glass substrate was loaded into a vacuum deposition device.

4,4',4''-Tris(N-(2-naphthyl)-N-phenyl-amino)-triphenylamine (hereinafter, 2-TNATA), was vacuum-deposited onto the anode to a thickness of 600 Å to form an HIL, and Compound 2 as a hole transporting compound was vacuum-deposited onto the HIL to a thickness of 300 Å to form a HTL.

9,10-Di(naphthalene-2-yl)anthracene (hereinafter, DNA) as a blue fluorescent host, and 4,4'-bis[2-(4-(N,N-diphenylamino)phenyl)vinyl]biphenyl (hereinafter, DPAVBi) as a blue fluorescent dopant, were co-deposited in a weight ratio of about 98:2 on the HTL to form an EML having a thickness of about 300 Å.

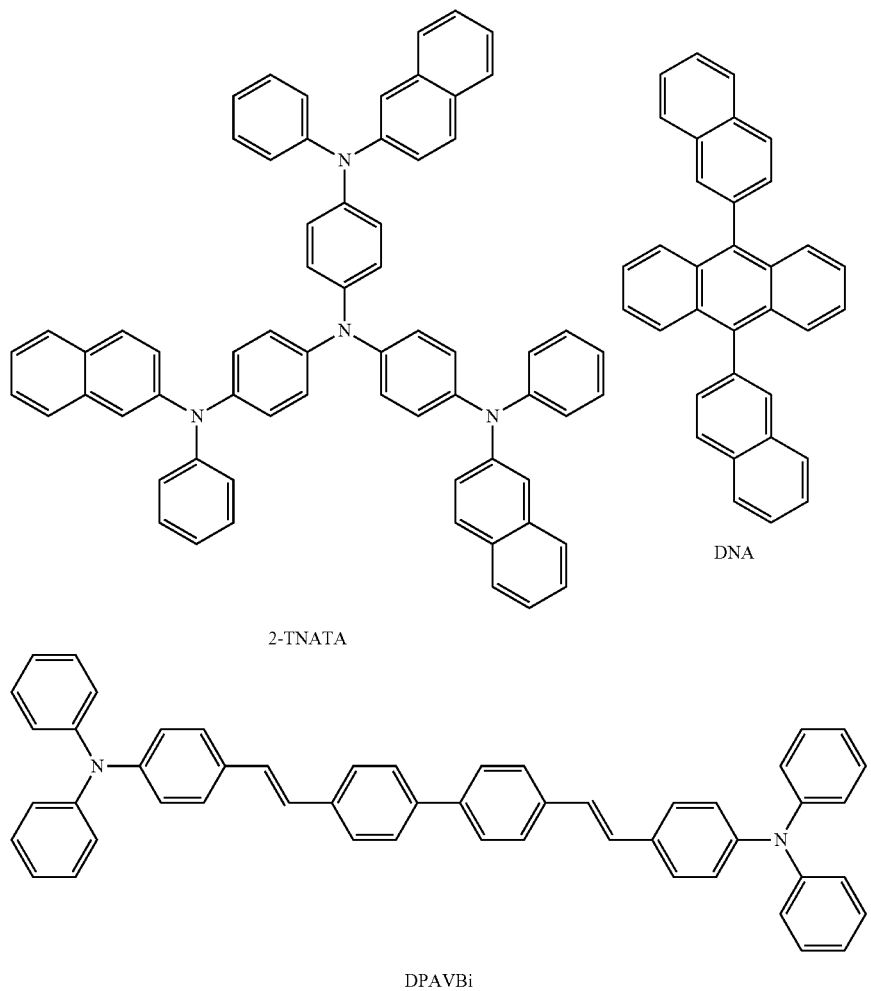

2-TNATA

DNA

DPAVBi

Then, Alq$_3$ was deposited on the EML to form an ETL having a thickness of 300 Å, and then LiF, which is a halogenated alkali metal, was deposited on the ETL to form an EIL having a thickness of 10 Å. Then, Al was vacuum-deposited on the EIL to form a cathode having a thickness of 3000 Å, thereby forming a LiF/Al electrode and completing the manufacture of an organic light-emitting device.

The organic light-emitting device had a driving voltage of about 5.82 V at a current density of 50 mA/cm$^2$, a luminosity of 2,920 cd/m$^2$, a luminescent efficiency of 5.84 cd/A, and a half life-span (hr @100 mA/cm$^2$) of about 288 hours.

Example 2

An organic light-emitting device was manufactured in the same manner as in Example 1, except that Compound 17 was used, instead of Compound 2, to form the HTL.

The organic light-emitting device had a driving voltage of about 5.63 V at a current density of 50 mA/cm$^2$, a luminosity of 2,960 cd/m$^2$, a luminescent efficiency of 5.92 cd/A, and a half life-span (hr @100 mA/cm$^2$) of about 296 hours.

Example 3

An organic light-emitting device was manufactured in the same manner as in Example 1, except that Compound 36 was used, instead of Compound 2, to form the HTL.

The organic light-emitting device had a driving voltage of about 5.45 V at a current density of 50 mA/cm$^2$, a luminosity of 3,065 cd/m$^2$, a luminescent efficiency of 6.13 cd/A, and a half life-span (hr @100 mA/cm$^2$) of about 307 hours.

Example 4

An organic light-emitting device was manufactured in the same manner as in Example 1, except that Compound 44 was used, instead of Compound 2, to form the HTL.

The organic light-emitting device had a driving voltage of about 5.96 V at a current density of 50 mA/cm$^2$, a luminosity of 3,160 cd/m$^2$, a luminescent efficiency of 6.32 cd/A, and a half life-span (hr @100 mA/cm$^2$) of about 312 hours.

Example 5

An organic light-emitting device was manufactured in the same manner as in Example 1, except that Compound 52 was used, instead of Compound 2, to form the HTL.

The organic light-emitting device had a driving voltage of about 6.12 V at a current density of 50 mA/cm$^2$, a luminosity of 3,105 cd/m$^2$, a luminescent efficiency of 6.21 cd/A, and a half life-span (hr @100 mA/cm$^2$) of about 324 hours.

Example 6

An organic light-emitting device was manufactured in the same manner as in Example 1, except that Compound 56 was used, instead of Compound 2, to form the HTL.

The organic light-emitting device had a driving voltage of about 6.23 V at a current density of 50 mA/cm², a luminosity of 2,880 cd/m², a luminescent efficiency of 5.76 cd/A, and a half life-span (hr @100 mA/cm²) of about 345 hours.

Example 7

An organic light-emitting device was manufactured in the same manner as in Example 1, except that Compound 63 was used, instead of Compound 2, to form the HTL.

The organic light-emitting device had a driving voltage of about 5.51 V at a current density of 50 mA/cm², a luminosity of 3,035 cd/m², a luminescent efficiency of 6.07 cd/A, and a half life-span (hr @100 mA/cm²) of about 303 hours.

Example 8

An organic light-emitting device was manufactured in the same manner as in Example 1, except that Compound 75 was used, instead of Compound 2, to form the HTL.

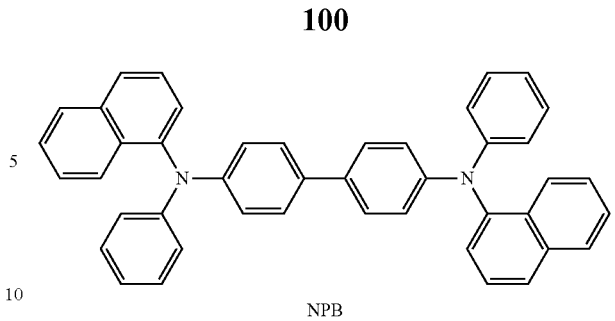

NPB

The organic light-emitting device had a driving voltage of about 7.35 V at a current density of 50 mA/cm², a luminosity of 2,065 cd/m², a luminescent efficiency of 4.13 cd/A, and a half life-span (hr @100 mA/cm²) of about 145 hours.

The organic light-emitting devices manufactured using the compounds represented by Formula 1 according to embodiments as HTL materials had significantly lower driving voltages and improved I—V-L characteristics. In particular, the organic light-emitting devices according to the embodiments had markedly improved lifetimes. The characteristics of the organic light-emitting devices of Examples 1-12 and Comparative Example 1 are shown in Table 2 below.

TABLE 2

Operating Characteristics of OLEDs Comprising Selected Organic Compounds.

|  | HTL material | Driving voltage (V) | Current density (mA/cm²) | Luminance (cd/m²) | Efficiency (cd/A) | Emission color | Half-life span (hr @ 100 mA/cm²) |
|---|---|---|---|---|---|---|---|
| Example 1 | Compound 2 | 5.82 | 50 | 2,920 | 5.84 | Blue | 288 hr |
| Example 2 | Compound 17 | 5.63 | 50 | 2,960 | 5.92 | Blue | 296 hr |
| Example 3 | Compound 36 | 5.45 | 50 | 3,065 | 6.13 | Blue | 307 hr |
| Example 4 | Compound 44 | 5.96 | 50 | 3,160 | 6.32 | Blue | 312 hr |
| Example 5 | Compound 52 | 6.12 | 50 | 3,105 | 6.21 | Blue | 324 hr |
| Example 6 | Compound 56 | 6.23 | 50 | 2,880 | 5.76 | Blue | 345 hr |
| Example 7 | Compound 63 | 5.51 | 50 | 3,035 | 6.07 | Blue | 303 hr |
| Example 8 | Compound 75 | 5.78 | 50 | 2,945 | 5.89 | Blue | 295 hr |
| Example 9 | Compound 90 | 6.02 | 50 | 3,015 | 6.03 | Blue | 276 hr |
| Comparative Example 1 | NPB | 7.35 | 50 | 2,065 | 4.13 | Blue | 145 hr |

The organic light-emitting device had a driving voltage of about 5.78 V at a current density of 50 mA/cm², a luminosity of 2,945 cd/m², a luminescent efficiency of 5.89 cd/A, and a half life-span (hr @100 mA/cm²) of about 295 hours.

Example 9

An organic light-emitting device was manufactured in the same manner as in Example 1, except that Compound 90 was used, instead of Compound 2, to form the HTL.

The organic light-emitting device had a driving voltage of about 6.02 V at a current density of 50 mA/cm², a luminosity of 3,015 cd/m², a luminescent efficiency of 5.89 cd/A, and a half life-span (hr @100 mA/cm²) of about 276 hours.

Comparative Example 1

An organic light-emitting device was manufactured in the same manner as in Example 1, except that NPB was used, instead of Compound 2, to form the HTL.

The novel heterocyclic compound represented by Formula 1 above has an improved charge transporting capability, so it can be used as a hole injecting material or a hole transporting material that is suitable for any color fluorescent and phosphorescent devices, such as red, green, blue, and white fluorescent and phosphorescent devices. Organic light-emitting devices having high efficiency, low driving voltages, high luminances and long lifetimes may be manufactured using the compounds represented by Formula 1.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A heterocyclic compound represented by Formula 1 below:

<Formula 1>

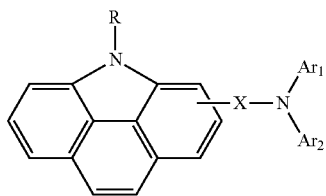

R in Formula 1 being one of a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_3$-$C_{60}$ cycloalkenyl group, a substituted or unsubstituted $C_5$-$C_{60}$ aryl group, and a substituted or unsubstituted $C_6$-$C_{60}$ condensed polycyclic group;

X in Formula 1 being one of the groups represented by Formulae 3b to 3e below:

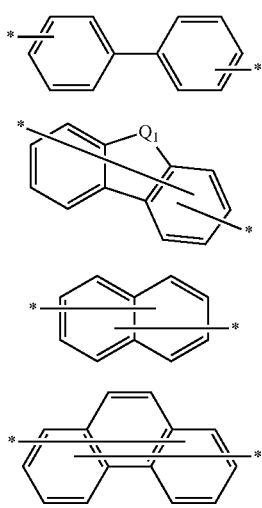

$Q_1$ in Formula 3c being a linking group represented by one of —C($R_{30}$)($R_{31}$)—, —S— and —O—;

$R_{30}$ and $R_{31}$ being each independently one of a hydrogen atom, a deuterium atom, a substituted or unsubstituted $C_1$-$C_{20}$ alkyl group, a substituted or unsubstituted $C_5$-$C_{20}$ aryl group, and a substituted or unsubstituted $C_6$-$C_{20}$ condensed polycyclic group; and

* indicating a binding site; and $Ar_1$ and $Ar_2$ in Formula 1 being each independently one of a substituted or unsubstituted $C_6$-$C_{60}$ aryl group and a substituted or unsubstituted $C_6$-$C_{60}$ condensed polycyclic group.

2. The heterocyclic compound of claim 1, R Formula 1 being one of the groups represented by Formulae 2a to 2b below:

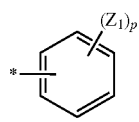

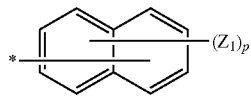

$Z_1$ in Formulae 2a to 2b being one of a hydrogen atom, a deuterium atom, a substituted or unsubstituted $C_1$-$C_{20}$ alkyl group, a substituted or unsubstituted $C_5$-$C_{20}$ aryl group and a substituted or unsubstituted $C_6$-$C_{20}$ condensed polycyclic group;

p being an integer from 1 to 7; and

* indicating a binding site.

3. The heterocyclic compound of claim 1, $Ar_1$ and $Ar_2$ in Formula 1 being each independently one of the groups represented by Formulae 4a to 4c below:

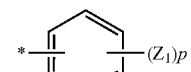

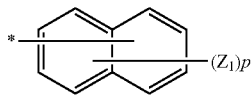

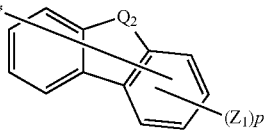

$Q_2$ in Formula 4c being a linking group represented by one of —C($R_{30}$)($R_{31}$)— and —N($R_{32}$)—;

$Z_1$, $R_{30}$, $R_{31}$, and $R_{32}$ being each independently one of a hydrogen atom, a deuterium atom, a substituted or unsubstituted $C_1$-$C_{20}$ alkyl group, a substituted or unsubstituted $C_5$-$C_{20}$ aryl group, an amino group substituted with a substituted or unsubstituted $C_5$-$C_{20}$ aryl group, and a substituted or unsubstituted $C_6$-$C_{20}$ condensed polycyclic group; p being an integer from 1 to 7; and

* indicating a binding site.

4. The heterocyclic compound of claim 1, the compound of Formula 1 being one of the following compounds:

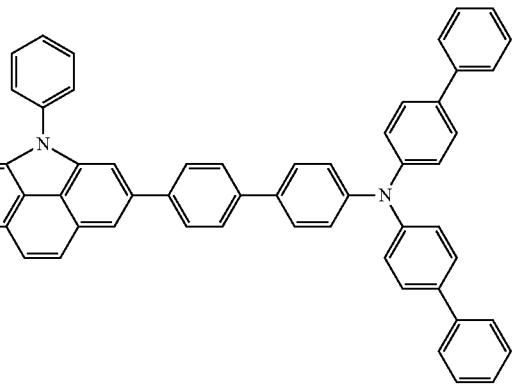

5. An organic light-emitting device comprising:
a first electrode;
a second electrode; and
an organic layer between the first electrode and the second electrode, the organic layer comprising a compound of claim 1.

6. The organic light-emitting device of claim 5, the organic layer being one of a hole injection layer, a hole transport layer and a functional layer having both hole injection and hole transport capabilities.

7. The organic light-emitting device of claim 5, the organic light-emitting device comprising an emission layer, an electron injection layer, an electron transport layer, a functional layer having both electron injection and transport capabilities; one of a hole injection layer, a hole transport layer, and a functional layer having both hole injection and transport capabilities, at least one of the hole injection layer, the hole transport layer, and the functional layer having both hole injection and hole transport capabilities comprising a compound of claim 1; the emission layer comprising one of an anthracene-based compound, an arylamine-based compound and a styryl-based compound.

8. The organic light-emitting device of claim 5, the organic light-emitting device comprising one of an emission layer, an electron injection layer, an electron transport layer, a functional layer having both electron injection and electron transport capabilities, a hole injection layer, a hole transport layer and a functional layer having both hole injection and hole transport capabilities; at least one of the hole injection layer, the hole transport layer and the functional layer having both hole injection and hole transport capabilities comprising the compound of claim 1; the emission layer comprising red, green, blue, and white emission layers, one of which comprises a phosphorescent compound.

9. The organic light-emitting device of claim 8, the hole injection layer, the hole transport layer and the functional layer having both hole injection and hole transport capabilities comprising a charge-generating material.

10. The organic light-emitting device of claim 9, the charge-generating material being a p-dopant.

11. The organic light-emitting device of claim 10, the p-dopant being a quinone derivative.

12. The organic light-emitting device of claim 10, the p-dopant being a metal oxide.

13. The organic light-emitting device of claim 10, the p-dopant being a cyano group-containing compound.

14. The organic light-emitting device of claim 5, the organic layer comprising an electron transport layer, the electron transport layer further comprising a metal complex.

15. The organic light-emitting device of claim 14, the metal complex being a lithium complex.

16. The organic light-emitting device of claim 14, the metal complex being a lithium quinolate (LiQ).

17. The organic light-emitting device of claim 14, the metal complex being Compound 203 below:

<Compound 203>

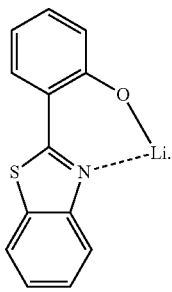

18. The organic light-emitting device of claim 5, the organic layer being formed from the compound of claim 1 using a wet process.

19. A flat panel display device comprising the organic light-emitting device of claim 5, the first electrode of the organic light-emitting device being electrically connected to one of a source electrode and a drain electrode of a thin-film transistor.

20. A heterocyclic compound represented by Formula 1 below:

<Formula 1>

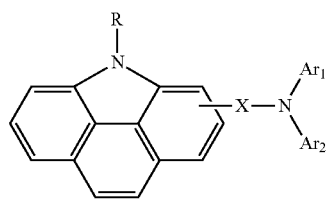

R in Formula 1 being one of a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_3$-$C_{60}$ cycloalkenyl group, a substituted or unsubstituted $C_5$-$C_{60}$ aryl group, and a substituted or unsubstituted $C_6$-$C_{60}$ condensed polycyclic group;

X in Formula 1 being one of the groups represented by Formulae 3a below:

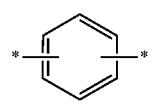

3a

* indicating a binding site; and $Ar_2$ in Formula 1 being each independently one of a substituted or unsubstituted $C_6$-$C_{60}$ aryl group and a substituted or unsubstituted $C_6$-$C_{60}$ condensed polycyclic group, and $Ar_1$ in Formula 1 being each independently one of a substituted or unsubstituted $C_7$-$C_{60}$ aryl group and a substituted or unsubstituted $C_6$-$C_{60}$ condensed polycyclic group.

21. An organic light-emitting device comprising:
a first electrode;
a second electrode; and
an organic layer between the first electrode and the second electrode, the organic layer comprising a compound of claim 20.

22. An organic light-emitting device comprising:
a first electrode;
a second electrode; and
an organic layer between the first electrode and the second electrode, the organic layer comprising a compound of claim 16.

* * * * *